(12) United States Patent
Landrigan et al.

(10) Patent No.: US 10,441,634 B2
(45) Date of Patent: *Oct. 15, 2019

(54) TREATMENT OF PERIPHERAL VASCULAR DISEASE USING PROTEIN SOLUTIONS

(71) Applicant: Biomet Biologics, LLC, Warsaw, IN (US)

(72) Inventors: Matthew D. Landrigan, Fort Wayne, IN (US); Krista Toler, Pierceton, IN (US); Jennifer E. Woodell-May, Warsaw, IN (US); David L. Suter, Rochester Hills, MI (US)

(73) Assignee: Biomet Biologics, LLC, Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/836,249

(22) Filed: Dec. 8, 2017

(65) Prior Publication Data

US 2018/0099026 A1    Apr. 12, 2018

Related U.S. Application Data

(63) Continuation of application No. 13/841,103, filed on Mar. 15, 2013, now Pat. No. 9,895,418.

(51) Int. Cl.
| | | |
|---|---|---|
| *A61K 38/19* | (2006.01) | |
| *A61K 35/15* | (2015.01) | |
| *A61K 35/19* | (2015.01) | |
| *A61K 38/17* | (2006.01) | |
| *A61K 35/14* | (2015.01) | |
| *A61K 38/18* | (2006.01) | |

(52) U.S. Cl.
CPC .............. *A61K 38/19* (2013.01); *A61K 35/14* (2013.01); *A61K 35/15* (2013.01); *A61K 35/19* (2013.01); *A61K 38/1703* (2013.01); *A61K 38/1793* (2013.01); *A61K 38/1808* (2013.01); *A61K 38/1858* (2013.01)

(58) Field of Classification Search
None
See application file for complete search history.

(56) References Cited

U.S. PATENT DOCUMENTS

| | | |
|---|---|---|
| 593,333 A | 11/1897 | Park |
| 1,468,313 A | 9/1923 | Fritz |
| 1,593,814 A | 7/1926 | Vogel |
| 2,722,257 A | 11/1955 | Lockhart |
| 3,013,557 A | 12/1961 | Pallotta |
| 3,141,846 A | 7/1964 | Laven, Jr. |
| 3,159,159 A | 12/1964 | Cohen |
| 3,300,051 A | 1/1967 | Mitchell |
| 3,409,165 A | 11/1968 | Creith |
| 3,420,374 A | 1/1969 | Umeda |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,545,671 A | 12/1970 | Ross |
| 3,583,627 A | 6/1971 | Wilson |
| 3,596,652 A | 8/1971 | Winkelman |
| 3,647,070 A | 3/1972 | Adler |
| 3,654,925 A | 4/1972 | Holderith |
| 3,661,265 A | 5/1972 | Greenspan |
| 3,706,305 A | 12/1972 | Berger et al. |
| 3,706,306 A | 12/1972 | Berger et al. |
| 3,723,244 A | 3/1973 | Breillatt |
| 3,741,400 A | 6/1973 | Dick |
| 3,779,383 A | 12/1973 | Ayres |
| 3,785,549 A | 1/1974 | Latham |
| 3,814,248 A | 6/1974 | Lawhead |
| 3,849,072 A | 11/1974 | Ayres |
| 3,850,369 A | 11/1974 | Bull et al. |
| 3,879,295 A | 4/1975 | Glover et al. |
| 3,887,466 A | 6/1975 | Ayres |
| 3,894,952 A | 7/1975 | Ayres |
| 3,896,733 A | 7/1975 | Rosenberg |
| 3,897,337 A | 7/1975 | Ayres |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,937,211 A | 2/1976 | Merten |
| 3,941,699 A | 3/1976 | Ayres |
| 3,945,928 A | 3/1976 | Ayres |
| 3,951,801 A | 4/1976 | Ayres |
| 3,957,654 A | 5/1976 | Ayres |
| 3,962,085 A | 6/1976 | Liston et al. |
| 3,965,889 A | 6/1976 | Sachs |
| 3,972,812 A | 8/1976 | Gresl, Jr. |
| 3,982,691 A | 9/1976 | Schlutz |
| 4,001,122 A | 1/1977 | Griffin |
| 4,020,831 A | 5/1977 | Adler |
| 4,046,699 A | 9/1977 | Zine, Jr. |
| 4,055,501 A | 10/1977 | Cornell |
| 4,059,108 A | 11/1977 | Latham, Jr. |

(Continued)

FOREIGN PATENT DOCUMENTS

| | | |
|---|---|---|
| AU | 696278 B2 | 9/1998 |
| AU | 748575 B2 | 6/2002 |

(Continued)

OTHER PUBLICATIONS

Smith et al., Immunity, vol. 18, pp. 87-96 (Year: 2003).*

(Continued)

*Primary Examiner* — Daniel E Kolker
*Assistant Examiner* — Jegatheesan Seharaseyon
(74) *Attorney, Agent, or Firm* — Schwegman Lundberg & Woessner, P.A.

(57) ABSTRACT

Methods of treating peripheral vascular disease comprising administering a protein solution site of a defect at least two proteins from the group IL-1ra, sTNF-RI, sTNF-RII, IGF-I, EGF, HGF, PDGF-AB, PDGF-BB, VEGF, TGF-β1, and sIL-1RII. The solution may also comprise white blood cells, platelets, concentrated bone marrow aspirate, and combinations thereof.

19 Claims, 5 Drawing Sheets

(56) References Cited

U.S. PATENT DOCUMENTS

| | | |
|---|---|---|
| 4,066,549 A | 1/1978 | Oeser et al. |
| 4,077,396 A | 3/1978 | Wardlaw et al. |
| 4,088,582 A | 5/1978 | Murty |
| 4,146,172 A | 3/1979 | Cullis et al. |
| 4,152,270 A | 5/1979 | Cornell |
| 4,154,690 A | 5/1979 | Ballies |
| 4,159,896 A | 7/1979 | Levine et al. |
| 4,187,979 A | 2/1980 | Cullis et al. |
| 4,189,385 A | 2/1980 | Greenspan |
| 4,203,840 A | 5/1980 | Stoeppler et al. |
| 4,204,537 A | 5/1980 | Latham, Jr. |
| 4,225,580 A | 9/1980 | Rothman et al. |
| 4,229,298 A | 10/1980 | Bange |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. |
| 4,322,298 A | 3/1982 | Persidsky |
| 4,332,351 A | 6/1982 | Kellogg |
| 4,362,567 A | 12/1982 | Schwarz et al. |
| 4,364,832 A | 12/1982 | Ballies |
| 4,377,572 A | 3/1983 | Schwarz et al. |
| 4,379,849 A | 4/1983 | Heimreid |
| 4,411,794 A | 10/1983 | Schwinn et al. |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi |
| 4,427,650 A | 1/1984 | Stroetmann |
| 4,427,651 A | 1/1984 | Stroetmann |
| 4,442,655 A | 4/1984 | Stroetmann |
| 4,443,345 A | 4/1984 | Wells |
| 4,445,550 A | 5/1984 | Davis et al. |
| 4,446,021 A | 5/1984 | Aufderhaar et al. |
| 4,453,927 A | 6/1984 | Sinko |
| 4,453,939 A | 6/1984 | Zimmerman et al. |
| 4,464,167 A | 8/1984 | Schoendorfer |
| 4,511,662 A | 4/1985 | Baran et al. |
| 4,537,767 A | 8/1985 | Rothman et al. |
| RE32,089 E | 3/1986 | Blatt et al. |
| 4,577,514 A | 3/1986 | Bradley et al. |
| 4,610,656 A | 9/1986 | Mortensen |
| 4,617,009 A | 10/1986 | Ohlin |
| 4,627,879 A | 12/1986 | Rose et al. |
| 4,631,055 A | 12/1986 | Redl et al. |
| 4,632,761 A | 12/1986 | Bowers |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger |
| 4,708,799 A | 11/1987 | Gerlach et al. |
| 4,714,457 A | 12/1987 | Alterbaum |
| 4,722,790 A | 2/1988 | Cawley et al. |
| 4,724,317 A | 2/1988 | Brown |
| 4,735,616 A | 4/1988 | Eibl et al. |
| 4,735,726 A | 4/1988 | Duggins |
| 4,738,655 A | 4/1988 | Brimhall et al. |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,834,890 A | 5/1989 | Brown et al. |
| 4,839,058 A | 6/1989 | Cawley et al. |
| 4,844,818 A | 7/1989 | Smith |
| 4,846,780 A | 7/1989 | Galloway et al. |
| 4,846,835 A | 7/1989 | Grande |
| 4,850,952 A | 7/1989 | Figdor et al. |
| 4,853,137 A | 8/1989 | Ersson |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani |
| 4,900,453 A | 2/1990 | Sedlmayer |
| 4,902,281 A | 2/1990 | Avoy |
| 4,909,251 A | 3/1990 | Seelich |
| 4,915,847 A | 4/1990 | Dillon et al. |
| 4,917,801 A | 4/1990 | Luderer et al. |
| 4,928,603 A | 5/1990 | Rose et al. |
| 4,929,242 A | 5/1990 | Desecki et al. |
| 4,933,291 A | 6/1990 | Daiss et al. |
| 4,939,081 A | 7/1990 | Figdor et al. |
| 4,943,273 A | 7/1990 | Pages |
| 4,946,601 A | 8/1990 | Fiehler |
| 4,950,220 A | 8/1990 | Wells et al. |
| 4,957,637 A | 9/1990 | Cornell |
| 4,957,638 A | 9/1990 | Smith |
| 4,973,168 A | 11/1990 | Chan |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'donnell, Jr. |
| 5,019,243 A | 5/1991 | Mcewen et al. |
| 5,024,613 A | 6/1991 | Vasconcellos et al. |
| 5,030,215 A | 7/1991 | Morse et al. |
| 5,030,341 A | 7/1991 | Mcewen et al. |
| 5,039,401 A | 8/1991 | Columbus et al. |
| 5,045,048 A | 9/1991 | Kaleskas |
| 5,047,004 A | 9/1991 | Wells |
| 5,053,127 A | 10/1991 | Schoendorfer et al. |
| 5,053,134 A | 10/1991 | Luderer et al. |
| 5,071,570 A | 12/1991 | Shiraki et al. |
| 5,075,222 A | 12/1991 | Hannum et al. |
| 5,080,262 A | 1/1992 | Herold et al. |
| 5,086,784 A | 2/1992 | Levine et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling |
| 5,178,602 A | 1/1993 | Wells |
| 5,185,001 A | 2/1993 | Galanakis |
| 5,188,583 A | 2/1993 | Guigan |
| 5,190,057 A | 3/1993 | Sarfarazi |
| 5,190,759 A | 3/1993 | Lindblad et al. |
| 5,197,985 A | 3/1993 | Caplan |
| 5,203,825 A | 4/1993 | Haynes |
| 5,204,537 A | 4/1993 | Bennet et al. |
| 5,206,023 A | 4/1993 | Hunziker |
| 5,207,638 A | 5/1993 | Choksi et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,226,914 A | 7/1993 | Caplan et al. |
| 5,234,608 A | 8/1993 | Duff |
| 5,236,604 A | 8/1993 | Fiehler |
| 5,251,786 A | 10/1993 | Sarrine |
| 5,258,126 A | 11/1993 | Pall et al. |
| 5,260,420 A | 11/1993 | Burnouf-radosevich et al. |
| 5,269,927 A | 12/1993 | Fiehler |
| 5,271,852 A | 12/1993 | Luoma, II |
| 5,279,825 A | 1/1994 | Wehling |
| 5,281,342 A | 1/1994 | Biesel et al. |
| 5,290,552 A | 3/1994 | Sierra et al. |
| 5,290,918 A | 3/1994 | Bui-khac |
| 5,298,171 A | 3/1994 | Biesel |
| 5,304,372 A | 4/1994 | Michalski et al. |

(56) References Cited

U.S. PATENT DOCUMENTS

| | | |
|---|---|---|
| 5,316,674 A | 5/1994 | Pall et al. |
| 5,318,524 A | 6/1994 | Morse et al. |
| 5,318,782 A | 6/1994 | Weis-fogh |
| 5,321,126 A | 6/1994 | Van Dommelen et al. |
| 5,322,620 A | 6/1994 | Brown et al. |
| 5,330,974 A | 7/1994 | Pines et al. |
| 5,344,752 A | 9/1994 | Murphy |
| 5,354,483 A | 10/1994 | Furse |
| 5,359,032 A | 10/1994 | Dayer et al. |
| 5,370,221 A | 12/1994 | Magnusson et al. |
| 5,370,802 A | 12/1994 | Brown |
| 5,372,945 A | 12/1994 | Alchas et al. |
| 5,376,263 A | 12/1994 | Fischel |
| 5,387,187 A | 2/1995 | Fell et al. |
| 5,393,674 A | 2/1995 | Levine et al. |
| 5,395,923 A | 3/1995 | Bui-khac et al. |
| 5,403,272 A | 4/1995 | Deniega et al. |
| 5,405,607 A | 4/1995 | Epstein |
| 5,409,833 A | 4/1995 | Hu et al. |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,474,687 A | 12/1995 | Van Vlasselaer |
| 5,480,378 A | 1/1996 | Weis-fogh et al. |
| 5,484,383 A | 1/1996 | Fitch, Jr. et al. |
| 5,486,359 A | 1/1996 | Caplan et al. |
| 5,494,578 A | 2/1996 | Brown |
| 5,494,592 A | 2/1996 | Latham, Jr. et al. |
| 5,501,371 A | 3/1996 | Schwartz-feldman |
| 5,505,685 A | 4/1996 | Antwiler |
| 5,510,102 A | 4/1996 | Cochrum |
| 5,520,885 A | 5/1996 | Coelho et al. |
| 5,525,477 A | 6/1996 | Hassouna |
| 5,533,518 A | 7/1996 | Vogler |
| 5,560,830 A | 10/1996 | Coleman et al. |
| 5,571,418 A | 11/1996 | Lee et al. |
| 5,575,778 A | 11/1996 | Hardt et al. |
| 5,577,513 A | 11/1996 | Van Vlasselaer |
| 5,585,007 A | 12/1996 | Antanvich et al. |
| 5,588,958 A | 12/1996 | Cunningham et al. |
| 5,589,462 A | 12/1996 | Patat et al. |
| 5,599,558 A | 2/1997 | Gordinier et al. |
| 5,601,711 A | 2/1997 | Sklar et al. |
| 5,601,727 A | 2/1997 | Bormann et al. |
| 5,603,845 A | 2/1997 | Holm |
| 5,607,579 A | 3/1997 | Latham, Jr. et al. |
| 5,614,106 A | 3/1997 | Payrat et al. |
| 5,618,663 A | 4/1997 | Delmas |
| 5,632,895 A | 5/1997 | Tsukagoshi et al. |
| 5,632,905 A | 5/1997 | Haynes |
| 5,641,414 A | 6/1997 | Brown |
| 5,641,622 A | 6/1997 | Lake et al. |
| 5,643,192 A | 7/1997 | Hirsh |
| 5,643,193 A | 7/1997 | Papillon et al. |
| 5,645,540 A | 7/1997 | Henniges et al. |
| 5,646,004 A | 7/1997 | Van Vlasselaer |
| 5,648,223 A | 7/1997 | Van Vlasselaer |
| 5,649,903 A | 7/1997 | Deniega et al. |
| 5,663,051 A | 9/1997 | Vlasselaer |
| 5,674,173 A | 10/1997 | Hlavinka et al. |
| 5,707,331 A | 1/1998 | Wells et al. |
| 5,707,647 A | 1/1998 | Dunn et al. |
| 5,707,876 A | 1/1998 | Levine |
| 5,716,616 A | 2/1998 | Prockop et al. |
| 5,723,331 A | 3/1998 | Tubo et al. |
| 5,724,988 A | 3/1998 | Dennehey et al. |
| 5,733,466 A | 3/1998 | Benebo et al. |
| 5,733,545 A | 3/1998 | Hood, III |
| 5,736,033 A | 4/1998 | Coleman et al. |
| 5,738,784 A | 4/1998 | Holm et al. |
| 5,738,796 A | 4/1998 | Bormann et al. |
| 5,750,025 A | 5/1998 | Holmes et al. |
| 5,750,658 A | 5/1998 | Coelho et al. |
| 5,762,798 A | 6/1998 | Wenthold et al. |
| 5,785,700 A | 7/1998 | Olson |
| 5,786,217 A | 7/1998 | Tubo et al. |
| 5,788,662 A | 8/1998 | Antanavich et al. |
| 5,792,344 A | 8/1998 | Holm |
| 5,792,450 A | 8/1998 | Wilson et al. |
| 5,795,489 A | 8/1998 | Holm |
| 5,795,571 A | 8/1998 | Cederholm-Williams et al. |
| 5,795,751 A | 8/1998 | Apel |
| 5,811,094 A | 9/1998 | Caplan et al. |
| 5,811,151 A | 9/1998 | Hendriks et al. |
| 5,817,519 A | 10/1998 | Zelmanovic et al. |
| 5,823,986 A | 10/1998 | Peterson |
| 5,824,084 A | 10/1998 | Muschler |
| 5,830,359 A | 11/1998 | Knight et al. |
| 5,833,866 A | 11/1998 | Brown |
| 5,834,418 A | 11/1998 | Brazeau et al. |
| 5,837,150 A | 11/1998 | Langley et al. |
| 5,840,502 A | 11/1998 | Van Vlasselaer |
| 5,842,477 A | 12/1998 | Naughton et al. |
| 5,846,427 A | 12/1998 | Kessler et al. |
| 5,853,600 A | 12/1998 | Mcneal et al. |
| 5,860,937 A | 1/1999 | Cohen |
| 5,863,892 A | 1/1999 | Stern et al. |
| 5,865,785 A | 2/1999 | Bischof |
| 5,885,239 A | 3/1999 | Headley et al. |
| 5,889,584 A | 3/1999 | Wardlaw |
| 5,895,346 A | 4/1999 | Wells et al. |
| 5,895,575 A | 4/1999 | Kraus et al. |
| 5,899,874 A | 5/1999 | Jonsson |
| 5,900,245 A | 5/1999 | Sawhney et al. |
| 5,906,934 A | 5/1999 | Grande et al. |
| 5,916,557 A | 6/1999 | Berlowitz-tarrant et al. |
| 5,916,743 A | 6/1999 | Lake et al. |
| 5,918,622 A | 7/1999 | Perez |
| 5,924,972 A | 7/1999 | Turvaville et al. |
| 5,934,803 A | 8/1999 | Hutter |
| 5,938,621 A | 8/1999 | Kelly et al. |
| 5,951,160 A | 9/1999 | Ronk |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm |
| 5,961,210 A | 10/1999 | Mccardel et al. |
| 5,980,734 A | 11/1999 | Itoh |
| 5,980,757 A | 11/1999 | Brown et al. |
| 5,985,315 A | 11/1999 | Patat et al. |
| 5,997,544 A | 12/1999 | Nies et al. |
| 6,007,811 A | 12/1999 | Sawyer et al. |
| 6,010,627 A | 1/2000 | Hood, III |
| 6,011,490 A | 1/2000 | Tonnesen et al. |
| 6,020,196 A | 2/2000 | Hu et al. |
| 6,022,306 A | 2/2000 | Dumont et al. |
| 6,025,201 A | 2/2000 | Zelmanovic et al. |
| 6,027,655 A | 2/2000 | Holm |
| 6,049,026 A | 4/2000 | Muschler |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,096,728 A | 8/2000 | Collins et al. |
| 6,102,843 A | 8/2000 | Kelley et al. |
| 6,117,425 A | 9/2000 | Macphee et al. |
| 6,123,655 A | 9/2000 | Fell |
| 6,150,163 A | 11/2000 | McPherson et al. |
| 6,153,113 A | 11/2000 | Goodrich et al. |
| 6,183,737 B1 | 2/2001 | Zaleske et al. |
| 6,196,987 B1 | 3/2001 | Holmes et al. |
| 6,197,325 B1 | 3/2001 | Macphee et al. |
| 6,200,287 B1 | 3/2001 | Keller et al. |

(56) References Cited

U.S. PATENT DOCUMENTS

| | | |
|---|---|---|
| 6,200,606 B1 | 3/2001 | Peterson et al. |
| 6,214,338 B1 | 4/2001 | Antanavich et al. |
| 6,221,315 B1 | 4/2001 | Giesler et al. |
| 6,245,900 B1 | 6/2001 | Yamasaki et al. |
| 6,264,890 B1 | 7/2001 | Boehringer et al. |
| 6,274,090 B1 | 8/2001 | Coelho et al. |
| 6,277,961 B1 | 8/2001 | Hock et al. |
| 6,280,400 B1 | 8/2001 | Niermann |
| 6,286,670 B1 | 9/2001 | Smith |
| 6,287,558 B1 | 9/2001 | Lanza et al. |
| 6,296,602 B1 | 10/2001 | Headley |
| 6,316,247 B1 | 11/2001 | Katz et al. |
| 6,322,785 B1 | 11/2001 | Landesberg et al. |
| 6,327,491 B1 | 12/2001 | Franklin et al. |
| 6,328,765 B1 | 12/2001 | Hardwick et al. |
| 6,334,842 B1 | 1/2002 | Hlavinka et al. |
| 6,337,072 B1 | 1/2002 | Ford et al. |
| 6,342,157 B1 | 1/2002 | Hood, III |
| 6,351,659 B1 | 2/2002 | Vilsmeier |
| 6,355,239 B1 | 3/2002 | Bruder et al. |
| 6,368,298 B1 | 4/2002 | Beretta et al. |
| 6,368,498 B1 | 4/2002 | Guilmette |
| 6,398,972 B1 | 6/2002 | Blasetti et al. |
| 6,406,671 B1 | 6/2002 | Dicesare et al. |
| 6,409,528 B1 | 6/2002 | Bodnar |
| 6,410,344 B1 | 6/2002 | Chung |
| 6,417,004 B1 | 7/2002 | Brady et al. |
| 6,440,444 B2 | 8/2002 | Boyce et al. |
| 6,444,228 B1 | 9/2002 | Baugh et al. |
| 6,464,624 B2 | 10/2002 | Pages |
| 6,471,069 B2 | 10/2002 | Lin et al. |
| 6,472,162 B2 | 10/2002 | Coelho et al. |
| 6,487,992 B1 | 12/2002 | Hollis |
| 6,508,778 B1 | 1/2003 | Verkaart et al. |
| 6,516,953 B1 | 2/2003 | Dicesare et al. |
| 6,523,698 B1 | 2/2003 | Dennehey et al. |
| 6,544,162 B1 | 4/2003 | Van Wie et al. |
| 6,544,727 B1 | 4/2003 | Hei |
| 6,558,341 B1 | 5/2003 | Swisher |
| 6,563,953 B2 | 5/2003 | Lin et al. |
| 6,596,180 B2 | 7/2003 | Baugh et al. |
| 6,599,873 B1 | 7/2003 | Sommer et al. |
| 6,623,472 B1 | 9/2003 | Reincke et al. |
| 6,623,959 B2 | 9/2003 | Harris |
| 6,629,919 B2 | 10/2003 | Egozy et al. |
| 6,638,503 B2 | 10/2003 | Chitte |
| 6,641,708 B1 | 11/2003 | Huang et al. |
| 6,645,388 B2 | 11/2003 | Sheikh-ali |
| 6,649,072 B2 | 11/2003 | Brandt et al. |
| 6,676,629 B2 | 1/2004 | Andrew et al. |
| 6,713,246 B1 | 3/2004 | Reinecke et al. |
| 6,716,187 B1 | 4/2004 | Jorgensen et al. |
| 6,719,901 B2 | 4/2004 | Dolecek et al. |
| 6,733,471 B1 | 5/2004 | Ericson et al. |
| 6,758,978 B1 | 7/2004 | Bedell |
| 6,759,188 B2 | 7/2004 | Reinecke et al. |
| 6,764,531 B2 | 7/2004 | Hogan |
| 6,777,231 B1 | 8/2004 | Katz et al. |
| 6,790,371 B2 | 9/2004 | Dolecek |
| 6,803,022 B2 | 10/2004 | Dicesare et al. |
| 6,811,777 B2 | 11/2004 | Mishra |
| 6,830,762 B2 | 12/2004 | Baugh et al. |
| 6,835,353 B2 | 12/2004 | Smith et al. |
| 6,835,377 B2 | 12/2004 | Goldberg et al. |
| RE38,730 E | 4/2005 | Jakary et al. |
| 6,899,813 B2 | 5/2005 | Dolecek et al. |
| 6,905,612 B2 | 6/2005 | Dorian et al. |
| 6,911,202 B2 | 6/2005 | Amir et al. |
| RE38,757 E | 7/2005 | Jakary et al. |
| 6,955,642 B1 | 10/2005 | Simon |
| 6,979,307 B2 | 12/2005 | Beretta et al. |
| 7,011,644 B1 | 3/2006 | Andrew et al. |
| 7,011,852 B2 | 3/2006 | Sukavaneshvar et al. |
| 7,077,273 B2 | 7/2006 | Ellsworth et al. |
| 7,077,827 B2 | 7/2006 | Greenfield |
| 7,148,209 B2 | 12/2006 | Hoemann et al. |
| 7,155,288 B2 | 12/2006 | Soykan et al. |
| 7,166,283 B2 | 1/2007 | Tsuji et al. |
| 7,179,391 B2 | 2/2007 | Leach et al. |
| 7,195,606 B2 | 3/2007 | Ballin |
| 7,223,346 B2 | 5/2007 | Dorian et al. |
| 7,273,886 B2 | 9/2007 | Olivero |
| 7,302,882 B2 | 12/2007 | Reuter |
| 7,354,515 B2 | 4/2008 | Coull et al. |
| 7,374,678 B2 | 5/2008 | Leach et al. |
| 7,411,006 B2 | 8/2008 | Shanbrom |
| 7,465,293 B2 | 12/2008 | Reinecke et al. |
| 7,470,371 B2 | 12/2008 | Dorian et al. |
| 7,520,849 B1 | 4/2009 | Simon |
| 7,531,355 B2 | 5/2009 | Rodriguez et al. |
| 7,553,413 B2 | 6/2009 | Dorian et al. |
| 7,608,258 B2 | 10/2009 | Mishra |
| 7,678,385 B2 | 3/2010 | Reddi |
| 7,694,828 B2 | 4/2010 | Swift et al. |
| 7,708,152 B2 | 5/2010 | Dorian et al. |
| 7,806,276 B2 | 10/2010 | Leach et al. |
| 7,845,499 B2 | 12/2010 | Higgins et al. |
| 7,867,765 B2 | 1/2011 | Faustman et al. |
| 7,901,344 B2 | 3/2011 | Yoo |
| 7,901,584 B2 | 3/2011 | Dorian et al. |
| 7,914,689 B2 | 3/2011 | Higgins et al. |
| 7,987,995 B2 | 8/2011 | Dorian et al. |
| 7,992,725 B2 | 8/2011 | Leach et al. |
| 8,048,297 B2 | 11/2011 | Leach et al. |
| 8,048,321 B2 | 11/2011 | Leach et al. |
| 8,062,534 B2 | 11/2011 | Higgins et al. |
| 8,067,534 B2 | 11/2011 | Jagota |
| 8,093,211 B2 | 1/2012 | Tennenbaum et al. |
| 8,202,539 B2 | 6/2012 | Behnam et al. |
| 8,567,609 B2 | 10/2013 | Landrigan et al. |
| 8,596,470 B2 | 12/2013 | Leach et al. |
| 8,753,690 B2 | 6/2014 | Higgins et al. |
| 8,783,470 B2 | 7/2014 | Hecker et al. |
| 8,801,586 B2 | 8/2014 | Dorian et al. |
| 8,808,551 B2 | 8/2014 | Leach et al. |
| 8,950,586 B2 | 2/2015 | Dorian et al. |
| 8,992,862 B2 | 3/2015 | Leach et al. |
| 9,011,800 B2 | 4/2015 | Leach et al. |
| 9,119,829 B2 | 9/2015 | Higgins et al. |
| 9,308,224 B2 | 4/2016 | Higgins et al. |
| 9,556,243 B2 | 1/2017 | Leach et al. |
| 9,701,728 B2 | 7/2017 | Higgins et al. |
| 9,758,806 B2 | 9/2017 | Woodell-May et al. |
| 9,763,875 B2 | 9/2017 | Higgins et al. |
| 9,878,011 B2 | 1/2018 | Landrigan et al. |
| 9,895,418 B2 * | 2/2018 | Landrigan .............. A61K 38/19 |
| 10,106,587 B2 | 10/2018 | Higgins et al. |
| 10,143,725 B2 | 12/2018 | Toler et al. |
| 10,208,095 B2 | 2/2019 | Leach et al. |
| 2001/0009757 A1 | 7/2001 | Bischof et al. |
| 2001/0016195 A1 | 8/2001 | Tobinick |
| 2001/0053764 A1 | 12/2001 | Sims et al. |
| 2002/0009454 A1 | 1/2002 | Boone et al. |
| 2002/0032112 A1 | 3/2002 | Pages |
| 2002/0035820 A1 | 3/2002 | Farris |
| 2002/0076400 A1 | 6/2002 | Katz et al. |
| 2002/0077276 A1 | 6/2002 | Fredeking et al. |
| 2002/0082220 A1 | 6/2002 | Hoemann et al. |
| 2002/0090711 A1 | 7/2002 | Karlsson |
| 2002/0104808 A1 | 8/2002 | Blasetti et al. |
| 2002/0114775 A1 | 8/2002 | Pathak |
| 2002/0119179 A1 | 8/2002 | Rezania et al. |
| 2002/0161449 A1 | 10/2002 | Muschler |
| 2002/0169408 A1 | 11/2002 | Beretta et al. |
| 2002/0172666 A1 | 11/2002 | Sacchi et al. |
| 2002/0182664 A1 | 12/2002 | Dolecek et al. |
| 2002/0192632 A1 | 12/2002 | Hei et al. |
| 2003/0033021 A1 | 2/2003 | Plouhar et al. |
| 2003/0033022 A1 | 2/2003 | Plouhar et al. |
| 2003/0050709 A1 | 3/2003 | Noth et al. |
| 2003/0050710 A1 | 3/2003 | Petersen et al. |
| 2003/0055511 A1 | 3/2003 | Schryver et al. |
| 2003/0082152 A1 | 5/2003 | Hedrick et al. |
| 2003/0091536 A1 | 5/2003 | Frisbie et al. |

(56) References Cited

U.S. PATENT DOCUMENTS

| | | |
|---|---|---|
| 2003/0099650 A1 | 5/2003 | Ho et al. |
| 2003/0138910 A1 | 7/2003 | Reinecke et al. |
| 2003/0185803 A1 | 10/2003 | Kadiyala et al. |
| 2003/0191429 A1 | 10/2003 | Andrew et al. |
| 2003/0194397 A1 | 10/2003 | Mishra |
| 2003/0198687 A1 | 10/2003 | Bennett |
| 2003/0205538 A1 | 11/2003 | Dorian et al. |
| 2004/0005246 A1 | 1/2004 | Efthimiadis et al. |
| 2004/0013575 A1 | 1/2004 | Stevens et al. |
| 2004/0120942 A1 | 6/2004 | Mcginnis et al. |
| 2004/0156823 A1 | 8/2004 | Reinecke et al. |
| 2004/0171146 A1 | 9/2004 | Katz et al. |
| 2004/0182395 A1 | 9/2004 | Brookman |
| 2004/0182788 A1 | 9/2004 | Dorian et al. |
| 2004/0182795 A1 | 9/2004 | Dorian et al. |
| 2004/0219182 A1 | 11/2004 | Gomes et al. |
| 2004/0251217 A1 | 12/2004 | Leach et al. |
| 2004/0258671 A1 | 12/2004 | Watkins |
| 2005/0049640 A1 | 3/2005 | Gurtner et al. |
| 2005/0059589 A1 | 3/2005 | Mullarkey |
| 2005/0076396 A1 | 4/2005 | Katz et al. |
| 2005/0084961 A1 | 4/2005 | Hedrick et al. |
| 2005/0084962 A1 | 4/2005 | Simon |
| 2005/0100536 A1 | 5/2005 | Mishra |
| 2005/0109716 A1 | 5/2005 | Leach et al. |
| 2005/0130301 A1 | 6/2005 | Mckay et al. |
| 2005/0145187 A1 | 7/2005 | Gray |
| 2005/0152905 A1 | 7/2005 | Omoigui |
| 2005/0153441 A1 | 7/2005 | Hedrick et al. |
| 2005/0153442 A1 | 7/2005 | Katz et al. |
| 2005/0186120 A1 | 8/2005 | Dorian et al. |
| 2005/0186193 A1 | 8/2005 | Mishra |
| 2005/0196393 A1 | 9/2005 | Shanbrom |
| 2005/0196874 A1 | 9/2005 | Dorian et al. |
| 2005/0197293 A1 | 9/2005 | Mellis et al. |
| 2005/0247715 A1 | 11/2005 | Ellsworth et al. |
| 2005/0260174 A1 | 11/2005 | Fraser et al. |
| 2005/0260175 A1 | 11/2005 | Hedrick et al. |
| 2005/0271738 A1 | 12/2005 | Simon |
| 2005/0282275 A1 | 12/2005 | Katz et al. |
| 2006/0046960 A1 | 3/2006 | Mckay et al. |
| 2006/0051865 A1 | 3/2006 | Higgins et al. |
| 2006/0057223 A1 | 3/2006 | Dimauro et al. |
| 2006/0057693 A1 | 3/2006 | Simon |
| 2006/0083720 A1 | 4/2006 | Fraser et al. |
| 2006/0121002 A1 | 6/2006 | Rolland et al. |
| 2006/0140923 A1 | 6/2006 | Evangelista |
| 2006/0151384 A1 | 7/2006 | Ellsworth et al. |
| 2006/0171948 A1 | 8/2006 | Weinstein et al. |
| 2006/0175244 A1 | 8/2006 | Dorian et al. |
| 2006/0175268 A1 | 8/2006 | Dorian et al. |
| 2006/0178610 A1 | 8/2006 | Nowakowski |
| 2006/0196885 A1 | 9/2006 | Leach et al. |
| 2006/0243676 A1 | 11/2006 | Swift et al. |
| 2006/0263407 A1 | 11/2006 | Mishra |
| 2006/0263408 A1 | 11/2006 | Rezania et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0027082 A1 | 2/2007 | Hasty et al. |
| 2007/0034579 A1 | 2/2007 | Dorian et al. |
| 2007/0036768 A1 | 2/2007 | Fraser et al. |
| 2007/0075016 A1 | 4/2007 | Leach |
| 2007/0092494 A1 | 4/2007 | Higgins et al. |
| 2007/0105769 A1 | 5/2007 | Simon |
| 2007/0207161 A1 | 9/2007 | Ralph |
| 2007/0208321 A1 | 9/2007 | Leach et al. |
| 2007/0299472 A1 | 12/2007 | Brighton |
| 2008/0011684 A1 | 1/2008 | Dorian et al. |
| 2008/0019964 A1 | 1/2008 | Olmarker et al. |
| 2008/0044852 A1 | 2/2008 | Kanayinkal et al. |
| 2008/0064626 A1 | 3/2008 | Zanella |
| 2008/0145834 A1 | 6/2008 | Ho et al. |
| 2008/0164204 A1 | 7/2008 | Hatamian et al. |
| 2008/0173593 A1 | 7/2008 | Coull et al. |
| 2008/0193424 A1 | 8/2008 | Mckale et al. |
| 2008/0217263 A1 | 9/2008 | Higgins et al. |
| 2008/0217264 A1 | 9/2008 | Leach et al. |
| 2008/0217265 A1 | 9/2008 | Leach et al. |
| 2008/0268064 A1 | 10/2008 | Woodell-may |
| 2008/0269762 A1 | 10/2008 | Simon et al. |
| 2008/0283474 A1 | 11/2008 | Leach et al. |
| 2008/0300181 A1 | 12/2008 | Wang et al. |
| 2008/0306431 A1 | 12/2008 | Yoo |
| 2008/0318317 A1 | 12/2008 | Roche et al. |
| 2009/0014391 A1 | 1/2009 | Leach et al. |
| 2009/0018313 A1 | 1/2009 | Shanbrom |
| 2009/0047242 A1 | 2/2009 | Reinecke et al. |
| 2009/0101599 A1 | 4/2009 | Dorian et al. |
| 2009/0112146 A1 | 4/2009 | Wratten et al. |
| 2009/0181019 A1 | 7/2009 | Solinger |
| 2009/0191217 A1 | 7/2009 | De Wildt et al. |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2009/0263319 A1 | 10/2009 | Wohabrebbi et al. |
| 2009/0289014 A1 | 11/2009 | Hoeppner |
| 2009/0317439 A1 | 12/2009 | Turzi et al. |
| 2010/0008992 A1 | 1/2010 | Ichim |
| 2010/0015129 A1 | 1/2010 | Abramson et al. |
| 2010/0055087 A1 | 3/2010 | Higgins et al. |
| 2010/0125236 A1 | 5/2010 | Bare et al. |
| 2010/0140182 A1 | 6/2010 | Chapman et al. |
| 2010/0186676 A1 | 7/2010 | Van Der Berg |
| 2010/0198130 A1 | 8/2010 | Swift et al. |
| 2010/0206798 A1 | 8/2010 | Dorian et al. |
| 2010/0226909 A1 | 9/2010 | Hecker et al. |
| 2010/0256595 A1 | 10/2010 | Leach et al. |
| 2010/0323870 A1 | 12/2010 | Leach et al. |
| 2010/0324450 A1 | 12/2010 | Leach et al. |
| 2011/0014705 A1 | 1/2011 | Leach et al. |
| 2011/0020196 A1 | 1/2011 | Grippi et al. |
| 2011/0021334 A1 | 1/2011 | Leach et al. |
| 2011/0036786 A1 | 2/2011 | Ellsworth |
| 2011/0052561 A1 | 3/2011 | Hoeppner |
| 2011/0056893 A1 | 3/2011 | Leach et al. |
| 2011/0059082 A1 | 3/2011 | Germer et al. |
| 2011/0059083 A1 | 3/2011 | Aigner et al. |
| 2011/0059084 A1 | 3/2011 | Osterroth et al. |
| 2011/0065183 A1 | 3/2011 | Dorian et al. |
| 2011/0077596 A1 | 3/2011 | Higgins et al. |
| 2011/0129441 A1 | 6/2011 | Lentz |
| 2011/0147929 A1 | 6/2011 | Mihir et al. |
| 2011/0168193 A1 | 7/2011 | Leach et al. |
| 2011/0189172 A1 | 8/2011 | Solinger et al. |
| 2011/0192804 A1 | 8/2011 | Landrigan et al. |
| 2011/0251041 A1 | 10/2011 | Chavarria et al. |
| 2011/0268708 A1 | 11/2011 | Lin et al. |
| 2011/0300102 A1 | 12/2011 | Chung et al. |
| 2012/0010559 A1 | 1/2012 | Higgins et al. |
| 2012/0015796 A1 | 1/2012 | Leach et al. |
| 2012/0027746 A1 | 2/2012 | Dorian et al. |
| 2012/0093936 A1 | 4/2012 | Lindenberg et al. |
| 2012/0145652 A1 | 6/2012 | Leach et al. |
| 2012/0150086 A1 | 6/2012 | Cohen |
| 2012/0172836 A1 | 7/2012 | Higgins et al. |
| 2012/0228203 A1 | 9/2012 | Hecker et al. |
| 2013/0068676 A1 | 3/2013 | Leach et al. |
| 2013/0102452 A1 | 4/2013 | Leach et al. |
| 2013/0119549 A1 | 5/2013 | Cheng et al. |
| 2013/0178425 A1 | 7/2013 | Higgins et al. |
| 2013/0196425 A1 | 8/2013 | Dorian et al. |
| 2013/0259951 A1 | 10/2013 | O'Connell |
| 2013/0294983 A1 | 11/2013 | Dorian et al. |
| 2014/0051061 A1 | 2/2014 | Landrigan et al. |
| 2014/0054246 A1 | 2/2014 | Landrigan et al. |
| 2014/0091048 A1 | 4/2014 | Leach et al. |
| 2014/0242045 A1 | 8/2014 | Higgins et al. |
| 2014/0271587 A1 | 9/2014 | Landrigan et al. |
| 2014/0271588 A1 | 9/2014 | Landrigan et al. |
| 2014/0271589 A1 | 9/2014 | Matuska et al. |

(56) References Cited

U.S. PATENT DOCUMENTS

| | | |
|---|---|---|
| 2014/0271870 A1 | 9/2014 | O'Shaughnessey et al. |
| 2014/0274893 A1 | 9/2014 | Woodell-May et al. |
| 2014/0274894 A1 | 9/2014 | Leach et al. |
| 2014/0274895 A1 | 9/2014 | Binder et al. |
| 2014/0275497 A1 | 9/2014 | Leach et al. |
| 2014/0349388 A1 | 11/2014 | Dorian et al. |
| 2014/0356446 A1 | 12/2014 | Leach et al. |
| 2015/0141332 A1 | 5/2015 | Toler |
| 2015/0147300 A1 | 5/2015 | Woodell-May et al. |
| 2016/0000870 A1 | 1/2016 | Higgins et al. |
| 2016/0017010 A1 | 1/2016 | Higgins et al. |
| 2016/0074479 A1 | 3/2016 | Serbousek et al. |
| 2016/0136245 A1 | 5/2016 | Toler et al. |
| 2016/0166645 A1 | 6/2016 | Matuska et al. |
| 2017/0334960 A1 | 11/2017 | Higgins et al. |

FOREIGN PATENT DOCUMENTS

| | | |
|---|---|---|
| BR | 9103724 A | 3/1993 |
| CA | 1321138 C | 8/1993 |
| CA | 2182862 A1 | 6/1996 |
| CA | 2448415 A1 | 12/2002 |
| CA | 2772084 C | 10/2016 |
| CN | 1074709 A | 7/1993 |
| CN | 1321103 A | 11/2001 |
| CN | 1322146 A | 11/2001 |
| CN | 101056613 A | 10/2007 |
| CN | 102573790 A | 7/2012 |
| CN | 102596173 A | 7/2012 |
| CN | 103702729 A | 4/2014 |
| CN | 105209478 A | 12/2015 |
| CN | 105338990 A | 2/2016 |
| CN | 105339007 A | 2/2016 |
| CN | 105358161 A | 2/2016 |
| CN | 105358162 A | 2/2016 |
| CN | 105492015 A | 4/2016 |
| DE | 56103 C | 10/1960 |
| DE | 1443359 A1 | 11/1968 |
| DE | 4202667 C1 | 5/1993 |
| EP | 090997 A2 | 10/1983 |
| EP | 0102773 A2 | 3/1984 |
| EP | 0109374 A1 | 5/1984 |
| EP | 0142339 A1 | 5/1985 |
| EP | 0244834 A2 | 11/1987 |
| EP | 0253198 A1 | 1/1988 |
| EP | 0295771 A2 | 12/1988 |
| EP | 0417818 A1 | 3/1991 |
| EP | 0534178 A2 | 3/1993 |
| EP | 0592242 A1 | 4/1994 |
| EP | 1005910 A2 | 6/2000 |
| EP | 1006360 A2 | 6/2000 |
| EP | 1289618 A1 | 3/2003 |
| EP | 1427279 A1 | 6/2004 |
| EP | 1467746 A2 | 10/2004 |
| EP | 1509326 A2 | 3/2005 |
| EP | 1652538 A2 | 5/2006 |
| EP | 1670315 A2 | 6/2006 |
| EP | 1716901 A1 | 11/2006 |
| EP | 1406492 B1 | 12/2009 |
| EP | 2186877 A2 | 5/2010 |
| EP | 2259774 A | 12/2010 |
| EP | 2259774 B1 | 12/2012 |
| EP | 2567692 A1 | 3/2013 |
| EP | 2620139 A1 | 7/2013 |
| EP | 2968409 A1 | 1/2016 |
| EP | 2968412 A1 | 1/2016 |
| EP | 2470163 B1 | 9/2016 |
| GB | 854715 A | 11/1960 |
| JP | 60053845 A | 3/1985 |
| JP | 60250014 A | 3/1985 |
| JP | 2036872 A | 2/1990 |
| JP | 02071747 A | 3/1990 |
| JP | 02129224 A | 5/1990 |
| JP | 069684 A | 1/1994 |
| JP | 07101874 A | 4/1995 |
| JP | 1045616 A | 2/1998 |
| JP | 2000189407 A | 7/2000 |
| JP | 2000199760 A | 7/2000 |
| JP | 2001500472 A | 1/2001 |
| JP | 2001515088 A | 9/2001 |
| JP | 2002509529 A | 3/2002 |
| JP | 2002540818 A | 12/2002 |
| JP | 2003525696 A | 9/2003 |
| JP | 2004305439 A | 11/2004 |
| JP | 2005013783 A | 1/2005 |
| JP | 2005098704 A | 4/2005 |
| JP | 2005524451 A | 8/2005 |
| JP | 2006305365 A | 11/2006 |
| JP | 2006527025 A | 11/2006 |
| JP | 2007105186 A | 4/2007 |
| JP | 2007509601 A | 4/2007 |
| JP | 2008104789 A | 5/2008 |
| JP | 2009155234 A | 7/2009 |
| JP | 5551250 B2 | 7/2014 |
| WO | WO-8400905 A1 | 3/1984 |
| WO | WO-8802259 A1 | 4/1988 |
| WO | WO-9010031 A1 | 9/1990 |
| WO | WO-9108285 A1 | 6/1991 |
| WO | WO-9222312 A1 | 12/1992 |
| WO | WO-9305067 A | 3/1993 |
| WO | WO-9308904 A1 | 5/1993 |
| WO | WO-9407548 A1 | 4/1994 |
| WO | WO-9617871 A1 | 6/1996 |
| WO | WO-9824477 A1 | 6/1998 |
| WO | WO-1998024477 A1 | 6/1998 |
| WO | WO-9848938 A1 | 11/1998 |
| WO | WO-9905989 A2 | 2/1999 |
| WO | WO-9967277 A1 | 12/1999 |
| WO | WO-0046249 A1 | 8/2000 |
| WO | WO-0061256 A1 | 10/2000 |
| WO | WO-0074713 A1 | 12/2000 |
| WO | WO-0103756 A1 | 1/2001 |
| WO | WO-0183068 A1 | 11/2001 |
| WO | WO-0238610 A1 | 5/2002 |
| WO | WO-02060925 A1 | 8/2002 |
| WO | WO-02098566 A2 | 12/2002 |
| WO | WO-03015800 A1 | 2/2003 |
| WO | WO-03024215 A1 | 3/2003 |
| WO | WO-03053362 A2 | 7/2003 |
| WO | WO-03063799 A2 | 8/2003 |
| WO | WO-03080104 A2 | 10/2003 |
| WO | WO-03088905 A2 | 10/2003 |
| WO | WO-03092894 A2 | 11/2003 |
| WO | WO-03099412 A1 | 12/2003 |
| WO | WO-2004009207 A1 | 1/2004 |
| WO | WO-2004065564 A2 | 8/2004 |
| WO | WO-2004104553 A2 | 12/2004 |
| WO | WO-2005034843 A2 | 4/2005 |
| WO | WO-2006041406 A1 | 4/2006 |
| WO | WO-2006043972 A1 | 4/2006 |
| WO | WO 2007121538 A1 | 11/2007 |
| WO | WO-2007127834 A2 | 11/2007 |
| WO | WO-2007128973 A2 | 11/2007 |
| WO | WO-2007142908 A1 | 12/2007 |
| WO | WO-2008021237 A1 | 2/2008 |
| WO | WO-2008100442 A1 | 8/2008 |
| WO | WO-2008127639 A1 | 10/2008 |
| WO | WO-2008157733 A2 | 12/2008 |
| WO | WO-2009021257 A1 | 2/2009 |
| WO | WO-2009108890 A1 | 9/2009 |
| WO | WO-2009111338 A1 | 9/2009 |
| WO | WO 2010115190 A1 | 10/2010 |
| WO | WO-2010149164 A2 | 12/2010 |
| WO | WO-2011008836 A1 | 1/2011 |
| WO | WO-2011031524 A2 | 3/2011 |
| WO | WO-2011031524 A3 | 3/2011 |
| WO | WO-2011031525 A1 | 3/2011 |
| WO | WO-2011031553 A2 | 3/2011 |
| WO | WO-2011031553 A3 | 3/2011 |
| WO | WO-2012030593 A2 | 3/2012 |
| WO | WO-2012030593 A3 | 3/2012 |
| WO | WO-2014144505 A2 | 9/2014 |
| WO | WO-2014144505 A3 | 9/2014 |
| WO | WO-2014149266 A2 | 9/2014 |

(56) References Cited

FOREIGN PATENT DOCUMENTS

| WO | WO-2014149266 A3 | 9/2014 |
|---|---|---|
| WO | WO-2014149270 A1 | 9/2014 |
| WO | WO-2014149300 A1 | 9/2014 |
| WO | WO-2014149301 A1 | 9/2014 |
| WO | WO-2014149979 A1 | 9/2014 |
| WO | WO-2014150375 A2 | 9/2014 |
| WO | WO 2014150375 A3 | 9/2014 |
| WO | WO-2015099684 A1 | 7/2015 |

OTHER PUBLICATIONS

"A phase I safety study of combination treatment with pegylated soluble tumor necrosis factor receptor type I (PET STNF-RI) and anakinra (interleukin-1 receptor antagonist, IL-1RA) in patients with rheumatoid arthritis", Pious integrity, (Jun. 12, 2002), 1-1.
"U.S. Appl. No. 12/101,586, Final Office Action dated Feb. 3, 2011", 11 pgs.
"U.S. Appl. No. 12/101,586, Non Final Office Action dated Sep. 20, 2010", 12 pgs.
"U.S. Appl. No. 12/101,586, Notice of Allowance dated Mar. 24, 2011", 5 pgs.
"U.S. Appl. No. 12/101,594, Final Office Action dated Mar. 18, 2010", 8 pgs.
"U.S. Appl. No. 12/101,594, Non Final Office Action dated Oct. 16, 2009", 8 pgs.
"U.S. Appl. No. 12/101,594, Notice of Allowance dated May 27, 2010", 7 pgs.
"U.S. Appl. No. 12/394,723, Advisory Action dated Dec. 19, 2014", 3 pgs.
"U.S. Appl. No. 12/394,723, Appeal Brief filed Jun. 15, 2015", 42 pgs.
"U.S. Appl. No. 12/394,723, Decision on Pre-Appeal Brief dated Feb. 13, 2015", 2 pgs.
"U.S. Appl. No. 12/394,723, Examiner's Answer to Appeal Brief dated Sep. 9, 2015", 11 pgs.
"U.S. Appl. No. 12/394,723, Final Office Action dated Apr. 19, 2016", 13 pgs.
"U.S. Appl. No. 12/394,723, Final Office Action dated May 15, 2017", 14 pgs.
"U.S. Appl. No. 12/394,723, Final Office Action dated Jun. 26, 2012", 11 pgs.
"U.S. Appl. No. 12/394,723, Final Office Action dated Sep. 8, 2014", 8 pgs.
"U.S. Appl. No. 12/394,723, Non Final Office Action dated Feb. 7, 2002", 8 pgs.
"U.S. Appl. No. 12/394,723, Non Final Office Action dated Oct. 5, 2016", 16 pgs.
"U.S. Appl. No. 12/394,723, Non Final Office Action dated Oct. 31, 2011", 11 pgs.
"U.S. Appl. No. 12/394,723, Non Final Office Action dated Dec. 24, 2015", 9 Pgs.
"U.S. Appl. No. 12/394,723, Response filed Jan. 8, 2015 to Pre-Appeal Brief Request dated Dec. 19, 2014", 4 pgs.
"U.S. Appl. No. 12/394,723, Response filed Mar. 6, 2017 to Non Final Office Action dated Oct. 5, 2016", 25 pgs.
"U.S. Appl. No. 12/394,723, Response filed Mar. 24, 2016 to Non Final Office Action dated Dec. 24, 2015", 18 pgs.
"U.S. Appl. No. 12/394,723, Response filed Apr. 30, 2012 to Non Final Office Action dated Oct. 31, 2011", 16 pgs.
"U.S. Appl. No. 12/394,723, Response filed Jul. 23, 2014 to Non Final Office Action dated Feb. 7, 2014", 19 pgs.
"U.S. Appl. No. 12/394,723, Response filed Aug. 19, 2016 to Final Office Action dated Apr. 19, 2016", 23 pgs.
"U.S. Appl. No. 12/394,723, Response filed Aug. 22, 2011 to Restriction Requirement dated Jul. 20, 2011", 2 pgs.
"U.S. Appl. No. 12/394,723, Response filed Nov. 9, 2015 to Final Office Action dated Sep. 8, 2014", 19 pgs.
"U.S. Appl. No. 12/394,723, Response filed Dec. 10, 2014 to Final Office Action dated Sep. 8, 2014", 18 pgs.
"U.S. Appl. No. 12/394,723, Response filed Dec. 19, 2012 to Final Office Action dated Jun. 26, 2012", 16 pgs.
"U.S. Appl. No. 12/394,723, Restriction Requirement dated Jul. 20, 2011", 7 pgs.
"U.S. Appl. No. 12/549,015, Examiner Interview Summary dated Dec. 3, 2012", 3 pgs.
"U.S. Appl. No. 12/549,015, Final Office Action dated Aug. 16, 2012", 8 pgs.
"U.S. Appl. No. 12/549,015, Non Final Office Action dated Mar. 9, 2012", 8 pgs.
"U.S. Appl. No. 12/549,015, Notice of Allowance dated Feb. 3, 2014", 9 pgs.
"U.S. Appl. No. 12/549,015, Response filed Feb. 9, 2012 to Restriction Requirement dated Jan. 9, 2012", 2 pgs.
"U.S. Appl. No. 12/549,015, Response filed Jul. 6, 2012 to Non Final Office Action dated Mar. 9, 2012", 12 pgs.
"U.S. Appl. No. 12/549,015, Response filed Dec. 17, 2012 to Final Office Action dated Aug. 16, 2012", 17 pgs.
"U.S. Appl. No. 12/549,015, Restriction Requirement dated Jan. 9, 2012", 5 pgs.
"U.S. Appl. No. 12/549,116, Decision on Pre-Appeal Brief dated Feb. 5, 2015", 2 pgs.
"U.S. Appl. No. 12/549,116, Examiner Interview Summary dated Dec. 5, 2012", 3 pgs.
"U.S. Appl. No. 12/549,116, Final Office Action dated Jan. 4, 2016", 15 pgs.
"U.S. Appl. No. 12/549,116, Final Office Action dated Aug. 8, 2012", 20 pgs.
"U.S. Appl. No. 12/549,116, Final Office Action dated Oct. 8, 2014", 12 pgs.
"U.S. Appl. No. 12/549,116, Non Final Office Action dated Feb. 24, 2012", 16 pgs.
"U.S. Appl. No. 12/549,116, Non Final Office Action dated Jun. 4, 2015", 12 pgs.
"U.S. Appl. No. 12/549,116, Non Final Office Action dated Jun. 5, 2014", 15 pgs.
"U.S. Appl. No. 12/549,116, Non Final Office Action dated Oct. 10, 2016", 15 pgs.
"U.S. Appl. No. 12/549,116, Pre-Appeal Brief Request filed Jan. 8, 2015", 5 pgs.
"U.S. Appl. No. 12/549,116, Response filed Jan. 8, 2013 to Final Office Action dated Aug. 8, 2012", 14 pgs.
"U.S. Appl. No. 12/549,116, Response filed Jan. 13, 2012 to Restriction Requirement dated Dec. 13, 2011", 3 pgs.
"U.S. Appl. No. 12/549,116, Response filed Mar. 3, 2016 to Final Office Action dated Jan. 4, 2016", 11 pgs.
"U.S. Appl. No. 12/549,116, Response filed Jun. 25, 2012 to Non Final Office Action dated Feb. 24, 2012", 14 pgs.
"U.S. Appl. No. 12/549,116, Response filed Sep. 4, 2015 to Non Final Office Action dated Jun. 4, 2015", 9 pgs.
"U.S. Appl. No. 12/549,116, Response filed Sep. 5, 2014 to Non Final Office Action dated Jun. 5, 2014", 11 pgs.
"U.S. Appl. No. 12/549,116, Restriction Requirement dated Dec. 13, 2011", 6 pgs.
"U.S. Appl. No. 12/897,401, Non Final Office Action dated Nov. 16, 2010", 9 pgs.
"U.S. Appl. No. 12/897,401, Notice of Allowance dated Oct. 18, 2011", 6 pgs.
"U.S. Appl. No. 13/392,266, Advisory Action dated Jul. 31, 2014", 3 pgs.
"U.S. Appl. No. 13/392,266, Examiner Interview Summary dated Jul. 3, 2014", 3 pgs.
"U.S. Appl. No. 13/392,266, Examiner Interview Summary dated Nov. 15, 2013", 3 pgs.
"U.S. Appl. No. 13/392,266, Final Office Action dated May 8, 2014", 10 pgs.
"U.S. Appl. No. 13/392,266, Final Office Action dated Jul. 30, 2015", 12 pgs.
"U.S. Appl. No. 13/392,266, Final Office Action dated Sep. 3, 2013", 13 pgs.
"U.S. Appl. No. 13/392,266, Non Final Office Action dated Feb. 13, 2013", 12 pgs.

(56) References Cited

OTHER PUBLICATIONS

"U.S. Appl. No. 13/392,266, Non Final Office Action dated Feb. 26, 2015", 9 pgs.
"U.S. Appl. No. 13/392,266, Non Final Office Action dated Oct. 4, 2016", 21 pgs.
"U.S. Appl. No. 13/392,266, Non Final Office Action dated Dec. 31, 2013", 8 pgs.
"U.S. Appl. No. 13/392,266, Notice of Allowance dated Mar. 6, 2017", 8 pgs.
"U.S. Appl. No. 13/392,266, Preliminary Amendment filed Feb. 24, 2012", 3 pgs.
"U.S. Appl. No. 13/392,266, Preliminary Amendment filed Dec. 12, 2012", 7 pgs.
"U.S. Appl. No. 13/392,266, Response filed Jan. 4, 2017 to Non Final Office Action dated Oct. 4, 2016", 22 pgs.
"U.S. Appl. No. 13/392,266, Response filed Jan. 22, 2016 to Final Office Action dated Jul. 30, 2015", 24 pgs.
"U.S. Appl. No. 13/392,266, Response filed Apr. 18, 2014 to Non Final Office Action dated Dec. 31, 2013", 13 pgs.
"U.S. Appl. No. 13/392,266, Response filed Jul. 2, 2013 to Non Final Office Action dated Feb. 13, 2013", 15 pgs.
"U.S. Appl. No. 13/392,266, Response filed Jul. 8, 2015 to Non-Final Office Action dated Feb. 26, 2015", 13 pgs.
"U.S. Appl. No. 13/392,266, Response filed Jul. 11, 2014 to Final Office Action dated May 8, 2014", 14 pgs.
"U.S. Appl. No. 13/392,266, Response filed Dec. 3, 2013 to Final Office Action dated Sep. 3, 2013", 15 pgs.
"U.S. Appl. No. 13/392,266, Response filed Dec. 13, 2012 to Restriction Requirement dated Nov. 13, 2012", 5 pgs.
"U.S. Appl. No. 13/392,266, Restriction Requirement dated Nov. 13, 2012", 8 pgs.
"U.S. Appl. No. 13/782,421, Final Office Action dated Jan. 15, 2015", 30 pgs.
"U.S. Appl. No. 13/782,421, Non Final Office Action dated Jul. 3, 2014", 26 pgs.
"U.S. Appl. No. 13/782,421, Non Final Office Action dated Sep. 30, 2013", 30 pgs.
"U.S. Appl. No. 13/782,421, Notice of Allowance dated Apr. 27, 2015", 8 pgs.
"U.S. Appl. No. 13/782,421, Preliminary Amendment filed Mar. 1, 2013", 8 pgs.
"U.S. Appl. No. 13/782,421, Response filed Feb. 26, 2014 to Non Final Office Action dated Sep. 30, 2013", 21 pgs.
"U.S. Appl. No. 13/782,421, Response filed Apr. 15, 2015 to Final Office Action dated Jan. 15, 2015", 6 pgs.
"U.S. Appl. No. 13/782,421, Response filed Jul. 3, 2013 to Restriction Requirement dated Jun. 4, 2013", 2 pgs.
"U.S. Appl. No. 13/782,421, Response filed Oct. 3, 2014 to Non Final Office Action dated Jul. 3, 2014", 15 pgs.
"U.S. Appl. No. 13/782,421, Restriction Requirement dated Jun. 4, 2013", 6 pgs.
"U.S. Appl. No. 13/837,005, Advisory Action dated Dec. 2, 2016", 3 pgs.
"U.S. Appl. No. 13/837,005, Final Office Action dated Aug. 23, 2016", 9 pgs.
"U.S. Appl. No. 13/837,005, Final Office Action dated Dec. 5, 2014", 9 pgs.
"U.S. Appl. No. 13/837,005, Non Final Office Action dated Feb. 17, 2016", 13 pgs.
"U.S. Appl. No, 13/837,005, Non Final Office Action dated May 13, 2014", 10 pgs.
"U.S. Appl. No. 13/837,005, Non Final Office Action dated Jun. 9, 2015", 13 pgs.
"U.S. Appl. No. 13/837,005, Notice of Allowance dated May 18, 2017", 10 pgs.
"U.S. Appl. No. 13/837,005, Response filed Jan. 3, 2014 to Restriction Requirement dated Dec. 3, 2013", 4 pgs.
"U.S. Appl. No. 13/837,005, Response filed Mar. 5, 2015 to Final Office Action dated Dec. 5, 2014", 11 pgs.
"U.S. Appl. No. 13/837,005, Response filed May 17, 2016 to Non Final Office Action dated Feb. 17, 2016", 13 pgs.
"U.S. Appl. No. 13/837,005, Response filed Aug. 13, 2014 to Non Final Office Action dated May 13, 2014", 13 pgs.
"U.S. Appl. No. 13/837,005, Response filed Oct. 24, 2016 to Final Office Action dated Aug. 23, 2016", 9 pgs.
"U.S. Appl. No. 13/837,005, Response filed Nov. 9, 2015 to Non Final Office Action dated Jun. 9, 2015", 11 pgs.
"U.S. Appl. No. 13/837,005, Response filed Dec. 22, 2016 to Advisory Action dated Dec. 2, 2016", 10 pgs.
"U.S. Appl. No. 13/837,005, Restriction Requirement dated Dec. 3, 2013", 9 pgs.
"U.S. Appl. No. 13/837,480, Final Office Action dated May 4, 2017", 12 pgs.
"U.S. Appl. No. 13/837,480, Final Office Action dated May 23, 2016", 11 pgs.
"U.S. Appl. No. 13/837,480, Non Final Office Action dated Aug. 11, 2015", 10 pgs.
"U.S. Appl. No. 13/837,480, Non Final Office Action dated Sep. 13, 2016", 9 pgs.
"U.S. Appl. No. 13/837,480, Response filed Jan. 11, 2016 to Non Final Office Action dated Aug. 11, 2015", 14 pgs.
"U.S. Appl. No. 13/837,480, Response filed Jul. 25, 2016 to Final Office Action dated May 23, 2016", 13 pgs.
"U.S. Appl. No. 13/837,480, Response filed Aug. 7, 2017 to Final Office Action dated May 4, 2017", 12 pgs.
"U.S. Appl. No. 13/837,480, Response filed Nov. 5, 2014 to Restriction Requirement dated Sep. 16, 2014", 3 pgs.
"U.S. Appl. No. 13/837,480, Response filed Dec. 12, 2016 to Non Final Office Action dated Sep. 13, 2016", 13 pgs.
"U.S. Appl. No. 13/837,480, Restriction Requirement dated Sep. 16, 2014", 6 pgs.
"U.S. Appl. No. 13/839,280, Final Office Action dated Jan. 23, 2017", 14 pgs.
"U.S. Appl. No. 13/839,280, Final Office Action dated Apr. 10, 2015", 17 pgs.
"U.S. Appl. No. 13/839,280, Non Final Office Action dated Apr. 7, 2016", 16 pgs.
"U.S. Appl. No. 13/839,280, Non Final Office Action dated Jul. 17, 2014", 12 pgs.
"U.S. Appl. No. 13/839,280, Response filed Mar. 17, 2014 to Restriction Requirement dated Jan. 15, 2014", 5 pgs.
"U.S. Appl. No. 13/839,280, Response filed Apr. 24, 2017 to Final Office Action dated Jan. 23, 2017", 12 pgs.
"U.S. Appl. No. 13/839,280, Response filed Aug. 29, 2016 to Non Final Office Action dated Apr. 7, 2016", 15 pgs.
"U.S. Appl. No. 13/839,280, Response filed Oct. 12, 2015 to Final Office Action dated Apr. 10, 2015", 9 pgs.
"U.S. Appl. No. 13/839,280, Response filed Oct. 17, 2014 to Non Final Office Action dated Jul. 17, 2014", 19 pgs.
"U.S. Appl. No. 13/839,280, Restriction Requirement dated Jan. 15, 2014", 6 pgs.
"U.S. Appl. No. 13/840,129, Final Office Action dated Jun. 18, 2015", 9 pgs.
"U.S. Appl. No. 13/840,129, Non Final Office Action dated Oct. 23, 2014", 8 pgs.
"U.S. Appl. No. 13/840,129, Response filed Feb. 23, 2015 to Non Final Office Action dated Oct. 23, 2014", 15 pgs.
"U.S. Appl. No. 13/840,129, Restriction Requirement dated Mar. 14, 2014", 6 pgs.
"U.S. Appl. No, 13/840,562, Final Office Action dated Jan. 20, 2016", 14 pgs.
"U.S. Appl. No. 13/840,562, Non Final Office Action dated Apr. 24, 2015", 23 pgs.
"U.S. Appl. No. 13/840,562, Non Final Office Action dated Sep. 30, 2014", 19 pgs.
"U.S. Appl. No. 13/840,562, Response filed Mar. 21, 2014 to Restriction Requirement dated Jan. 23, 2014", 9 pgs.
"U.S. Appl. No. 13/840,562, Response filed Apr. 18, 2016 to Final Office Action dated Jan. 20, 2016", 18 pgs.
"U.S. Appl. No. 13/840,562, Response filed Jul. 29, 2015 to Non Final Office Action dated Apr. 24, 2015", 13 pgs.

(56) References Cited

OTHER PUBLICATIONS

"U.S. Appl. No. 13/840,562, Response filed Dec. 30, 2014 to Non Final Office Action dated Sep. 30, 2014", 17 pgs.
"U.S. Appl. No. 13/840,562, Restriction Requirement dated Jan. 23, 2014", 9 pgs.
"U.S. Appl. No. 13/841,083, Examiner Interview dated Feb. 24, 2017", 1 pg.
"U.S. Appl. No. 13/841,083, Examiner Summary dated Jan. 29, 2016", 1 pg.
"U.S. Appl. No. 13/841,083, Final Office Action dated Sep. 9, 2016", 10 pgs.
"U.S. Appl. No. 13/841,083, Non Final Office Action dated Jan. 29, 2016", 11 pgs.
"U.S. Appl. No. 13/841,083, Non Final Office Action dated Feb. 24, 2017", 12 pgs.
"U.S. Appl. No. 13/841,083, Non Final Office Action dated Jul. 15, 2015", 8 pgs.
"U.S. Appl. No. 13/841,083, Non Final Office Action dated Dec. 10, 2014", 12 pgs.
"U.S. Appl. No. 13/841,083, Notice of Allowance dated Sep. 7, 2017", 8 pgs.
"U.S. Appl. No. 13/841,083, Response filed Apr. 10, 2015 to Non Final Office Action dated Dec. 10, 2014", 17 pgs.
"U.S. Appl. No, 13/841,083, Response filed Apr. 28, 2016 to Non Final Office Action dated Jan. 29, 2016", 11 pgs.
"U.S. Appl. No. 13/841,083, Response filed May 24, 2017 to Non Final Office Action dated Feb. 24, 2017", 18 pgs.
"U.S. Appl. No. 13/841,083, Response filed Aug. 27, 2014 to Restriction Requirement dated Jul. 21, 2014", 3 pgs.
"U.S. Appl. No. 13/841,083, Response filed Oct. 13, 2015 to Non Final Office Action dated Jul. 15, 2015", 10 pgs.
"U.S. Appl. No. 13/841,083, Response filed Nov. 29, 2016 to Final Office Action dated Sep. 9, 2016", 12 pgs.
"U.S. Appl. No. 13/841,083, Restriction Requirement dated Jul. 21, 2014", 6 pgs.
"U.S. Appl. No. 13/841,083, Supplemental Amendment filed Aug. 29, 2017 to Non Final Office Action dated Feb. 24, 2017", 9 pgs.
"U.S. Appl. No. 13/841,103, Examiner Interview Summary dated Jun. 8, 2017", 1 pg.
"U.S. Appl. No, 13/841,103, Final Office Action dated Aug. 13, 2015", 13 pgs.
"U.S. Appl. No. 13/841,103, Final Office Action dated Dec. 14, 2016", 24 pgs.
"U.S. Appl. No. 13/841,103, Non Final Office Action dated Jun. 7, 2016", 16 pgs.
"U.S. Appl. No. 13/841,103, Non Final Office Action dated Jun. 8, 2017", 13 pgs.
"U.S. Appl. No. 13/841,103, Non Final Office Action dated Dec. 4, 2014", 10 pgs.
"U.S. Appl. No. 13/841,103, Notice of Allowance dated Oct. 11, 2017", 8 pgs.
"U.S. Appl. No. 13/841,103, Response filed Jan. 13, 2016 to Final Office Action dated Aug. 13, 2015", 11 pg.
"U.S. Appl. No. 13/841,103, Response filed Mar. 13, 2017 to Final Office Action dated Dec. 14, 2016", 14 pgs.
"U.S. Appl. No. 13/841,103, Response filed Apr. 18, 2016 to Restriction Requirement dated Feb. 19, 2016", 8 pgs.
"U.S. Appl. No. 13/841,103, Response filed May 4, 2015 to Non Final Office Action dated Dec. 4, 2014", 18 pgs.
"U.S. Appl. No. 13/841,103, Response filed Aug. 27, 2014 to Restriction Requirement dated Jul. 21, 2014", 3 pgs.
"U.S. Appl. No. 13/841,103, Response filed Aug. 31, 2016 to Non Final Office Action dated Jun. 7, 2016", 15 pgs.
"U.S. Appl. No. 13/841,103, Response filed Sep. 8, 2017 to Non Final Office Action dated Jun. 8, 2017", 12 pgs.
"U.S. Appl. No. 13/841,103, Restriction Requirement dated Feb. 19, 2016", 7 pgs.
"U.S. Appl. No. 13/841,103, Restriction Requirement dated Jul. 21, 2014", 6 pgs.
"U.S. Appl. No. 13/841,103, Supplemental Preliminary Amendment filed Sep. 26, 2017", 7 pgs.
"U.S. Appl. No. 14/050,950, Final Office Action dated Jun. 17, 2016", 9 pgs.
"U.S. Appl. No. 14/050,950, Non Final Office Action dated Nov. 19, 2015", 13 pgs.
"U.S. Appl. No. 14/050,950, Notice of Allowance dated Oct. 6, 2016", 12 pgs.
"U.S. Appl. No. 14/050,950, Response filed Feb. 19, 2016 to Non Final Office Action dated Nov. 19, 2015", 11 pgs.
"U.S. Appl. No. 14/050,950, Response filed Jun. 23, 2015 to Restriction Requirement dated Apr. 23, 2015", 1 pgs.
"U.S. Appl. No. 14/050,950, Response filed Aug. 17, 2016 to Final Office Action dated Jun. 17, 2016", 8 pgs.
"U.S. Appl. No. 14/050,950, Restriction Requirement dated Apr. 23, 2015", 7 pgs.
"U.S. Appl. No. 14/271,722, Notice of Allowance dated Jan. 25, 2016", 13 pgs.
"U.S. Appl. No. 14/271,722, Preliminary Amendment filed May 7, 2014", 9 pgs.
"U.S. Appl. No. 14/803,414, Non Final Office Action dated Apr. 19, 2017", 35 pgs.
"U.S. Appl. No. 14/803,414, Preliminary Amendment filed Sep. 16, 2015", 7 pgs.
"U.S. Appl. No. 14/803,414, Response filed Jul. 10, 2017 to Non Final Office Action dated Apr. 19, 2017", 15 pgs.
"U.S. Appl. No. 14/803,414, Response filed Dec. 19, 2016 to Restriction Requirement dated Oct. 20, 2016", 7 pgs.
"U.S. Appl. No. 14/803,414, Restriction Requirement dated Oct. 20, 2016", 7 pgs.
"U.S. Appl. No. 14/803,414, Supplemental Preliminary Amendment Filed Feb. 3, 2016", 8 pgs.
"U.S. Appl. No. 14/808,828, Amendment Under 37 C.F.R. § 1.312 Filed", 6 pgs.
"U.S. Appl. No. 14/808,828, Non Final Office Action dated Dec. 8, 2016", 10 pgs.
"U.S. Appl. No. 14/808,828, Notice of Allowance dated May 19, 2017", 9 pgs.
"U.S. Appl. No. 14/808,828, Preliminary Amendment filed Jul. 24, 2015", 12 pgs.
"U.S. Appl. No. 14/808,828, PTO Response to Rule 312 Communication dated Jun. 8, 2017", 2 pgs.
"U.S. Appl. No. 14/808,828, Response filed Mar. 8, 2017 to Non Final Office Action dated Dec. 8, 2016", 9 pgs.
"U.S. Appl. No, 14/808,828, Response filed Oct. 3, 2016 to Restriction Requirement dated Aug. 2, 2016", 7 pgs.
"U.S. Appl. No. 14/808,828, Restriction Requirement dated Aug. 2, 2016", 6 pgs.
"U.S. Appl. No. 14/808,828, Supplemental Preliminary Amendment filed Jul. 27, 2015", 10 pgs.
"U.S. Appl. No. 14/808,828, Supplemental Preliminary Amendment filed Oct. 6, 2015", 7 pgs.
"U.S. Appl. No. 14/830,977, Final Office Action dated Oct. 20, 2016", 12 pgs.
"U.S. Appl. No. 14/830,977, Non Final Office Action dated Apr. 13, 2016", 16 pgs.
"U.S. Appl. No. 14/830,977, Non Final Office Action dated Aug. 7, 2017", 12 pgs.
"U.S. Appl. No. 14/830,977, Response filed Jan. 20, 2017 to Final Office Action dated Oct. 20, 2016", 27 pgs.
"U.S. Appl. No. 14/830,977, Response filed Jul. 13, 2016 to Non Final Office Action dated Apr. 13, 2016", 10 pgs.
"U.S. Appl. No. 14/841,086, Examiners Interview Summary dated Nov. 7, 2016", 3 pgs.
"U.S. Appl. No. 14/973,913, Preliminary Amendment filed Mar. 2, 2016", 10 pgs.
"Application Serial No. 14709014.6, Response filed Feb. 27, 2017 to Non Final Office Action dated Oct. 20, 2016", 22 pgs.
"U.S. Appl. No. 15/616,548, Preliminary Amendment filed Jun. 7, 2017", 6 pgs.
"U.S. Appl. No. 15/616,548, Supplemental Preliminary Amendment Filed Aug. 17, 2017", 6 pgs.

(56) References Cited

OTHER PUBLICATIONS

"U.S. Appl. No. 13/840,129, Response filed May 14, 2014 to Restriction Requirement dated Mar. 14, 2014", 3 pgs.
"Arthritis", Mayo Clinic, (Jan. 22, 2013), 1-5.
"Arthritis", [Online]. Retrieved from the Internet: Wayback Machine <URL:http://www.mayoclinic.org/diseases-conditions/arthritis/basics/treatment/con-20034095 >, (2014), 5 pgs.
"Australian Application Serial No. 2010292553, First Examiner Report dated Feb. 7, 2014", 3 pgs.
"Australian Application Serial No. 2011296356, Amendment filed Jun. 3, 2014", 21 pgs.
"Australian Application Serial No. 2011296356, First Examiner Report dated Jun. 10, 2014", 7 pgs.
"Australian Application Serial No. 2011296356, Response filed Jun. 11, 2015 to First Examiner Report dated Jun. 10, 2014", 20 pgs.
"Bio-Gel P Polyacrylamide Gel", Instruction Manual, downloaded on Jun. 20, 2012 from [Online] retrieved from internet: <www.bio-rad.com/webmaster/pdfs/9154_Bio-Gel P.pdf>, 1-14.
"Bio-Rad Laboratories. Bio-Gel P Polyacrylamide Gel Instruction Manual", [Online]. Retrieved from the Internet: <www.bio-rad.com/webmaster/pdfs/9154 Bio-Gel P.pdf>, (Jun. 20, 2012), 14 pgs.
"BioCUE™ Platelet Concentration System", (Jun. 2010), 2 pgs.
"Canadian Application No. 2,810,202, Response filed Jan. 26, 2017 to Non Final Office Action dated Aug. 11, 2016", 8 pgs.
"Canadian Application Serial No. 2,772,067, Office Action dated Jan. 8, 2015", 3 pgs.
"Canadian Application Serial No. 2,772,067, Office Action dated Nov. 24, 2015", 3 pgs.
"Canadian Application Serial No. 2,772,067, Response filed Mar. 1, 2016 to Office Action dated Nov. 24, 2015", 7 pgs.
"Canadian Application Serial No. 2,772,067, Response filed Jul. 8, 2015 to Office Action dated Jan. 8, 2015", 24 pgs.
"Canadian Application Serial No. 2,772,069, Office Action dated Jul. 20, 2016", 5 pgs.
"Canadian Application Serial No. 2,772,069, Office Action dated Sep. 16, 2015", 3 pgs.
"Canadian Application Serial No. 2,772,084, Office Action dated Jun. 11, 2015", 3 pgs.
"Canadian Application Serial No. 2,810,202, Office Action dated Jul. 2, 2015", 5 pgs.
"Canadian Application Serial No. 2,810,202, Office Action dated Aug. 11, 2016", 4 pgs.
"Canadian Application Serial No. 2,810,202, Response filed Dec. 30, 2015 to Office Action dated Jul. 2, 2015", 19 pgs.
"Canadian Application Serial No. 2,810,202, Voluntary Amendment filed Jan. 13, 2014", 12 pgs.
"Canadian Application Serial No. 2,905,552, Voluntary Amendment filed Sep. 11, 2015".
"Canadian Application Serial No. 2,906,310, Voluntary Amendment filed Sep. 14, 2015", 2 pgs.
"Caps for Corning® and Costar® Plastic Labware", Technical Bulletin, (Dec. 2008), 2 pgs.
"Cell Isolation Techniques, Methods and Materials, Working with Enzymes", Worthington Biochemical Corp, (2004), 9 pgs.
"Cell Isolation Theory, Tissue Types", Worthington Biochemical Corp, (2004), 5 pgs.
"Centrifuge Tubes", Corning Costar, (1996/1997), 76-77.
"Chinese Application Serial No. 201080019707.7, Office Action dated Jun. 30, 2014", in English, 7 pgs.
"Chinese Application Serial No. 2010800428565, Non Final Office Action dated Jan. 22, 2013", W/ English Translation, 10 pgs.
"Chinese Application Serial No. 2010800428565, Non Final Office Action dated Feb. 14, 2014", W/ English Translation, 5 pgs.
"Chinese Application Serial No. 2010800428565, Non Final Office Action dated dated Sep. 10, 2013", W/ English Translation, 10 pgs.
"Chinese Application Serial No. 2010800428565, Response filed Apr. 29, 2014 to Non Final Office Action dated Feb. 14, 2014", W/ English Claims, 7 pgs.
"Chinese Application Serial No. 2010800428565, Response filed Aug. 6, 2013 to Non Final Office Action dated Jan. 22, 2013", W/ English Claims, 9 pgs.
"Chinese Application Serial No. 2010800428565,Response filed Nov. 25, 2013 to Non Final Office Action dated Sep. 10, 2013", W/ English Claims, 10 pgs.
"Chinese Application Serial No. 2010800447744, Decision on rejection dated Nov. 15, 2014", W/ English Translation, 10 pgs.
"Chinese Application Serial No. 2010800447744, Notification of Reexamination dated Feb. 23, 2016", W/ English Translation, 9 pgs.
"Chinese Application Serial No. 2010800447744, Office Action dated Jan. 31, 2013", W/ English Translation, 12 pgs.
"Chinese Application Serial No. 2010800447744, Office Action dated Apr. 30, 2014", W/ Machine Translation, 13 pgs.
"Chinese Application Serial No. 2010800447744, Office Action dated Oct. 22, 2013", W/ English Translation, 10 pgs.
"Chinese Application Serial No. 2010800447744, Response filed Jan. 6, 2014 to Office Action dated Oct. 22, 2013", with English translation of claims, 27 pgs.
"Chinese Application Serial No. 2010800447744, Response filed Feb. 19, 2015 to Decision on rejection dated Nov. 15, 2014", W/ English Translation, 13 pgs.
"Chinese Application Serial No. 2010800447744, Response filed Apr. 11, 2016 to Notification of Reexamination dated Feb. 23, 2016", W/ English Claims, 23 pgs.
"Chinese Application Serial No. 2010800447744, Response filed Jun. 17, 2013 to Office Action dated Jan. 31, 2013", W/ Machine Translation, 11 pgs.
"Chinese Application Serial No. 2010800447744, Response filed Jul. 15, 2014 to Office Action dated Apr. 30, 2014", with English translation of claims, 25 pgs.
"Chinese Application Serial No. 2011800457327, Office Action dated Mar. 26, 2015", W. Machine Translation, 18 pgs.
"Chinese Application Serial No. 2011800457327, Office Action dated Jul. 16, 2014", W/ Machine Translation, 16 pgs.
"Chinese Application Serial No. 2011800457327, Office Action dated Sep. 28, 2015", W/ Machine Translation, 14 pgs.
"Chinese Application Serial No. 2011800457327, Response filed Jun. 10, 2015 to Office Action dated Mar. 26, 2015", W/ English Claims, 22 pgs.
"Chinese Application Serial No. 2011800457327, Response filed Dec. 1, 2014 to Office Action dated Jul. 16, 2014", W/ English Claims, 19 pgs.
"Chinese Application Serial No. 201280030026.X, Office Action dated Nov. 21, 2014", w/ English Translation, 27 pgs.
"Chinese Application Serial No. 201480027178.3, Voluntary Amendment filed Jul. 15, 2016", (W/ English Translation of Claims), 35 pgs.
"Chinese Application Serial No. 201480027408.6, Voluntary Amendment dated Jun. 8, 2016", W/ English Claims, 50 pgs.
"Chinese Application Serial No. 201480027541.1, Voluntary Amendment dated May 5, 2016", w/ English Claims, 15 pgs.
"Chinese Application Serial No. 201480027655.6, Office Action dated May 15, 2017", (W/ English Translation), 11 pgs.
"Clotalyst® Autologous Clotting Factor", "Would you like to have an autologous thrombin for rapid clotting and haemostasis?" Biomet Biologics, (Jan. 2007), 16 pgs.
"Corning® 15 and 50 ml Centrifuge Tubes", Life Sciences. Corning Incorporated., (Jun. 2005), 2 pgs.
"Cytori Celution Cell Concentrate Device", Exhibit 14, 501(k) Summary, FDA approval K060482, (Sep. 28, 2006), 7 pgs.
"European Application No. 09715775.4, Non Final Office Action dated Apr. 26, 2011", 5 pgs.
"European Application No. 09715775.4, Preliminary Amendment filed Sep. 22, 2010", 9 pgs.
"European Application No. 09715775,4,Response filed Oct. 12, 2011 to Non Final Office Action dated Apr. 26, 2011", 20 pgs.
"European Application No. 09715775.4,Supplemental Preliminary Amendment filed Nov. 17, 2010", 12 pgs.
"European Application No. 14707909.9, Summons to Attend Oral Proceedings dated Aug. 10, 2017", 7 pgs.
"European Application No. 15184504.7, Response filed Jan. 25, 2017 to Non Final Office Action dated Sep. 16, 2016", 10 pgs.

(56) References Cited

OTHER PUBLICATIONS

"European Application Serial No. 10712677.3, Examination Notification Art. 94(3) dated Jun. 5, 2013", 5 pgs.
"European Application Serial No. 10749582.2, Communication Pursuant to Article 94(3) EPC dated May 10, 2016", 4 pgs.
"European Application Serial No. 10749582.2, Communication Pursuant to Article 94(3) EPC dated Sep. 10, 2013", 5 pgs.
"European Application Serial No. 10749582.2, Examination Notification Art. 94(3) dated Dec. 8, 2014", 7 pgs.
"European Application Serial No. 10749582.2, Response filed Jan. 3, 2014 to Communication Pursuant to Article 94(3) EPC dated Sep. 10, 2013", 12 pgs.
"European Application Serial No. 10749582.2, Response filed Apr. 1, 2015 to Communication Pursuant to Article 94(3) EPC dated Dec. 8, 2014", 14 pgs.
"European Application Serial No. 10749582.2, Response filed Aug. 26, 2016 to Communication Pursuant to Article 94(3) EPC dated May 10, 2016", 13 pgs.
"European Application Serial No. 10749582.2, Response filed Sep. 28, 2012 to Communication pursuant to Rules 161(2) and 162 EPC dated Apr. 3, 2012", 19 pgs.
"European Application Serial No. 10754379.5, Examination Notification Art, 94(3) dated Aug. 16, 2013", 5 pgs.
"European Application Serial No. 10754379.5, Examination Notification Art. 94(3) dated Dec. 15, 2014", 4 pgs.
"European Application Serial No. 10754379.5, Office Action dated Apr. 3, 2012", 2 pgs.
"European Application Serial No. 10754379.5, Response filed Feb. 17, 2014 to Examination Notification Art, 94(3) dated Aug. 16, 2013", 13 pgs.
"European Application Serial No. 10754379.5, Response filed Apr. 13, 2015 to Examination Notification Art. 94(3) dated Dec. 15, 2014", 8 pgs.
"European Application Serial No. 10754379.5, Response filed Sep. 28, 2012 to Office Action dated Apr. 3, 2012", 11 pgs.
"European Application Serial No. 10754613.7, Communication Pursuant to Article 94(3) EPC dated Sep. 16, 2013", 4 pgs.
"European Application Serial No. 10754613.7, Communication Pursuant to Article 94(3) EPC dated Nov. 13, 2015", 4 pgs.
"European Application Serial No. 10754613.7, Non Final Office Action dated Feb. 7, 2017", 5 pgs.
"European Application Serial No. 10754613.7, Response filed Mar. 14, 2014 to Communication Pursuant to Article 94(3) EPC dated Sep. 16, 2013", 15 pgs.
"European Application Serial No. 10754613.7, Response filed Mar. 15, 2016 to Communication Pursuant to Article 94(3) EPC dated Nov. 13, 2015", 26 pgs.
"European Application Serial No. 10754613.7, Response filed Aug. 16, 2017 to Non Final Office Action dated Feb. 7, 2017", 20 pgs.
"European Application Serial No. 10754613.7, Response filed Oct. 1, 2012 to Communication pursuant to Rules 161(1) and 162 EPC dated Mar. 4, 2012", 15 pgs.
"European Application Serial No. 11754786.9, Communication Pursuant to Article 94(3) EPC dated Feb. 19, 2014", 4 pgs.
"European Application Serial No. 11754786.9, Examination Notification Art. 94(3) dated Oct. 8, 2014", 5 pgs.
"European Application Serial No. 11754786.9, Grounds for the decision dated Oct. 13, 2015", 7 pgs.
"European Application Serial No. 11754786.9, Response filed Feb. 6, 2015 to Communication Pursuant to Article 94(3) EPC dated Oct. 8, 2014", 9 pgs.
"European Application Serial No. 11754786.9, Response filed Aug. 13, 2014 to Communication Pursuant to Article 94(3) EPC dated Feb. 19, 2014", 10 pgs.
"European Application Serial No. 11754786.9, Response filed Nov. 4, 2013 to Communication pursuant to Rules 161(1) and 162 EPC dated Apr. 24, 2013", 21 pgs.
"European Application Serial No. 11754786.9, Summons to Attend Oral Proceedings dated Mar. 10, 2015", 3 pgs.
"European Application Serial No. 12195882.1, Extended European Search Report dated Jan. 31, 2013", 5 pgs.
"European Application Serial No. 12195882.1, Non Final Office Action dated Jun. 30, 2014", 4 pgs.
"European Application Serial No. 12195882.1, Response filed Sep. 11, 2013 to Extended European Search Report dated Jan. 31, 2013", 16 pgs.
"European Application Serial No. 12195882.1, Response filed Oct. 29, 2014 to Non Final Office Action dated Jun. 30, 2014", 18 pgs.
"European Application Serial No. 13165543.3, Extended European Search Report dated Jul. 1, 2013", 6 pgs.
"European Application Serial No. 13165543.3, Non Final Office Action dated Jun. 27, 2014", 5 pgs.
"European Application Serial No. 13165543.3, Response filed Jan. 14, 2014 to Extended European Search Report dated Jul. 1, 2013", 11 pgs.
"European Application Serial No. 13165543.3, Response filed Oct. 24, 2014 to Non Final Office Action dated Jun. 27, 2014", 6 pgs.
"European Application Serial No. 14707069.2, Communication Pursuant to Article 94(3) EPC dated Nov. 15, 2016", 7 pgs.
"European Application Serial No. 14707069.2, Response Filed Mar. 27, 2017 to Communication Pursuant to Article 94(3) EPC dated Nov. 15, 2016", 16 pgs.
"European Application Serial No. 14707069.2, Response filed May 23, 2016 to Communication pursuant to Rules 161(1) and 162 EPC dated Nov. 12, 2015", 12 pgs.
"European Application Serial No. 14707909.9, Communication Pursuant to Article 94(3) EPC dated Jul. 22, 2016", 9 pgs.
"European Application Serial No. 14707909.9, Communication Pursuant to Article 94(3) EPC dated Dec. 16, 2016", 5 pgs.
"European Application Serial No. 14707909.9, Preliminary Amendment filed on May 13, 2016", 14 pgs.
"European Application Serial No. 14707909.9, Response filed Apr. 26, 2017 to Communication Pursuant to Article 94(3) EPC dated Dec. 16, 2016", 25 pgs.
"European Application Serial No. 14707909.9, Response filed Dec. 6, 2016 to Communication Pursuant to Article 94(3) EPC dated Jul. 22, 2016", 11 pgs.
"European Application Serial No. 14709014.6, Communication Pursuant to Article 94(3) EPC dated Oct. 20, 2016", 12 pgs.
"European Application Serial No. 14709014.6, Office Action dated Nov. 19, 2015", 2 pgs.
"European Application Serial No. 14709014.6, Response filed May 27, 2016 to Office Action dated Nov. 19, 2015", 15 pgs.
"European Application Serial No. 14709014.6, Summons to Attend Oral Proceedings dated Jun. 7, 2017", 8 pgs.
"European Application Serial No. 14709803.2, Response filed May 16, 2016 to Communication pursuant to Rules 161(1) and 162 EPC dated Nov. 5, 2015", 14 pgs.
"European Application Serial No. 14714491.9, Communication Pursuant to Article 94(3) EPC dated Feb. 28, 2017", 9 pgs.
"European Application Serial No. 14714491.9, Non Final Office Action dated Mar. 6, 2017", 9 pgs.
"European Application Serial No. 14714491.9, Response filed Aug. 1, 2016 to Communication Pursuant to Rules 161 and 162 EPC dated Jan. 21, 2016", 11 pgs.
"European Application Serial No. 14724817.3, Office Action dated Jun. 29, 2017", 5 pgs.
"European Application Serial No. 14724817.3, Office Action dated Oct. 27, 2015", 2 pgs.
"European Application Serial No. 14724817.3, Response filed May 6, 2016 to Communication rsuant to Rules 161(1) and 162 EPC dated Oct. 27, 2015", 13 pgs.
"European Application Serial No. 14729994.5, Response filed May 9, 2016 to Communication pursuant to Rules 161(1) and 162 EPC dated Oct. 30, 2015", 14 pgs.
"European Application Serial No. 15184504.7, Communication Pursuant to Article 94(3) EPC dated Feb. 13, 2016", 5 pgs.
"European Application Serial No. 15184504.7, Communication Pursuant to Article 94(3) EPC dated Feb. 13, 2017", 6 pgs.
"European Application Serial No. 15184504.7, Communication Pursuant to Article 94(3) EPC dated Jul. 28, 2017", 13 pgs.

(56) References Cited

OTHER PUBLICATIONS

"European Application Serial No. 15184504.7, Communication Pursuant to Article 94(3) EPC dated Sep. 16, 2016", 5 pgs.
"European Application Serial No. 15184504.7, Extended European Search Report dated Oct. 20, 2015", 7 pgs.
"European Application Serial No. 15184504.7, Response filed Jun. 12, 2017 to Communication Pursuant to Article 94(3) EPC dated Feb. 13, 2017", 10 pgs.
"Fibrostik™ Plasma Concentrator", Attention Operating Surgeon, Cell Factor Technologies, (Jul. 2003), 2 pgs.
"Frequently Asked Questions, 1. Kits, 2. Enzymes", Worthington Biochemical Corp, (2003), 3 pgs.
"GPS® II Platelet Concentrate System: The New Gold Standard", Product Brochure, (Sep. 2006), 14 pgs.
"GPS® II System, Gravitational Platelet Separation System", User Manual-Cell Factor Technologies, Inc., [Online]. Retrieved from the Internet: <http://www.cellfactortech.com/global_products.cfm,>, (Sep. 16, 2005), 13 pgs.
"GPS® II System, Gravitational Platelet Separation System, Accelerating the Body's Natural Healing Process", Cell Factor Technologies, Inc., [Online] retrieved form the internet: <http://www.cellfactortech.com/global_products.cfm>, printed Sep. 16, 2005, (2005), 16 pgs.
"GPS® III Platelet Separation System, Leadership through Technology", Biomet Biologics, Inc, (Jul. 2007), 8 pgs.
"GPS® Platelet Concentrate System", Cell Factor Technologies, Inc Biomet Orthopaedics, Inc., (Feb. 29, 2004), 9 pgs.
"Hemocor HPH® Hemoconcentrator", Minntech® Filtration Technologies Group, Minntech Corporation (2004), <http://www.minntech.com/ftg/products/hph/index.html>, (Jul. 15, 2004), 2 pgs.
"Increasing bone graft bioactivity through reproducible concentrations of natural growth factors", Symphony II Platelet Concentrate System/PCS brochure, (Jan. 2003), 8 pgs.
"International Application Serial No. PCT/US2003/016506, International Search Report dated Oct. 13, 2003", 2 pgs.
"International Application Serial No. PCT/US2007/012587, International Search Report dated Nov. 6, 2007", 2 pgs.
"International Application Serial No. PCT/US2008/004687, International Preliminary Report on Patentability dated Aug. 13, 2009", 19 pgs.
"International Application Serial No. PCT/US2008/004687, International Search Report dated Jul. 2, 2008", 3 pgs.
"International Application Serial No. PCT/US2008/004687, Written Opinion dated Mar. 17, 2009", 5 pgs.
"International Application Serial No. PCT/US2008/004687, Written Opinion dated Jul. 2, 2008", 5 pgs.
"International Application Serial No. PCT/US2009/035541, International Preliminary Report on Patentability dated Aug. 3, 2010", 8 pgs.
"International Application Serial No. PCT/US2009/035541, International Search Report dated Jun. 16, 2009", 3 pgs.
"International Application Serial No. PCT/US2009/035541, Written Opinon dated Jun. 16, 2009", 7 pgs.
"International Application Serial No. PCT/US2009/035564, International Preliminary Examination Report dated Aug. 31, 2010", 6 pgs.
"International Application Serial No. PCT/US2009/035564, International Search Report dated Jul. 3, 2009", 3 pgs.
"International Application Serial No. PCT/US2009/035564, Written Opinion dated Jul. 3, 2009", 5 pgs.
"International Application Serial No. PCT/US2010/029957, International Preliminary Report on Patentability dated Oct. 13, 2011", 10 pgs.
"International Application Serial No. PCT/US2010/029957, International Search Report dated Jul. 30, 2010", 6 pgs.
"International Application Serial No. PCT/US2010/029957, Written Opinion dated Jul. 30, 2010", 9 pgs.
"International Application Serial No. PCT/US2010/041942, International Preliminary Report on Patentability dated Jan. 26, 2012", 9 pgs.
"International Application Serial No. PCT/US2010/041942, International Search Report dated Oct. 8, 2010", 3 pgs.
"International Application Serial No. PCT/US2010/041942, Written Opinion dated Oct. 8, 2010", 8 pgs.
"International Application Serial No. PCT/US2010/046821, International Preliminary Report on Patentability dated Mar. 8, 2012", 6 pgs.
"International Application Serial No. PCT/US2010/046821, International Search Report dated Jul. 22, 2011", 4 pgs.
"International Application Serial No. PCT/US2010/046821, Written Opinion dated Jul. 22, 2011", 4 pgs.
"International Application Serial No. PCT/US2011/031954, International Search Report dated Aug. 9, 2011", 4 pgs.
"International Application Serial No. PCT/US2011/031954, Written Opinion dated Aug. 9, 2011", 9 pgs.
"International Application Serial No. PCT/US2011/045290, International Search Report dated Nov. 7, 2011", 5 pgs.
"International Application Serial No. PCT/US2011/045290, Written Opinion dated Nov. 7, 2011", 5 pgs.
"International Application Serial No. PCT/US2012/034104, International Preliminary Report on Patentability dated Oct. 31, 2013", 7 pgs.
"International Application Serial No. PCT/US2012/034104, International Search Report dated Oct. 29, 2012", 5 pgs.
"International Application Serial No. PCT/US2012/034104, Written Opinion dated Oct. 29. 2012", 6 pgs.
"International Application Serial No. PCT/US2013/056793, International Preliminary Report on Patentability dated Mar. 12, 2015", 8 pgs.
"International Application Serial No. PCT/US2013/056793, International Search Report dated Dec. 5, 2013", 3 pgs.
"International Application Serial No. PCT/US2013/056793, Written Opinion dated Dec. 5, 2013", 6 pgs.
"International Application Serial No. PCT/US2014/016384, International Preliminary Report on Patentability dated Sep. 24, 2015", 16 pgs.
"International Application Serial No. PCT/US2014/016384, International Search Report dated Oct. 9, 2014", 10 pgs.
"International Application Serial No. PCT/US2014/016384, Written Opinion dated Oct. 9, 2014", 14 pgs.
"International Application Serial No. PCT/US2014/016421, International Preliminary Report on Patentability dated Sep. 24, 2015", 16 pgs.
"International Application Serial No. PCT/US2014/016421, International Search Report dated Jul. 24, 2014", 8 pgs.
"International Application Serial No. PCT/US2014/016421, Written Opinion dated Jul. 24, 2014", 14 pgs.
"International Application Serial No. PCT/US2014/016895, International Preliminary Report on Patentability dated Sep. 24, 2015", 16 pgs.
"International Application Serial No. PCT/US2014/016895, International Search Report dated Jul. 24, 2014", 9 pgs.
"International Application Serial No. PCT/US2014/016895, Written Opinion dated Jul. 24, 2014", 14 pgs.
"International Application Serial No. PCT/US2014/016900, International Preliminary Report on Patentability dated Sep. 24, 2015", 9 pgs.
"International Application Serial No. PCT/US2014/016900, International Search Report dated May 12, 2014", 5 pgs.
"International Application Serial No. PCT/US2014/016900, Written Opinion dated May 12, 2014", 8 pgs.
"International Application Serial No. PCT/US2014/021707, International Preliminary Report on Patentability dated Sep. 24, 2015", 16 pgs.
"International Application Serial No. PCT/US2014/021707, International Search Report dated Jul. 24, 2014", 8 pgs.
"International Application Serial No. PCT/US2014/021707, Written Opinion dated Jul. 24, 2014", 14 pgs.
"International Application Serial No. PCT/US2014/023091, International Preliminary Report on Patentability dated Sep. 24, 2015", 11 pgs.
"International Application Serial No. PCT/US2014/023091, International Search Report dated Oct. 9, 2014", 7 pgs.

(56) References Cited

OTHER PUBLICATIONS

"International Application Serial No. PCT/US2014/023091, Written Opinion dated Oct. 9, 2014", 9 pgs.
"International Application Serial No. PCT/US2014/028942, International Preliminary Report on Patentability dated Sep. 24, 2015", 15 pgs.
"Isolation of Granulocytes From Human Peripheral Blood by Density Gradient Centrifugation", Miltenyi Biotec GmbH, (2008), 2 pgs.
"Japanese Application Serial No. 2010-503066, Office Action dated Jan. 22, 2013", w/ English Translation, 17 pgs.
"Japanese Application Serial No. 2012-503768, Office Action dated May 20, 2014", w/ English Translation, 5 pgs.
"Japanese Application Serial No. 2012-520742, Office Action dated Sep. 9, 2014", w/ English Translation, 6 pgs.
"Japanese Application Serial No. 2012-526988, Office Action dated Oct. 1, 2013", W/ English Translation, 4 pgs.
"Japanese Application Serial No. 2012-526988, Response filed Mar. 3, 2014 to Office Action dated Oct. 1, 2013", W/ English Claims, 21 pgs.
"Japanese Application Serial No. 2012-526990, Examiners Decision of Final Refusal dated Jun. 3, 2016", W/ English Translation, 6 pgs.
"Japanese Application Serial No. 2012-526990, Office Action dated Jun. 26, 2015", W/ English Translation, 12 pgs.
"Japanese Application Serial No. 2012-526990, Office Action dated Aug. 5, 2014", W/ Machine Translation, 4 pgs.
"Japanese Application Serial No. 2012-526990, Response filed Dec. 5, 2014 to Office Action dated Aug. 5, 2014", W/ English Claims, 19 pgs.
"Japanese Application Serial No. 2012-526990, Response filed Dec. 25, 2015 to Office Action dated Jun. 26, 2015", W/ English Translation, 14 pgs.
"Japanese Application Serial No. 2012-527030, Office Action dated Jun. 12, 2015", W/ English Translation, 2 pgs.
"Japanese Application Serial No. 2013-174962, Notice of Reasons for Rejection dated Jul. 31, 2015", W/ English Translation, 10 pgs.
"Japanese Application Serial No. 2013-174962, Office Action dated Sep. 12, 2014", W/ English Translation, 6 pgs.
"Japanese Application Serial No. 2013-174962, Response filed Mar. 12, 2015 to Office Action dated Sep. 12, 2014", W/ English Translation, 18 pgs.
"Japanese Application Serial No. 2013-174962, Response filed Oct. 30, 2015 to Notice of Reasons for Rejection dated Jul. 31, 2015", W/ English Claims, 16 pgs.
"Japanese Application Serial No. 2013-527119, Examiners Decision of Final Refusal dated Oct. 18, 2016", W/ English Translation, 9 pgs.
"Japanese Application Serial No. 2013-527119, Office Action dated Mar. 1, 2016", W/ English Translation, 12 pgs.
"Japanese Application Serial No. 2013-527119, Office Action dated Jun. 12, 2015", W/ English Translation, 11 pgs.
"Japanese Application Serial No. 2013-527119, Response filed Aug. 1, 2016 to Office Action dated Mar. 1, 2016", W/ English Claims, 13 pgs.
"Japanese Application Serial No. 2013-527119, Response filed Oct. 1, 2015 to Office Action dated Jun. 12, 2015", W/ English Claims, 12 pgs.
"Japanese Application Serial No. 2014-024420, Preliminary Notice of Reasons for Rejection dated Feb. 24, 2015", w! English Translation, 15 pgs.
"Knee Cartilage Implantation Carticel™ , Autologous Cultured Chondrocyte Implantation", The Sports Medicine Center, [Online]. Retrieved from the Internet: <http://www.orthoassociates.com/carticel.htm>, (Apr. 6, 2006), 7 pgs.
"Letter CryoSeal FS System. Vaccines, Blood & Biologics", FDA U.S. Food and Drug Administation., http://www.fda.gov/BiologicsBioodVaccines/BioodBioodProducts/ApprovedProducts/Premarket ApprovalsPMAs/ucm091631.htm, (Jul. 26, 2007), 21 pgs.

"MarrowStim™ Concentration Kit Peripheral Arterial Disease (PAD) Study", Retriewed From lntenet : <http://www.biomet.com/patients/clinical recruitment padstudy.cfm>, (Jul. 2, 2009), 2 pgs.
"MarrowsTim™ Concentration System", Biomet Biologics, Inc, (Feb. 15, 2008), 20 pgs.
"Medical Applications: Blood Filtration", Minntech® Filtration Technologies Group, Minntech Corporation (2004), <http://www.minntech.com/ftg/industries/medical/blood_filter.html>, (Jul. 15, 2004), 1 pg.
"Minivalve international: duckbill valves—du 054.001 sd", [Online]. Retrieved from the Internet: <http://www.minivalve.com/htm/DV054.htm>, 1 pg.
"Momentive Silopren*LSR 2050", (Jun. 30, 2014), 3 pg.
"Plasrnax Plasma Concentrate", Biomet Biologics, Inc, Brochure, (2006), 6 pgs.
"Plasmax@ Plasma Concentration System", Biomet Biologics, (Mar. 2007), 18 pgs.
"Platelet Rich Plasma (PRP)", The Stone Clinic, (May 2006), 2 pgs.
"Prosys PRP Kit", Tozai Holdings, Inc, EC21 Global B2B Marketplace, Retrieved From Internet : <http://www.ec21.com/product-details/Prosys-PRP-Kit--5467061.html Printed from Web>, (Jul. 18, 2011), 5 pgs.
"Renaflo® II Hemofilter", Minntech® Filtration Technologies Group, Minntech Corporation (2004), <http://www.minntech.com/ftg/products/renaflo/index.html>, (Jul. 15, 2004), 2 pgs.
"Shoulder Recovery with the GPS® Platelet Concentrate System, Rotator Cuff Surgical Techniques", Biomet Biologics, Inc., (2004), 6 pgs.
"Sigma-Aldrich@ Alkaline Phosphatase (Procedure No. 85), drug fact sheet", Sigma-Aldrich, (2003), 1-2
"SmartPrep PRP-20 Procedure Pack—Instructions for Use", Harvest, (2002), 12 pgs.
"ThermoGenesis Corp. To Supply Autologous Thrombin Kits to Biomet, Inc", noblood: Transfusion Alternatives Patient Blood Mangement, [Online]. Retrieved from the Internet: <URL: http://noblood.org/forum/threads/2128-ThermoGenesis-Corp-to-Supply-Autologous-Thrombin-Kits-to-Biomet-Inc>, (Apr. 5, 2005), 3 pgs.
"Trypsinizing cells", Bart's Cook Book, (Accessed Apr. 14, 2010), 1 pg.
"Update for veterinarians", Anonymous, [Online]. Retrieved from the Internet: <URL:http://vet.osu.edu/sites/default/files/documents/pdf /news/vmc/ovmaVeterinarianUp/documents/pdf /news/vmc/ovmaVeterinarianUp>, (Dec. 2012).
"Vernay Product Information Sheet, Umbrella Check Valve", Part No. V251010200, (Jul. 2013), 2 pgs.
"Vortech Concentration System Product", Biomet Biologics, Inc., (Aug. 2005), 16 pgs.
Aaron, "Stimulation of Experimental Endochondral Ossification by Low-Energy Pulsing Electromagnetic Fields", Journal of Bone and Mineral Research, (1989), 227-233.
Aaron, et al., "Therapeutic Effects of Electromagnetic Fields in the Stimulation of Connective Tissue Repair", Journal of Cellular Biochemistry, (1993), 42-46.
Aaron, et al., "Upregulation of basal TGFb1 levels by EMF coincident with chondrogenesis—implications for skeletal repair and tissue engineering", Journal of Orthopaedic Research, (2002), 233-240.
Aaron, Roy K., et al., "Acceleration of Experimental Endochondral Ossification by Biophysical Stimulation of the Progenitor Cell Pool", Journal of Orthopaedic Research, (1996), 582-589.
Aaron, Roy K., et al., "Power Frequency Fields Promote Cell Differentiation Coincident With an Increase in Transforming Growth Factor-?1 Expression", Bioelectromagnetics, (1999), 453-458.
Abegao, K., et al., "Effects of heterologous platelet-rich plasma gel on standardized dermal wound healing in rabbits", Acta Cirurgica Brasileira—vol. 30(3), (2015), pp. 208-215.
Abramson, S. B., et al., "Blocking the effects o IL-1 in rheumatoid arthritis protects bone and cartilage", Rheumatology; 41, (2002), 972-980 pgs.
Agu, R. U., et al., "The lung as a route for systemic delivery of therapeutic proteins and peptides", Respir Res.; vol. 2, (2001), pp. 198-209.

(56) References Cited

OTHER PUBLICATIONS

Alford, J Winslow, et al., "Cartilage Restoration, Part 1. Basic Science, Historical Perspective, Patient Evaluation, and Treatment Options", The American Journal of Sports Medicine, 33(2), (2005), 295-306.
Andia, Isabel, et al., "Platelet-rich plasma for managing pain and inflammation in osteoarthritis", Nature Reviews Rheumatology, vol. 9. No. 12., (Oct. 1, 2013), 721-730.
Anitua, Eduardo, et al., "Autologous platelets as a source of proteins for healing and tissue regeneration", Thromb Haemost, vol. 91, (2004), 4-15.
Arend, W, et al., "Interleukin-1 Receptor Antagonist: Role in Biology", Annu. Rev. Immunol., vol. 16, (1998), 27-55.
Badiavas, Evangelos V., et al.; "Treatment of Chronic Wounds With Bone Marrow-Derived Cells", Arch Dermatol. 139, (Apr. 2003), 510-516.
Baltzer, A W, et al., "Autologous conditioned serum (Orthokine) is an effective treatment for knee osteoarthritis. Osteoarthritis Cartilage", (Feb. 1, 2009), 152-60.
Bang, N U, et al., "Plasma Protein Requirements for Human Platelet Aggregation", Acad Sci, 201, (1972), 280-299.
Becker, C, et al., "Efficacy of epidural perineural injections with autologous conditioned serum for lumbar radicular compression an Investigator-initiated, prospective, double-blind, reference-controlled study", (2007), 1803-1808.
Belal, Mahmoud Helmy, "Recombinant Human Platelet-Derived Growth Factor-BB: a promising role for fibroblast cell attachment in chronic periodontitis. A concentration-dependent effect on human cell adhesion: SEM study", Rev. Clin. Pesq. Odontol., Curitiba, v. 5, n. 3, (2009), p. 225-240.
Bendele, Alison M, et al., "Combination Benefit of Treatment With the Cytoki Ne Inhibitors interleukin-1 Receptor Antagonist and Pegylated Soluble Tumor Necrosis Factor Receptor Type I in animal models of Rheumatoid Arthritis", Arthritis & Rheumatism, Wiley, US, vol. 43, No. 1, (Dec. 1, 2000), 2648-2659.
Bendele, Alison M, et al., "Combination Benefit of Treatment With the Cytokine Inhibitors Interleukin-1 Receptor Antagonist and Pegylated Soluble Tumor Necrosis Factor Receptor Type I in Animal Models of Rheumatoid Arthritis", Arthritis & Rheumatism, J.B. Lippincott vol. 43, No. 12, (Dec. 1, 2000), 2648-2659.
Berguer, R, et al., "Warning: fatal reaction to the use of fibrin glue in deep hepatic wounds. Case reports", J Trauma 31, (1991), 408-411.
Berruyer, M, et al., "Immunization by bovine thrombin used with fibrin glue during cardiovascular operations. Development of thrombin and factor V inhibitors", J Thorac Cardiovasc Sura 105, (1993), 892-7.
Bielecki, T, et al., "Antibacterial effect of autologous platelet gel enriched with growth factors and toher acive substances", J Bone Joint Surg, vol. 89-B, No. 3, (Mar. 2007), 417-420.
Boomgaard, et al., "Pooled Platelet Concentrates Prepared by the Platelet-Rich-Plasma Method and Filtered with Three Different Filters and Stored for 8 Days", Vox Sanq, vol. 68, (Feb. 1995), 82-89.
Brodke, et al., "Bone Grafts Prepared with Selective Cell Retention Technology Heal Canine Segmental Defects as Effectively as Autograft", SCR-Enriched Bone Grafts Heal Canine Segmental Defects, Journal of Orthopaedic Research, (May 2006), 857-866.
Burnouf, T, "Blood-derived, tissue engineering biomaterials", Biomedical Engineering-Applications, Basis & Communications, vol. 16, No. 6, (Dec. 6, 2004), 294-304.
Carpenter, et al., "Long-term storage of proteins", Current Protocols in Protein Science, (2002), 6 pgs.
Carpenter, et al., "Rationale Design of stable protein formulations-theory and practice", Rationale design of stable lyophilized protein formulations: theory and practice,, (2002), 109-133.
Casali, B, et al., "Fibrin glue from single-donation autologous plasmapheresis", Transfusion 32, (1992), 641-643.

Clayden, J D, et al., "Improved segmentation reproducibility in group tractography using a quantitative tract similarity measure", Neuroimage, Academic Press, Orlando, FL, US vol. 33, No. 2, (Nov. 1, 2006), 482-492.
Collier, B S, et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda Blood, vol. 47, No. 5, (May 1976).
Connolly, John, et al., "Development of an Osteogenic Bone-Marrow Preparation", The Journal of Bone and Joint SurQery, Incorporated, vol. 71-A, No. 5, (Jun. 1989), 684-691.
Connolly, John F., "Injectable Bone Marrow Preparations to Stimulate Osteogenic Repair", Clinical Orthopaedics and Related Research 313, (Apr. 1995), 8-18.
Dallari, et al., "Enhanced Tibial Osteotomy Healing with Use of Bone Gratis Supplemented with Platelet Gel or Platelet Gel and Bone Marrow Stromal Cells", The Journal of Bone and Joint Surgery, vol. 89, (2007), 2413-2420.
Dallari, et al., "In Vivo Study on the Healing of Bone Defects Treated with Bone Marrow Stromal Cells, Platelet-Rich Plasma, and Freeze-Dried Bone Allografts, Alone and in Combination", Healing of Bone Defects, Journal of Orthopaedic Research, (May 2006), 877-888.
Danis, V. A., et al., "Cytokine production by normal human monocytes: inter-subject variation and relationship to an IL-1 receptor antagonist (IL-IRa) gene polymorphism", Clin Exp Immunol; (99), (1995), p. 303-310.
Dawson, J, et al., "Effects of soluble interleukin-1 type II receptor on rabbit antigen-induced arthritis: Clinical, biochemical and histological assessment", Rheumatology (Oxford) vol. 38, No. 5, (May 5, 1999), 401-406.
Dayer, Jean-Michel, et al., "Adipose tissue has anti-inflammatory properties: focus on IL-1 receptor antagonist (IL-1Ra)", Annals of the New York Academy of Sciences, vol. 1069, (Jun. 2006), 444-53.
De Ugarte, et al., "Comparison of Multi-Lineage Cells from Human Adipose Tissue and Bone Marrow", Cells Tissues Organs 174, (2003), 101-109.
De Ugarte, et al., "Differential Expression of Stem Cell Mobilization-Associated Molecules on Multi-Lineage Cells from Adipose Tissue and Bone Marrow", Immunology Letters 89, (2003), 267-270.
De Wit, et al., "Experiments on the Preparation of Blood Components with the IBM 2991 Blood Cell Processor", Vox Sang. 29, (Feb. 10, 1975), 352-362.
Delrossi, A, et al., "Platelet-rich plasma reduces postoperative blood loss after cardiopulmonary bypass", J Thorac Cardiovasc Sura 100, (Aug. 1990), 281-285.
Depalma, L, "The preparation of fibrinogen concentrate for use as fibrin glue by four different methods", Transfusion vol. 33, No. 9, (1993), 717-720.
Deugarte, M D, et al., "Future of Fat as Raw Material for Tissue Regeneration", Lippincott Williams & Wilkins, Inc., (2007), 215-219.
Dimuzio, Paul, et al., "Development of a Tissue-Engineered Bypass Graft Seeded with Stem Cells", Vasucular, vol. 14, No. 6, (2006), 338-342.
Dinarello, C, "Interleukin-1 and Interleukin-1 Antagonism", Blood, vol. 77, No. 8, (Apr. 1991), 1627-1652.
Dinarello, C A, "Interleukin-1 in the pathogenesis and treatment of inflammatory diseases", Blood, 2011, vol. 117(14),, (2011), 3720-3732.
Edlich, Richard F, et al., "Surgical Devices in Wound Healing Management", In Wound Healing: Biochemical & Clinical Aspects 1st ed., vol. Philadelphia: W.B. Saunders Company, (1992), 581-601.
Ehricke, H H, et al., "Visualizing MR diffusion tensor fields by dynamic fiber tracking and uncertainty mapping", Computers and Graphics, Elsevvier vol. 30, No. 2, (Apr. 1, 2006), 255-264.
Eppley, et al., "Platelet Quantification and Growth Factor Analysis from Platelet-Rich Plasma: Implications for Wound Healing", Plastic and Reconstructive Surgery, 114(6), (Nov. 2004), 1502-1508.

(56) References Cited

OTHER PUBLICATIONS

Epstein, G H, et al., "A new autologous fibrinogen-based adhesive for otologic surgery", Ann Otol Rhinol Laryngol 95, (May 25-26, 1985), 40-45.

Evans, C H, "Novel biological approaches to the intra-articular treatment of osteoarthritis", BioDrugs, (2005), 355-62.

Feige, U, et al., "Anti-interleukin-1 and anti-tumor necrosis factor-alpha synergistically inhibit adjuvant arthritis in Lewis rats", Cmls Cellular and Molecular Li Fe Sciences, Bi Rkhauser Verlag, Heidelberg, DE, vol. 57, No. 10, (Sep. 1, 2000), 1457-1470.

Fini, et al., "Effects of pulsed electromagnetic fields on articular hyaline cartilage: review of experimental and clinical studies", Biomedicine and Pharmacotherapy, Elsevier, FR, vol. 59, No. 7, (Aug. 1, 2005), 388-394.

Fini, M., et al., "Effects of pulsed electromagnetic fields on articular hyaline cartilage: review of experimental and clinical studies", Biomed Pharmacother; vol. 59, (2005), pp. 388-394.

Fiotti, et al., "Atherosclerosis and Initammation. Patterns of Cytokine Regulation in Patients with Peripheral Arterial Disease", Atherosclerosis. Elsevier Ireland Ltd. IE, vol. 145, No. 1, (Jul. 1, 1999), 51-60.

Floryan, K, et al., "Home Study Program: Intraoperative use of Autologous Platelet-Rich and Platelet-Poor Plasma for Orthopedic Surgery Patients", AORN Journal: Home Study Program, 80(4), (Oct. 2004), 667-678.

Fraser, John K, et al., "Plasticity of human adipose stem cells toward endothelial cells and cardiomyocytes", Nature Clinical Practice Cardiovascular Medicine, vol. 3, Supplement 1, (Mar. 2006), S33-S37.

Friesen, Robert, et al., "Blood Conservation During Pediatric Cardiac Surgery: Ultrafiltration of the Extracorporeal Circuit Volume After Cardiopulmonary Bypass", Anesth, Analg, (1993), 702-707.

Galois, et al., "Cartilage Tissue Engineering: State-of-the-Art and Future Approaches", Pathol Bioi (Paris), 53—Abstract only, (Dec. 2005), 2 pgs.

Gerald, Marx, "Mechanism of Fibrin Coagulation Based on Selective, Cation-Driven, Protofibral Association", Biopolymers, vol. 27, (1988), 763-774.

Gibble, et al., "Fibrin glue: the perfect operative sealant", Transfusion, 1990, vol. 30, No. 8., (1990), 741-747.

Gimble, Jeffrey M, "Adipose-Derived Stem Cells for Regenerative Medicine", Circulation Research American Heart Association, Inc., (May 11, 2007), 1249-1260.

Gomillion, Cheryl T, et al., "Stem cells and adipose tissue engineering", Biomaterials 27, Science Direct Elsevier, (2006), 6052-6063.

Greppi, N., et al., "Treatment of recalcitrant ulcers with allogeneic platelet gel from pooled platelets in aged hypomobile patients", Biologicals. Academic Press Ltd. vol. 39. No. 2, (Jan. 6, 2011), 73-80 pgs.

Grove, et al., "Plasticity of Bone Marrow-Derived Stem Cells", Stem Cells: Concise Review, (Jan. 2004), 487-500.

Guilak, Farshid, et al., "Adipose-derived adult stem cells for cartilage tissue engineering", Biorheology 41, (2004), 389-399.

Gullung, Gregory B., et al., "Platelet-rich plasma effects on degenerative disc disease: analysis of histology and imaging in an animal model", Evidence-Based Spine-Care Journal, vol. 2, Issue 4, (2011), 13-18.

Harris, E. L.V, et al., "Protein Purification Methods—A Practical Approach", Clarification and Extraction, (1989), 7 pgs.

Hartman, A. R, et al., "Autologous whole plasma fibrin gel. Intraoperative procurement", Arch Surg 127, (Mar. 1992), 357-359.

Hattori, et al., "Osteogenic Potential of Human Adipose Tissue-Derived Stromal Cells as an Alternative Stem Cell Source", Cells Tissues Organs, (2004), 2-12.

Haynesworth, S E, et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.

Hennis, H L, et al., "Infectious disease risks of fibrin glue [letter]", Ophthalmic Sura 23, (Sep. 1992), 1 pg.

Hernigou, et al., "Percutaneous Autologous Bone-Marrow Grafting for Nonunions, Influence of the Number and Concentration of Progenitor Cells", Journal of Bone & Joint Surgery, (Jul. 2005), 1430-1437.

Hiromasa, Mitsuhata, et al., "An Anaphylactic Reaction to Topical Fibrin Glue", Anesthesiology, vol. 81, No. 4, (Oct. 1994), 1074-1077.

Hom, D, et al., "Promoting Healing with Recombinant Human Platelet-Derived Growth Factor-BB in a Previously Irradiated Problem Wound", The Laryngoscope, vol. 113, (Sep. 2003), 1566-1571.

Honore, Prisca, et al., "Interleukin-1aB gene-deficient mice show reduced nociceptive sensitivity in models of inflammatory and neuropathic pain but not post-operative pain", Behavioral Brain Research, (2006), 355-364.

Hood, Andrew G, et al., "Perioperative Autologous Sequestration III: A New Physiologic Glue with Wound Healing Properties", (Jan. 1993), 126-129.

Hou, W H, et al., "Microfluidic Devices for Blood Fractionation", Micromachines, (2011), 319-343.

Ishida, et al., "Platelet-Rich Plasma With Biodegradable Gelatin Hydrogel Promotes Rabbit Meniscal Tissue Regeneration", 52nd Annual Meeting of the Orthopaedic Research Society Paper No. 1035, (2006), 1 pg.

Jackson, C M, et al., "Blood coagulation", Annu Rev Biochem 49: 765-811, (1980), 22 pgs.

Jayadev, Suprya, "Trypsinization of Adherent Cells", (Aug. 8, 1991), 1 pg.

Johnstone, et al., "Autologous Mesenchymal Progenitor Cells in Articular Cartilage Repair", Clinical Orthopaedics and Related Research 367S:, (Oct. 1999), 5156-5162.

Jones, D K, et al., "Confidence mapping in diffusion ensor magnetic resonance imaging tractography using a bootstrap approach", Magnetic Resonance in Medicine Wiley USA, vol. 53, No. 5, (May 2005), 1143-1149.

Jorgensen, et al., "Stem Cells for Repair of Cartilage and Bone: The Next Challenge in Osteoarthritis and Rheumatoid Arthritis", Annals of Rheumatic Diseases, (Aug. 2000), 5 pgs.

Juge-Aubry, C, et al., "Adipose Tissue is a Major Source of Interleukin-1 Receptor Antagonist: Upregulation in Obesity and Inflammation", Diabetes, vol. 52, (May 2004), 1104-1110.

Juge-Aubry, C, et al., "Regulatory Effects of Interleukin (IL)-1, Interferon-β. and IL-4 on the Production of IL-1 Receptor Antagonist by Human Adipose Tissue", The Journal of Clinical Endocrinology & Metabolism, vol. 89, No. 6, (Jun. 2004), 2652-2658.

Karpatkin, S., "Heterogeneity of Human Platelets. VI., Correlation of Platelet Function with Platelet Volume", Blood, vol. 51, No. 2, (Feb. 1978), 307-316.

Kaufman, A, et al., "Human macrophage response to UHMWPE, TiAIV, Coer, and alumina particles: Analysis of multiple cytokines using protein arrays", Journal of Biomedical Materials Research Part A, published online in Wiley InterScience, (Jul. 2007), 464-474.

Kim, Seon Hee, et al., "Ex Vivo Gene Delivery of Il-Lra and Soluble Tnf Receptor Confers a Distal Synergistic Therapeutic Effect in Antigen-Induced Arthritis", Molecular Therapy, Nature Publishing Group, GB, vol. 6, No. 5, (Nov. 1, 2002), 591-600.

Kim, Seon Hee, et al., "Ex vivo gene delivery of Il-1 Ra and soluble TNF receptor confers a distal synergistic therapeutic effect in antigen-induced arthritis", Molecular Therapy, vol. 6, No. 5, (Nov. 1, 2002), 591-600.

Kim, Sun Jin, et al., "Development of a novel sustained release formulation of recombinant human growth homrone using sodium hyaluronate microparticles", Journal of Controlled Release, 2005, vol. 104,, (2005), 323-335.

Kimble, Robert B, et al., "Simultaneous block of interleukin-1 and tumor necrosis factor is required to completely prevent bone loss in the early postovariectomy period", Endocrinology, The Endocrine Society, US, vol. 136, No. 7—Abstract, (Jul. 1, 1995), 1 pg.

(56) References Cited

OTHER PUBLICATIONS

King, William, et al., "A Simple Method to Correlate the Concentration of an Anti-Inflammatory Cytokine with White Blood Cells in an Autologous Protein Solution", [Online]. Retrieved from the Internet: <URL:http://prgmobileapps.com/AppUpdates/ors/Abstract/abs391 .html>, (Feb. 24, 2014).

Kitazawa, R, et al., "Interleukin-1 Receptor Antagonist and Tumor Necrosis Factor Binding Protein Decrease Osteoclast Formation and Bone Resorption in Ovariectomized Mice", Journal of Clinical Investigation, American Society for Clinical Investigation, US, vol . 94, No. 6, (Dec. 1, 1994), 2397-2406.

Kjaergard, H. K, et al., "A simple method of preparation of autologous fibrin glue by means of ethanol", Surg Gynecol Obstet 175, (1992), 72-3.

Kjaergard, H. K, "Preparation of autologous fibrin glue from pericardial Blood", Ann Thorac Sur 55, (1993), 543-4.

Klingenberg, et al., "Treating inflammation in Atherosclerotic Cardiovascular Disease: Emerging Therapies", European Heart Journal., vol. 30, No. 23, (Dec. 2009), 2838-2844.

Kohsaka, Hitoshi, "Gene Transfer Therapy for Rheumatoid Arthritis", Japanese Journal of Clinical Medicine, No. 63, No. 9, (2005), 8 pgs.

Kuderma, H, et al., "Die klinische Anwendung der Klebung van Nervenanastomosen mit Gerinnungssubstanzen bei der Rekonstruction verletzter peripherer Nerven", Wein Klin Wochenschr 87—Not in English, (Aug. 15, 1975), 6 pgs.

Kumar, Vijay, et al., "Autologous Thrombin: Intraoperative Production From Whole Blood", Journal of American Society of Extra-Corporeal Technology. JECT, 40, (2008), 94-98.

Kumar, Vijay, et al., "Stability of Human Thrombin Produced From 11 ml of Plasma Using the Thrombin Processing Device", Journal of American Society of Extra-Corporeal Technology JECT, 37, (Mar. 2005), 390-395.

Kumar, Vijay, et al., "Whole Blood Thrombin: Development of a Process for Intra-Operative Production of Human Thrombin", Journal of American Society of Extra-Corporeal Technology JECT, 39, (Jan. 1, 2007), 18-23.

Kwon, Young-Bae, et al., "Topical application of epidermal growth factor accelerates wound healing by myofibroblast proliferation and collagen synthesis in rat", Journal of Vetrinary Science 7(2), (2006), 105-109 pgs.

Kyosti Laitakari, M D, et al., "Autologous and Homologous Fibrinogen Sealants: Adhesive Strength", Laryngoscope vol. 99, (Sep. 1989), 974-976, Laplante, Ben L, et al., "Spine osteoarthritis", PM&R, vol. 4, (2012), S28-S36.

Lasher, Lisa, "My Experience with PRP", PowerPoint presentation, <http://www.cellfactortech.com/global_products.cfm>, (Sep. 16, 2005), 35 pgs.

Lavi, Galia, et al., "Sustained delivery of IL-1 Ra from biodegradable microspheres reduces the number of murine 816 melanoma lung metastases", Journal of Controlled Release, 123, (2007), 123-130.

Lendeckel, Stefan, et al., "Autologous stem cells (adipose) and fibrin glue used to treat widespread traumatic calvarial defects: case report", Journal of Cranio-Maxillofacial Surgery (2004) European Association for Cranio-Maxillofacial Surgery, (2004), 370-373.

Longas, Maria O, "An Improved Method for the Purification of Human Fibrinogen", J. Biochem vol. 11, (1980), 559-564.

Lori, N F, et al., "Diffusion tensor fiber tracking of human brain connectivity: acquisition methods, reliability analysis and biological results", NMR in Biomedicine Wiley UK, vol. 15, No. 7-8, (Nov. 2002), 493-515.

Lu, X, et al., "Bone Marrow Mesenchymal Stem Cells: Progress in Bone/Cartilage Defect Repair", 19(1) Abstract, (Jan. 2002), 2 pgs.

Lucarelli, E, et al., "Platelet-derived growth factor's enhance proliferation of human stromal stem cells", Biomaterials, vol. 24, (2003), 3095-3100.

Ma, Chaoyong, "Animal Models of Disease: These systems are becoming increasingly important secondary screes of in vitro hits.", Modern Drug Discovery, (Jun. 2004), pp. 30-36.

Marx, Gerard, et al., "Heat Denaturation of Fibrinogen to Develop a Biomedical Matrix", Journal of Biomedical Materials Research Part B: Applied Biomaterials, (Apr. 2007), 49-57.

Masri, Marwan A, et al., "Isolation of Human Fibrinogen of High Purity and in High Yield Using Polyethylene Glycol 1000", Thromb Haemostas (Struttgart) vol. 49 (2), (1983), 116-119.

Matras, Helene, "Fibrin Seal: The State of the Art", Journal of Oral Maxillofacial Surgery, vol 43, (1985), 605-611.

Matthews, J, et al., "Comparison of the response of primary human peripheral blood mononuclear phagocytes from different donors to challenge with model polyethylene particles of known size and dose", Biomaterials, vol. 21, (2000), 2033-2044.

Matuska, et al., "Autologous Solution Protects Bovine Cartilage Explants from IL-1a and STFa-Induced Cartilage Degradation", Journal of Orthopaedic Research, (Jul. 16, 2013), 7 pgs.

Mehmet, C, et al., "Autologous Fibrin Glue From Intraoperatively Collected Platelet-Rich Plasma", Ann Thorac Surg, vol. 53, (1992), 530-531.

Mehta, Sanjay, et al., "Gentamicin distribution from a collagen carrier", Journal of Orthopaedic Research, vol. 14, No. 5—Abstract, (Sep. 1, 1996), 749-754.

Meijer, H, et al., "The production of antiinflammatory cytokines in whole blood by physico-chemical induction", lnftamm. Res. vol. 52, (Oct. 2003), 404-407.

Molnar, Amy, "Stem Cells from Muscles Can Repair Cartilage, Study Finds Genetically Engineered Muscle-Derived Stem Cells Improved Cartilage Repair in Rats", American College of Rheumatology, (2005), 2 pgs.

Moretz, W., et al., "A simple autologous fibrinogen glue for otologic surgery", Otolarvnaol Head Neck Surg 95, (Jul. 1986), 122-4.

Morizaki, et al., "The Effects of Platelet-Rich Plasma on Bone Marrow Stromal Cell Transplants for Tendon Healing in Vitro", J. Hand Surg. Am., vol. 35, No. 11, (Nov. 2010), 1833-1841.

Murphy, Michael P, et al., "Autologous Bone Marrow Mononuclear Cell Therapy Is Safe and Promotes Amputation-Free Survival in Patients With Critical Limb Ischemia", Journal of Vascular Surgery, C.V. Mosby Co., St. Louis, MO, US, vol . 53, No. 6, (Jan. 28, 2011), 1565-1574.

Muzio, M, et al., "Interleukin-13 Induces the Production of Interleukin-1 Receptor Antagonist (IL-1ra) and the Expression of the mRNA for the Intracellular (Keratinocyte) Form of IL-1ra in Human Myelomonocylic Cells", Blood, vol. 83, No. 7, (Apr. 1994), 1738-1743.

Nakagami, Hironori, et al., "Novel Autologous Cell Therapy in Ischemic Limb Disease Through Growth Factor Secretion by Cultured Adipose Tissue-Derived Stromal Cells", Angiogenesis by Adipose Tissue-Derived Cells, American Heart Association, Inc., (Dec. 2005), 2542-2547.

Nalamachu, Srinivas, "An Overview of Pain Management: The Clinical Efficacy and Value of Treatment", Am. J. Manag. Care. 19, (2013), 261-266.

Nathan, Suresh, et al., "Cell-Based Therapy in the Repair of Osteochondral Defects: A Novel Use for Adipose Tissue", Tissue Engineering, vol. 9, No. 4, Mary Ann Liebert, Inc., (2003), 733-744.

Nilsson, et al., "Bone Repair Induced by Bone Morphogenetic Protein in Ulnar Defects in Dogs", The Journal of Bone and Joint Surgery, vol. 68 B., No. 4, (Aug. 1986), 635-642.

Nursen, Duzgun, et al., "Cytokine inhibitors: soluble tumor necrosis factor receptor 1 and interleukin-1 receptor antagonist in Behcet's disease", Rheumatology International ; Clinical and Experimental Investigations, Springer, Berlin, DEvol. 25, No. 1 (Jan. 2005), 1-5.

Obata, Shuji, et al., "Effect of autologous platelet-rich plasma-releasate on intervertebral disc degeneration in the rabbit anular puncture model: a preclinical study", Arthritis Research & Therapy. vol. 14 http://arthritis-research.com/content/14/6/R241, (2012), 12 pgs.

Okamoto, Y, et al., "Determination of soluble tumor necrosis factor-alpha receptor type (TNFRI) and II (TNFRII) in the urine of healthy Japanese subjects", Journal of Immunoassay and Immunochemistry, 2011, vol. 32 (2011), 145-155.

(56) References Cited

OTHER PUBLICATIONS

Okunishi, K, et al., "Hepatocyte Growth Factor Significantly Suppresses Collagen-Induced Arthritis in Mice", The Journal of Immunology, vol. 179, No. 8, (Oct. 15, 2007), 15 pgs.
Orphardt, Charles E, "Denaturation of Proteins", Virtual Chembook, Elmhurst College, <http://www.elmhurst.edu/chm/vchembook/568denaturation.html> (web accessed Mar. 9, 2011), (2003), 3 pgs.
O'Shaughnessey, Krista, et al., "Autologous Protein Solution Prepared From the Blood of Osteoarthritic Patients Contains an Enhanced Profile of Anti-Inflammatory Cytokines and Anabolic Growth Factors", Journal of Orthopaedic Research, (Jun. 1, 2014), 1349-1355 pgs.
O'Shaughnessey, Krista M, et al., "Blood-derived anti-inflammatory protein solution blocks the effect of IL-1 beta on human macrophages in vitro", Imflammation Research, vol. 60, No. 10,, (Oct. 1, 2011), 929-936.
Parchment, et al., "Roles for in vitro myelotoxicity tests in preclincial drug development and clinical trial planning, Toxicology Pathology, Society of Toxicological Pathologists", vol. 21, No. 2, (1993), 241-250.
Parker, Anna M, et al., "Adipose-derived stem cells for the regeneration of damaged issues", Expert Opinion, Cell- & Tissue-based Therapy, Expert Opin. Bioi. Ther., Informa UK Ltd, (2006), 567-578.
Pettit, et al., "The development of site-specific drug-delivery systems for protein and peptide biopharmaceuticals", Trends in Biotechnology, (1998), 343-349.
Planat-Benard, V., et al., "Spontaneous Cardiomyocyte Differentiation From Adipose Tissue Stroma Cells", Adipose-Derived Cell Cardiomyocyte, American Heart Association, Inc., (Feb. 6, 2004), 223-229.
Pommer, et al., "Dielectophoretic separation of platelets from whole blood in microfluidic channels", Electrophoresis, (2008), 1213-1218.
Ponticiello, Michael S, "A Rapid Technique for the Isolation and Concentration of Stem Cells from Human Bone Marrow", Cell Factor Technologies, Inc., (2006), 1 pg.
Rader, C, et al., "Cytokine Response of Human Macrophage-like Cells After Contact With Polyethylene and Pure Titanium Particles", The Journal of Arthroplasty, vol. 14, No. 7, (Oct. 1999), 840-848.
Rader, Christoph, et al., "Phage display of combinatorial antibody libraries", Curr Opin Biotechnol., 8(4), (Aug. 1997), 503-8.
Rangappa, Sunil, et al., "Transformation of Adult Mesenchymal Stem Cells Isolated From the Fatty Tissue Into Cardiomyocytes", Adult Stem Cells Transformed into Cardiomyoctyes, Ann Thorac Surg, (2003), 775-779.
Ravi Kumar, H. S., et al., "Autologous Conditioned Serum as a Novel Alternative Option in the Treatment of Unilateral Lumbar Radiculopathy: A Prospective Study", Asian Spine Journal; 9(6), (2015), 916-922.
Re, Fabio, et al., "Expression of interleukin-1 receptor antagonist (IL-ra) by human circulating polymorphonuclear cells", European Journal of Immunology, 23, (1993), 570-573 pgs.
Rigotti, M D, et al., "Clinical Treatment of Radiotherapy Tissue Damage by Lipoaspirate Transplant: A Healing Process Mediated by Adipose-Derived Adult Stem Cells", Plastic and Reconstructive Surgery, Breast, PRS Journal vol. 119, No. 5, Stem Cell Therapy for Angiogenesis, (Apr. 15, 2007), 1409-1422.
Robert, Quigley L, et al., "Intraoperative Procurement of Autologous Fibrin Glue", Ann Thorac Surg, vol. 56, (1993), 387-389.
Rubin, M. D., et al., "Clinical Treatment of Radiotherapy Tissue Damage by Lipoaspirate Transplant: A Healing Process Mediated by Adipose-Derived Adult Stem Cells", Plastic and Reconstructive Surgery, Discussion vol. 119, No. 5, Stem Cell Therapy for Angiogenesis, (Apr. 15, 2007), 1423-1424.
Sadeghi, M, et al., "Strikingly higher interleukin (1L)-1a, IL-1b and soluble interleukin-1 receptor antagonist (sIL-1RA) but similar IL-2, sll-2R, IL-3, IL-4, IL-6, sII-6R, IL-10, tumour necrosis factor (TNF)-a, transforming growth factor (TGF)-B2, (cont.)", (Title cont. "transforming growth factor (TGF)-(32 and interferon IFN-y urine Levels in healthy females compared to healthy males: protection against urinary tract injury?") Clinical and Experimental Immunology, vol. 142, (2005), 312-317.

Sampson, Steven, et al., "Platelet rich plasma injection grafts for musculoskeletal injuries: a review", Curr Rev Musculoskelet Med, vol. 1, (Jul. 16, 2008), 165-174.
Sanal, M, et al., "Does fibrin glue cause foreign body reactions?", Eu r J Pediatr Sura 2, (1992), 285-6.
Sarzi-Puttini, Piercarlo, et al., "The Appropriate Treatment of Chronic Pain", Clin. Drug Investig. 32, (2012), 21-33.
Schaffler, Andreas, et al., "Concise Review: Adipose Tissue-Derived Stromal Cells-Basic and Clinical Implications for Novel Cell-Based Therapies", Tissue-Specific Stem Cells, Stem Cells®, (Apr. 10, 2007), 12 pgs.
Schmidt, K G, "Labelling of Human and Rabbit Platelets with Indium-Oxine Complex", (1979), 97-106.
Schmidt, K G, et al., "Preparation of Platelet Suspensions from Whole Blood in Buffer", Scand. J. Haemato, 23, (1979), 88-96.
Semple, Elisabeth, et al., "Quality of Thrombin Produced From the Patient's Own Plasma Using the TPD™, a New Thrombin-Processing Device", Journal of American Society of Extra-Corporeal Technology, 37(2), (2005), 196-200.
Sevenoaks, Martin J., et al., "Chronic Obstructive Pulmonary Disease, inflammation and co-morbidity—a common inflammatory phenotype?", respiratory Research vol. 7:70, (2006), 1-9.
Shiozawa, Kazuko, et al., "Gene Therapy, Is a total therapy for rheumatoid arthritis possible?", Pharma Medica, vol. 17, No. 10 w/ partial English Translation, (1999), 16 pgs.
Shrivastava, Abha, et al., "Effects of Electromagnetic Forces of Earth on Human Biological System", Indian J. Prev. Soc. Med, Retrieved from the Internet: <URL:http://medind.nic.in/ibl/t09/i3/iblt09i3p162.pdf>, (Jan. 1, 2009), 162-167.
Shu-Li, Lin, et al., "Static magnetic field attenuates mortality rate of mice by increasing the production of IL-1 receptor antagonist", Int. J. Radial., Biol. 2009, 85(7), (Jul. 31, 2009), 633-640.
Siedentop, Karl H, et al., "Autologous Fibrin Tissue Adhesive", Laryngoscope, vol. 95, (Sep. 1985), 1074-1076.
Siedentop, Karl H, et al., "Extended Experimental and Preliminary Surgical Findings with Autologous Fibrin Tissue Adhesive Made from Patient's Own Blood", Laryngoscope, vol. 96, (Oct. 1986), 1062-1064.
Sierra, D H, "Fibrin sealant adhesive systems: a review of their chemistry, material properties and clinical applications", J Biomater Appl 7, (Apr. 1993), 309-52.
Silver, Frederick H, et al., "REVIEW Preparation and use of fibrin glue in surgery", Biornaterials 16 (1995), (1995), 891-903.
Solchaga, Luis A., et al., "Hyaluronic Acid-Based Polymers As Cell Carriers for Tissue-Engineered Repair of Bone and Cartilage", Journal of Orthopaedic Research, Orthopaedic Research Society, US, vol. 17, (Jan. 1, 1999), 205-213.
Solem, Jan Otto, et al., "Hemoconcentration by Ultrafiltration During Open-Heart Surgery", Scand J Thor Cardiovasc Surg 22, (1988), 271-274.
Sorbera, L A, "Pegsunercept. Pegylated Soluble Tumor Necrosis Factor Receptor Type 1 Peg-Stnf-Rl", Drugs of the Future, Prous Science, ES, vol. 28, No. 12, (Jan. 1, 2003), 1182-1188.
Spotnitz, William D, et al., "Successful Use of Fibrin Glue During 2 Years of Surgery at a University Medical Center", The American Surgeon, vol. 55 (Mar. 1989), 166-168.
Stankiewicz, W., et al., "Low energy electromagnetic fields and immunity", Int. Rev. Allergol. Clin. Immunol, vol. 15, No. 1-2, (2009), pp. 36-41.
Sutton, Robin G, et al., "Comparison of Three Blood-Processing Techniques During and After Cardiopulmonary Bypass", Ann Thorac Surg (1993) vol. 56, (1993), 6 pgs.
Swift, M, et al., "Characterization of Growth Factors in Platelet Rich Plasma", 1-Cell Factor Technologies, [Online]. Retrieved from the Internet: <http://www.cellfactortech.com/global_products.cfm>, (Sep. 16, 2005), 1 pg.
Takahashi, Kazutoshi, et al., "Induction of Pluripotent Stem Cells from Adult Human Fibroblasts by Defined Factors", Cell, Elsevier Inc., (Nov. 30, 2007), 1-12.
Tateishi-Yuyama, E, et al., "Therapuetic angiogenesis for patients with limb ischaemia by autologous transplantation of bone-barrow cells: a pilot study and randomised controlled trial", The Lancet, (2002), 427-435.

(56) References Cited

OTHER PUBLICATIONS

Tawes, Jr., Roy L, et al., "Autologous Fibrin Glue: The Last Step in Operative Hemostatis", The American Journal of Surgery, vol. 168, (Aug. 1994), 120-122.
Thompson, et al., "Fibrin Glue: A Review of Its Preparation, Efficacy, and Adverse Effects as a Topical Hemostat", Drug Intelligence and Clinical Pharmacy, vol. 22, (Dec. 1988), 946-952.
Tiaka, Elisavet K., et al., "Epidermal Growth Factor in the Treatment of Diabetic Foot Ulcers: An Update", Perspectives in Vascular Surgery and Endovascular Therapy 24(1), (2012), p. 37-44.
Toriumi, Dean M, et al., "Surgical Tissue Adhesives in Otolaryngology-Head and Neck Surgery", Otolaryngologic Clinics of North America, vol. 27, No. 1, (Feb. 1994), 203-209.
Ulich, Thomas R, et al., "Intratrachael Administration of Endotoxin and Cytokines: IV. The Soluble Tumor Necrosis Factor Receptor Type 1 Inhibits Acute Inflammation", American Journal of Pathology; vol. 142, No. 5, (May 1993).
Vangsness, Thomas, et al., "Stimulation of IL-1ra production from platelet-rich plasma", Poster No. 488 presented at 54th Annual Meeting of the Orthopedic Research Society, (Mar. 2-5, 2008), 1 pg.
Wang, "Cell separation by dielectrophoretic field-flow-fractionation", Analytical Chemistry, (2000), 832-839.
Weis-Fogh, U S, "Fibrinogen prepared from small blood samples for autologous use in a tissue adhesive system", Eur Surg Res 20, (1988), 381-9.
Weisman, M D, "Biochemical Characterization of Autologous Fibrinogen Adhesive", Laryngoscope 97, (Oct. 1987), 1186-1190.
Wiseman, David M, et al., "Wound Dressings: Design and Use", in Wound Healing: Biochemical & Clinical Aspects 1st ed., vol., (1992), 562-580.
Woodell-May, J, et al., "Effect of Incubation Time on Production of IL-1ra and sTNF-RI from Platelet-Rich Plasma", Paper No. 200, 55th Annual Meeting of the Orthopaedic Research Society, (Feb. 2009).
Woodell-May, J, et al., "Elution of IL-1ra from a concentrated-plasma matrix—An in vitro study", Poster Presentation at 8th World Congress of the International Cartilage Repair Society, (May 2009), 1 pg.
Woodell-May, J, et al., "Producing Accurate Platelet Counts for Platelet Rich Plasma: Validation of a Hematology Analyzer and Preparation Techniques for Counting", Scientific Foundation. Journal of Carniofacial Surgery, vol. 16, No. 5, (Sep. 2005), 749-756.
Woodell-May, Jennifer, et al., "Autologous Protein Solution Inhibits Mmp-13 Production by II-L[Beta] and Tnf[Alpha]-Stimulated Human Articular Chondrocytes", Journal of Orthopaedic Research, vol. 29, No. 9, (Sep. 1, 2011), 1320-1326.
Wright-Carpenter, T, "Treatment of Muscle Injuries by Local Administration of Autologous Conditioned Serum: A Pilot Study on Sportsmen with Muscle Strains", Int J Sports Med, vol. 25, (Oct. 2004), 588-593.
Xie, X., et al., "Biology of platelet-rich plasma and its clinical application in cartilage repair", Arthritis Research & Therapy, 16:204, (2014), 15 pgs.
Yang, et al., "Protective effects of IL-1Ra or vIL-10 gene transfer on a murine model of wear debris-included osteolysis", Gene Therapy 11, (2004), 483-491.
Yang, T, et al., "Recent Applications of Polyacrylamide as Biomaterials", Recent Patents on Materials Science, vol. 1, (2008), 29-40.
Moon, Eulsik, et al., "In Vivo Osteogenic Potential of Human Adipose-Derived Stem Cells/Poly Lactide-Co-Glycolic Acid Constructs for Bone Regneration in a Rat Critical-Sized Calvarial Defect Model", Tissue Engineering, vol. 13, No. 3, (2007), 619-627.
Yoshida, S. et al., "Elevation of serum soluble tumour necrosis factor (TNF) receptor and IL-1 receptor antagonist levels in bronchial asthma", Clinical and Experimental Immunology, Wiley-Blackwell Publishing Ltd. vol. 106, No. 1, (Oct. 1, 1996), 73-78.
Younger, Jarred, et al., "Pain Outcomes: A Brief Review of Instruments and Techniques", Curr Pain Headache Rep. 13(1), (Feb. 2009), p. 39-43.
Zhang, et al., "IL-1ra alleviates inflammatory hyperalgesia through preventing phosphorylation of NMDA receptor NR-1 subunit in rats", Pain, vol. 135, No. 3, (Mar. 5, 2008), 232-239.
Zhang, et al., "Nanosecond pulse electric field (nanopulse): A novel non-ligand agonist for platelet activation", Archives of Biochemistry and Biophysics, Academic Press, US, vol. 471, No. 2, (Dec. 23, 2007), 240-248.
Zhang, Duan-Zhen, et al., "Transplantation of autologous adipose-derived stem cells ameliorates cardiac function in rabbits with myocardial infarction", Chinese Medical Journal, vol. 120, No. 4 General Hospital of Shenyang Military Region, (2007), 300-307.
Zuk, P. A, et al., "Multilineage cells from human adipose tissue: Implications for cellbased therapies", Tissue Engineering, 7(2), XP00219871 0, ISSN: 1076-3279, (Apr. 1, 2001), 211-228.
U.S. Appl. No. 13/841,083, filed Mar. 15, 2013, Treatment of Inflammatory Respiratory Disease Using Biological Solutions.
U.S. Appl. No. 13/837,005 U.S. Pat. No. 9,758,806, filed Mar. 15, 2013, Acellular Compositions for Treating Inflammatory Disorders.
U.S. Appl. No. 13/837,480, filed Mar. 15, 2013, Treatment of Pain Using Protein Solutions.
U.S. Appl. No. 13/839,280, filed Mar. 15, 2013, Methods for Making Cytokine Compositions From Tissues Using Non-Centrifugal Methods.
U.S. Appl. No. 14/050,950 U.S. Pat. No. 9,556,243, filed Oct. 10, 2013, Methods for Making Cytokine Compositions From Tissues Using Non-Centrifugal Methods.
U.S. Appl. No. 14/973,913, filed Dec. 18, 2015, Treatment of Collagen Defects Using Protein Solutions.
U.S. Appl. No. 13/840,129, filed Mar. 15, 2013, Treatment of Collagen Defects Using Protein Solutions.
U.S. Appl. No. 13/841,103, filed Mar. 15, 2013, Treatment of Peripheral Vascular Disease Using Protein Solutions.
U.S. Appl. No. 12/394,723, filed Feb. 27, 2009, Methods and Compositions for Delivering Interleukin-1 Receptor Antagonist.
U.S. Appl. No. 14/808,828 U.S. Pat. No. 9,701,728, filed Jul. 24, 2015, Methods and Compositions for Delivering Interleukin-1 Receptor Antagonist.
U.S. Appl. No. 15/616,548, filed Jun. 7, 2017, Methods and Compositions for Delivering Interleukin-1 Receptor Antagonist.
U.S. Appl. No. 12/549,015 U.S. Pat. No. 8,753,690, filed Aug. 27, 2009, Methods and Compositions for Delivering Interleukin-1 Receptor Antagonist.
U.S. Appl. No. 14/271,722 U.S. Pat. No. 9,308,224, filed May 7, 2014, Methods and Compositions for Delivering Interleukin-1 Receptor Antagonist.
U.S. Appl. No. 13/782,421 U.S. Pat. No. 9,119,829, filed Mar. 1, 2013, Methods and Compositions for Delivering Interleukin-1 Receptor Antagonist.
U.S. Appl. No. 14/803,414, filed Jul. 20, 2015, Methods and Compositions for Delivering Interleukin-1 Receptor Antagonist.
U.S. Appl. No. 14/808,735, filed Jul. 24, 2015, Methods and Compositions for Delivering Interleukin-1 Receptor Antagonist.
U.S. Appl. No. 12/549,116, filed Aug. 27, 2009, Osteolysis Treatment.
U.S. Appl. No. 13/392,266 U.S. Pat. No. 9,763,875, filed Feb. 24, 2012, Implantable Device for Production of Interleukin-1 Receptor Antagonist.
U.S. Appl. No. 14/830,977, filed Aug. 20, 2015, Methods of Treating Spinal Disorders Using Autologous Protein Solutions.
"U.S. Appl. No. 12/394,723, Non Final Office Action dated Nov. 14, 2017", 18 pgs.
"U.S. Appl. No. 12/394,723, Response filed Oct. 16, 2017 to Final Office Action dated May 15, 2017", 18 pgs.
"U.S. Appl. No. 13/837,480, Non Final Office Action dated Dec. 8, 2017", 9 pgs.
"U.S. Appl. No. 13/839,280, Non Final Office Action dated Dec. 28, 2017", 13 pgs.
"U.S. Appl. No. 13/840,562, Final Office Action dated Jun. 30, 2017", 6 pgs.
"U.S. Appl. No. 13/840,562, Non Final Office Action dated Mar. 7, 2017", 18 pgs.
"U.S. Appl. No. 13/840,562, Notice of Allowance dated Oct. 31, 2017", 15 pgs.

(56) References Cited

OTHER PUBLICATIONS

"U.S. Appl. No. 13/840,562, Response filed Jun. 5, 2017 to Non-Final Office Action dated Mar. 7, 2017", 12 pgs.
"U.S. Appl. No. 13/840,562, Response filed Aug. 30, 2017 to Final Office Action dated Jun. 30, 2017", 10 pgs.
"U.S. Appl. No. 14/803,414, Final Office Action dated Oct. 18, 2017", 26 pgs.
"U.S. Appl. No. 14/803,414, Response field Dec. 18, 2017 to Final Office Action dated Oct. 18, 2017", 13 pgs.
"U.S. Appl. No. 14/830,977, Response filed Nov. 6, 2017 to Non Final Office Action dated Aug. 7, 2017", 13 pgs.
"U.S. Appl. No. 14/973,913, Non Final Office Action dated Jan. 16, 2018", 7 pgs.
"U.S. Appl. No. 14/973,913, Response filed Dec. 20, 2017 to Restriction Requirement dated Oct. 20, 2017", 8 pgs.
"U.S. Appl. No. 14/973,913, Restriction Requirement dated Oct. 20, 2017", 7 pgs.
"Australian Application Serial No. 2014229070, First Examination Report dated Nov. 24, 2017", 3 pgs.
"Australian Application Serial No. 2014237269, First Examination Report dated Dec. 11, 2017", 6 pgs.
"Australian Application Serial No. 2014237679, First Examination Report dated Dec. 11, 2017", 4 pgs.
"Chinese Application Serial No. 201480027157.1, Voluntary Amendment filed Jun. 6, 2016", w/English Claims, 63 pgs.
"Chinese Application Serial No. 201480027178.3, Office Action dated Oct. 10, 2017", W/ English Translation, 14 pgs.
"Chinese Application Serial No. 201480027655.6, Response filed Oct. 9, 2017 to Office Action dated May 15, 2017", W/ English Translation of Claims, 9 pgs.
"European Application Serial No. 14707909.9, Summons to Attend Oral Proceedings dated Oct. 18, 2017", 2 pgs.
"European Application Serial No. 14709014.6, Summons to Attend Oral Proceedings dated Oct. 18, 2017", 2 pgs.
"European Application Serial No. 14709803.2, Communication Pursuant to Article 94(3) EPC dated Jul. 8, 2016", 7 pgs.
"European Application Serial No. 14709803.2, Response filed Jul. 17, 2017 to Communication Pursuant to Article 94(3) EPC dated Feb. 17, 2017", 18 pgs.
"European Application Serial No. 14709803.2, Response filed Nov. 15, 2016 to Communication Pursuant to Article 94(3) EPC dated Jul. 8, 2016", 18 pgs.
"European Application Serial No. 14709803.2, Summons to Attend Oral Proceedings dated Oct. 30, 2017", 8 pgs.
"European Application Serial No. 14714491.9, Response filed Oct. 16, 2017 to Non Final Office Action dated Feb. 28, 2017", 18 pgs.
"European Application Serial No. 14724817.3, Response filed Nov. 9, 2017 to Office Action dated Jun. 29, 2017", 19 pgs.
"European Application Serial No. 14729994.5, Communication Pursuant to Article 94(3) EPC dated Oct. 10, 2017", 8 pgs.
"Mexican Application Serial No. Mxa2013002488, Office Action dated Nov. 5, 2015", W/ English Translation, 7 pgs.
Bendinelli, Paola, et al., "Molecular Basis of Anti-Inflammatory Action of Platelet-Rich Plasma on Human Chondrocytes: Mechanisms of Nf-kB Inhibition Via HGF", Journal of Cellular Physiology 225, (2010), 757-766.
Le Meur, Yannick, et al., "Whole blood production of monocytic cytokines (IL-1β, IL-6, TNF-a, sIL-6R, IL-1Ra) in haemodialysed patients", Nephrology Dialysis Transplantation; 14, (1999), pp. 2420-2426.
Matras, Helene, et al., "Zur nahtlosen interfaszikularen Netventransplantation im Tierexperiment", Wein Med Woschtr 122:37—Not in English, (1972), 517-523.
Nakajima, et al., "Bioactivity of freeze-dried platelet-rich plasma in an adsorbed form on a biodegradable polymer material.", Platelets, (2012), 594-603.
Ulich, Thomas R., et al., "Endotoxin-induced Cytokine Gene Expression in Vivo: IV. Expression of Interleukin-1 a/β and Interleukin-1 Receptor Antagonist mRNA During Endotoxemia and During Endotoxin-initiated Local Acute Inflammation", American Journal of Pathology, vol. 141, No. 1, (Jul. 1992), pp. 61-68.

"U.S. Appl. No. 12/394,723, Corrected Notice of Allowability dated Jul. 30, 2018", 5 pgs.
"U.S. Appl. No. 12/394,723, Notice of Allowance dated Jul. 17, 2018", 10 pgs.
"U.S. Appl. No. 13/839,280, Final Office Action dated Jul. 13, 2018", 12 pgs.
"U.S. Appl. No. 14/973,913, Final Office Action dated Aug. 9, 2018", 11 pgs.
"Australian Application Serial No. 2014237269, Response filed Jul. 28, 2018 to Subsequent Examiners Report dated Jun. 29, 2018", 15 pgs.
"Australian Application Serial No. 2014237269, Subsequent Examiners Report dated Jun. 29, 2018", 10 pgs.
"Australian Application Serial No. 2014237679, Response filed Jul. 19, 2018 to Subsequent Examiners Report dated May 29, 2018", 54 pgs.
"Australian Application Serial No. 2014238304, Subsequent Examiners Report dated Jun. 9, 2018", 3 pgs.
"Chinese Application Serial No. 201480027178.3, Office Action dated Jun. 15, 2018", w/ English translation, 9 pgs.
"Chinese Application Serial No. 201480027541.1, Response filed Jul. 27, 2018 to Office Action dated Mar. 14, 2018", W/English Claims, 16 pgs.
"Chinese Application Serial No. 201480028053.2, Office Action dated Jul. 3, 2018", W/English Translation, 6 pgs.
"European Application Serial No. 10754613.7, Communication Pursuant to Article 94(3) EPC dated Jun. 26, 2018", 3 pgs.
"U.S. Appl. No. 12/394,723, Final Office Action dated May 18, 2018", 9 pgs.
"U.S. Appl. No. 12/394,723, Response filed Feb. 14, 2018 to Non Final Office Action dated Nov. 14, 2017", 27 pgs.
"U.S. Appl. No. 12/394,723, Response filed Jun. 18, 2018 to Final Office Action dated May 18, 2018", 7 pgs.
"U.S. Appl. No. 13/837,480, Notice of Allowance dated Jun. 28, 2018", 7 pgs.
"U.S. Appl. No. 13/837,480, Response filed Mar. 8, 2018 to Non Final Office Action dated Dec. 8, 2017", 13 pgs.
"U.S. Appl. No. 13/839,280, Response filed Mar. 28, 2018 to Non Final Office Action dated Dec. 28, 2017", 13 pgs.
"U.S. Appl. No. 14/830,977, Final Office Action dated Feb. 23, 2018", 10 pgs.
"U.S. Appl. No. 14/830,977, Response filed May 23, 2018 to Final Office Action dated Feb. 23, 2018", 11 pgs.
"U.S. Appl. No. 14/973,913, Response filed Apr. 16, 2018 to Non Final Office Action dated Jan. 16, 2018", 12 pgs.
"Australian Application Serial No. 2014229070, Response filed Jan. 15, 2018 to First Examination Report dated Nov. 24, 2017", 25 pgs.
"Australian Application Serial No. 2014237269, Response filed May 21, 2018 to First Examination Report dated Dec. 11, 2017", 25 pgs.
"Australian Application Serial No. 2014237679, Response filed Apr. 23, 2018 to First Examination Report dated Dec. 11, 2017", 50 pgs.
"Australian Application Serial No. 2014237679, Subsequent Examiners Report dated May 29, 2018", 4 pgs.
"Australian Application Serial No. 2014238304, First Examination Report dated Jan. 29, 2018", 4 pgs.
"Australian Application Serial No. 2014238304, Response filed May 15, 2018 to First Examination Report dated Jan. 29, 2018", 50 pgs.
"Australian Application Serial No. 2014238363, First Examination Report dated Feb. 8, 2018", 3 pgs.
"Australian Application Serial No. 2014238363, Response filed May 14, 2018 to First Examination Report dated Feb. 8, 2018", 14 pgs.
"Australian Application Serial No. 2014238367, First Examination Report dated Feb. 16, 2018", 3 pgs.
"Australian Application Serial No. 2014238367, Response filed May 15, 2018 to First Examination Report dated Feb. 16, 2018", 23 pgs.
"Chinese Application Serial No. 201480027178.3, Response filed Feb. 26, 2018 to Office Action dated Oct. 10, 2017", (W/ English Claims), 10 pgs.

(56) References Cited

OTHER PUBLICATIONS

"Chinese Application Serial No. 201480027541.1, Office Action dated Mar. 14, 2018", (W/ English Translation), 14 pgs.
"Chinese Application Serial No. 201480027655.6, Office Action dated Feb. 23, 2018", (W/ English translation), 15 pgs.
"European Application Serial No. 10754613.7, Communication Pursuant to Article 94(3) EPC dated Nov. 28, 2017", 3 pgs.
"European Application Serial No. 10754613.7, Response filed Mar. 29, 2018 to Communication Pursuant to Article 94(3) EPC dated Nov. 28, 2017", 15 pgs.
"European Application Serial No. 14714491.9, Communication Pursuant to Article 94(3) EPC dated Feb. 8, 2018", 6 pgs.
"European Application Serial No. 14724817.3, Communication Pursuant to Article 94(3) EPC dated Apr. 5, 2018", 4 pgs.
"European Application Serial No. 18160602.1, Extended European Search Report dated Apr. 30, 2018", 9 pgs.
Botti, C, et al., "Autologous bone marrow cell therapy for peripheral arterial disease", Stem Cells and Cloning: Advances and Applications, No. 5, (2012), 5-14.
Kubis, N, et al., "Vasculogenesis and Angiogenesis: Molecular and Cellular Controls Part 1: Growth Factors", vol. 9, No. 3, (2003), 227-237.
Milkiewicz, M, et al., "Regulators of angiogenesis and strategies for their therapeutic manipulation", The International Journal of Biochemistry & Cell Biology, vol. 38, No. 3, (2006), 333-357.
Morishita, R, et al., "Safety evaluation of clinical gene therapy using hepatocyte growth factor to treat peripheral arterial disease", Hypertension, vol. 44, No. 2, (2004), 203-209.
Richard, J Powell, et al., "Safety and efficacy of patient specific intramuscular injection of Hgf plasmid gene therapy on limb perfusion and wound healing in patients with ischemic lower extremity ulceration: Results of the HGF-0205 trial", Journal of Vascular Surgery, vol. 52, No. 6, (2010), 1525-1530.
American College of Rheumatology, [Online] Retrieved from the internet: <https://www.rheumatology.org/I-Am-A/Patient-Caregiver/Treatments/Anakinra-Kineret> on Apr. 11, 2019, (2019).
"U.S. Appl. No. 14/803,414, Final Office Action dated Apr. 17, 2019", 13 pgs.
"U.S. Appl. No. 14/830,977, Non Final Office Action dated Apr. 25, 2019", 17 pgs.
"U.S. Appl. No. 14/973,913, Response filed Apr. 1, 2019 to Non Final Office Action dated Jan. 2, 2019", 13 pgs.
"U.S. Appl. No. 15/616,548, Response filed Mar. 4, 2019 to Non Final Office Action dated Dec. 4, 2018", 8 pgs.
"Canadian Application Serial No. 2,906,310, Office Action dated Mar. 6, 2019", 5 pgs.
"Canadian Application Serial No. 2,906,310, Response Filed Feb. 7, 2019 to Examiners Rule 30(2) Requisition dated Aug. 30, 2018", 9 pgs.
"Canadian Application Serial No. 2,906,716, Office Action dated Apr. 9, 2019", 6 pgs.
"Canadian Application Serial No. 2,916,080, Examiners Rule 30(2) Requisition dated Apr. 3, 2019", 4 pgs.
"Canadian Application Serial No. 2,916,080, Response Filed Feb. 5, 2019 to Office Action dated Sep. 6, 2018", 6 pgs.
"Canadian Application Serial No. 2,916,158, Examiners Rule 30(2) Requisition dated Apr. 5, 2019", 6 pgs.
"Canadian Application Serial No. 2,916,190, Examiners Rule 30(2) Requisition dated Apr. 5, 2019", 6 pgs.
"Chinese Application Serial No. 201480027408.6, Office Action dated Mar. 12, 2019", w/ English translation, 15 pgs.
"Chinese Application Serial No. 201480028053.2, Office Action dated Jan. 14, 2019", w/ English translation, 25 pgs.
"Chinese Application Serial No. 201480028053.2, Reponse filed Mar. 28, 2019 to Office Action dated Jan. 14, 2019", w/o English claims, 11 pgs.
"European Application Serial No. 14729994.5, Response filed Apr. 17, 2019 to Communication Pursuant to Article 94(3) EPC dated Jan. 4, 2019", 13 pgs.

"European Application Serial No. 18160602.1, Communication Pursuant to Article 94(3) EPC dated Mar. 8, 2019", 5 pgs.
"European Application Serial No. 18160602.1, Response filed Jan. 25, 2019 to Extended European Search Report dated Apr. 30, 2018", 7 pgs.
Chevalier, et al., "", Arthritis & Rheumatism (Arthritis Care & Research) vol. 61, No. 3, (Mar. 15, 2009), 344-352.
Dinarello, C A, et al., "Treating inflammation by blocking interleukin-1 in a broad spectrum of diseases", Nature Reviews, 11, (2012), 633-652.
Iyer, R S, et al., "Chronic Recurrent Multifocal Osteomyelitis", Review. American J. Roentgenology, 196(6 Suppl), S87-S91.
Mitragotri, et al., "", Nat Rev Drug Discov., 13(9), (Sep. 2014), 655-672.
Okanobo, et al., "", Am J Ophthalmol, 154(1), (Jul. 2012), 63-71.
Peerbooms, J C, et al., "Positive effect of an autologous platelet concentrate in lateral epicondylitis in a double-blind randomized controlled trial: platelet-rich plasma versus corticosteroid injection with a 1-year follow-up", Am J Sports Med/\ vol. 38, No. 2, (Feb. 28, 2010), 255-262.
"U.S. Appl. No. 12/394,723, Corrected Notice of Allowability dated Sep. 26, 2018", 5 pgs.
"U.S. Appl. No. 12/394,723, PTO Response to Rule 312 Communication dated Sep. 4, 2018", 2 pgs.
"U.S. Appl. No. 13/839,280, Notice of Allowability dated Oct. 31, 2018", 9 pgs.
"U.S. Appl. No. 13/839,280, Notice of Allowance dated Oct. 2, 2018", 10 pgs.
"U.S. Appl. No. 13/839,280, Response filed Aug. 27, 2018 to Final Office Action dated Jul. 13, 2018", 9 pgs.
"U.S. Appl. No. 14/803,414, Non Final Office Action dated Oct. 4, 2018", 17 pgs.
"U.S. Appl. No, 14/803,414, Response filed Dec. 20, 2018 to Non Final Office Action dated Oct. 4, 2018", 14 pgs.
"U.S. Appl. No. 14/973,913, Non Final Office Action dated Jan. 2, 2019", 9 pgs.
"U.S. Appl. No, 14/973,913, Response filed Nov. 9, 2018 to Final Office Action dated Aug. 9, 2018", 17 pgs.
"U.S. Appl. No. 15/616,548, Non Final Office Action dated Dec. 4, 2018", 9 pgs.
"U.S. Appl. No. 15/616,548, Response filed Oct. 15, 2018 to Restriction Requirement dated Aug. 16, 2018", 5 pgs.
"U.S. Appl. No. 15/616,548, Restriction Requirement dated Aug. 16, 2018", 7 pgs.
"Australian Application Serial No. 2014237679, Subsequent Examiners Report dated Sep. 18, 2018", 7 pgs.
"Australian Application Serial No. 2014238304, Response filed Sep. 2, 2018 to Subsequent Examiners Report dated Jun. 9, 2018", 41 pgs.
"Canadian Application Serial No. 2,906,310, Examiner's Rule 30(2) Requisition dated Aug. 30, 2018", 6 pgs.
"Canadian Application Serial No. 2,916,080, Office Action dated Sep. 6, 2018", 4 pgs.
"Chinese Application Serial No. 201480027178.3, Decision of Rejection dated Dec. 4, 2018", W/English Translation, 8 pgs.
"Chinese Application Serial 201480027178.3, Response filed Sep. 29, 2018 to Office Action dated Jun. 15, 2018", w/English claims, 9 pgs.
"Chinese Application Serial No. 201480027408.6, Office Action dated Jul. 24, 2018", W/English Translation, 15 pgs.
"Chinese Application Serial No. 201480027408,6, Response filed Nov. 6, 2018 Office Action dated Jul. 24, 2018", w/ English claims, 13 pgs.
"Chinese Application Serial No. 201480027655.6, Decision of Rejection dated Sep. 20, 2018", W/ English Translation, 8 pgs.
"Chinese Application Serial No. 201480027655.6, Response filed May 10, 2018 to Office Action dated Feb. 23, 2018", w/ English claims, 16 pgs.
"Chinese Application Serial No. 201480028053.2, Response filed Nov. 19, 2018 to Office Action dated Jul. 3, 2018", w/ English claims, 12 pgs.

(56) References Cited

OTHER PUBLICATIONS

"European Application Serial No. 10754613.7, Response filed Oct. 24, 2018 to Communication Pursuant to Article 94(3) EPC dated Jun. 26, 2018", 10 pgs.

"European Application Serial No. 14707069.2, Summons to Attend Oral Proceedings dated Oct. 10, 2018", 9 pgs.

"European Application Serial No. 14724817.3, Response filed Sep. 7, 2018 to Communication Pursuant to Article 94(3) EPC dated Apr. 5, 2018", 31 pgs.

"European Application Serial No. 14729994.5, Communication Pursuant to Article 94(3) EPC dated Jan. 4, 2019", 5 pgs.

Gabay, Cem, et al., "IL-1 pathways in inflammation and human diseases", Nat. Rev. Rheumatol. 6, 232-241, (2010), 10 pgs.

"Chinese Application Serial No. 201480027408.6, Response filed May 8, 2019 to Office Action dated Mar. 12, 2019", w English claims, 9 pgs.

"U.S. Appl. No. 15/616,548, Notice of Allowance dated May 23, 2019", 10 pgs.

* cited by examiner

TREATMENT OF PERIPHERAL VASCULAR DISEASE USING PROTEIN SOLUTIONS

CROSS-REFERENCE TO RELATED APPLICATION

This application is a continuation of U.S. patent application Ser. No. 13/841,103, filed on Mar. 15, 2013, now issued as U.S. Pat. No. 9,895,418, which is incorporated by reference herein in its entirety.

INTRODUCTION

The present technology relates to methods of treating peripheral vascular disease. In particular, methods comprise use of solutions comprising cytokines, including such solutions derived from blood and other tissues.

Peripheral vascular disease (PVD) is a disorder associated with the obstruction of arteries in peripheral tissue, i.e., not in the heart or brain. PVD can be associated with a variety of other disorders, including atherosclerosis, embolisms, diabetes, and hypertension.

PVD can be associated with pain, limping (claudication), and tissue loss (such as sores and ulcers) due to impaired blood flow. PVD is also often associated with subsisting cardiovascular disease.

Treatment of PVD is often directed to the underlying conditions causing PVD, such as athersclerosis and hypertension, using any of a variety of drug treatments. Angioplasty and similar procedures may also be performed to increase blood flow through the affected arteries.

However, many such treatments may present side effects, and may have limited long term utility as underlying conditions become worse. Accordingly, there remains a need to develop novel therapies for the treatment of PVD, particularly therapies that improve efficacy and have reduced side effects.

SUMMARY

The present technology provides methods and therapeutic compositions for the treatment of peripheral vascular disease (PVD). Methods include those comprising administering a blood-derived composition to the site of the PVD, the composition comprising at least two proteins selected from the group consisting of IL-1ra, sTNF-RI, sTNF-RII, IGF-I, EGF, HGF, PDGF-AB, PDGF-BB, VEGF, TGF-β1, and sIL-1RII, wherein the concentration of each protein in the composition is greater than the concentration of the protein in normal blood. For example, compositions may comprise
  (a) at least about 10,000 pg/ml IL1-ra;
  (b) at least about 1200 pg/ml sTNF-RI; and
  (c) a protein selected from the group consisting of sTNF-RII, IGF-I, EGF, HGF, PDGF-AB, PDGF-BB, VEGF, TGF-β1, and sIL-1RII, and mixtures thereof, wherein the protein has a concentration higher than the protein's baseline concentration in normal blood.
In some embodiments, the compositions further comprises a protein selected from the group consisting of sTNF-RII, IGF-I, EGF, HGF, PDGF-AB, PDGF-BB, VEGF, TGF-β1, and sIL-1RII, and mixtures thereof, wherein the concentration of the protein in the composition is greater than the concentration of the protein in normal blood. The compositions may also comprise white blood cells, platelets, bone marrow aspirate, and combinations thereof.

The present technology also provides methods for making compositions for treating PVD in a mammalian subject, comprising:
  (a) obtaining a cytokine cell suspension from the subject;
  (b) fractionating the liquid to produce an autologous protein solution comprising interleukin-1 receptor antagonist;
  (c) administering the autologous protein solution to the site of the PVD in the subject.
The cytokine cell suspension may comprise whole blood, bone marrow aspirate, adipose tissue, urine, fractions thereof, and mixtures thereof. For example, fractionating may comprise placing blood in a container a separator operable to separate the blood into two or more fractions; and centrifuging the separator to create a platelet-rich plasma fraction. The platelet-rich plasma may be contacted with a solid extraction material, such as polyacrylamide beads, to form the autologous protein solution.

The present technology also provides methods for treating PVD in a human or other mammalian subject, further comprising administering concentrated bone marrow aspirate (cBMA) with the Protein Solution. Such methods may comprise
  (a) obtaining bone marrow aspirate from the subject to be treated;
  (b) concentrating the bone marrow aspirate to produce a concentrated bone marrow aspirate (cBMA);
  (c) administering the cBMA to the subject.

DETAILED DESCRIPTION

Figure 1:
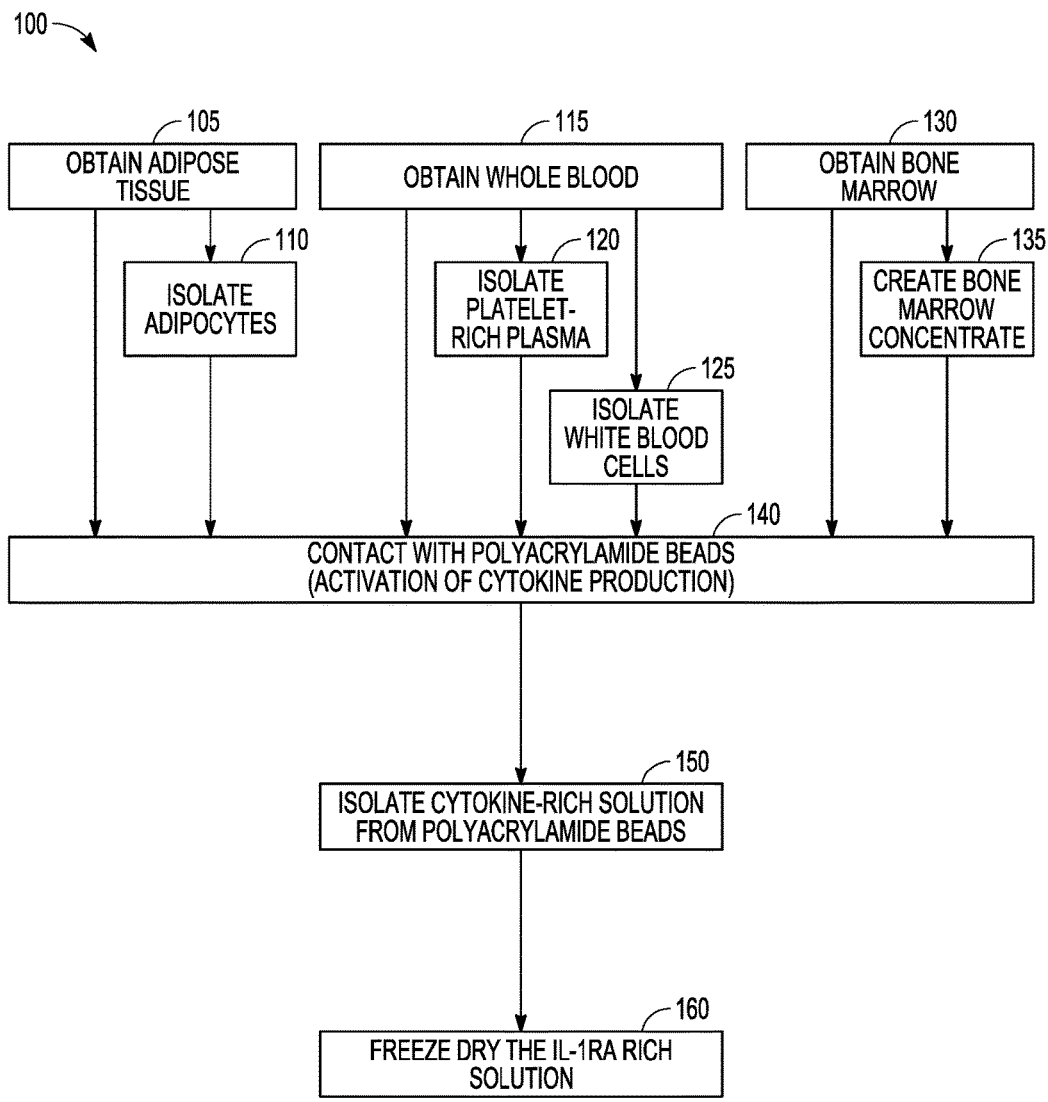
FIG. 1 is a block diagram illustrating a method for producing an anti-inflammatory cytokine composition.

The following description of technology is merely exemplary in nature of the composition, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The present technology relates to treating peripheral vascular disease (PVD) using compositions comprising proteins, including interleukin-1 receptor antagonist protein and other cytokines. In various embodiments, methods for treating PVD in a human or other mammalian subject, comprise:

(a) obtaining a cytokine cell suspension from one or more mammalian subjects;
(b) fractionating the liquid to produce protein solution comprising one or more proteins, such as interleukin-1 receptor antagonist; and
(c) administering the autologous protein solution to the site of the PVD in the subject.

Protein Compositions

The present technology provides methods for treating PVD in humans or other mammalian subjects using compositions (herein referred to as "Protein Solutions") comprising proteins dissolved, suspended or otherwise carried for delivery to a mammalian subject in a physiologically-acceptable medium. In various embodiments, such compositions comprise proteins (e.g., cytokines) that are native to whole blood in normal mammal subjects. Such compositions may also contain viable cells, including platelets, white blood cells, and combinations thereof.

In various embodiments, the Protein Solution comprises at least two proteins selected from the group consisting of IL-1ra (interleukin-1 receptor antagonist), sTNF-RI, sTNF-RII (soluble tumor necrosis factor-receptor 2), IGF-I (insulin-like growth factor 1), EGF (epidermal growth factor), HGF (hepatocyte growth factor), PDGF-AB (platelet-derived growth factor AB), PDGF-BB (platelet-derived growth factor BB), VEGF (vascular endothelial growth factor), TGF-β1 (transforming growth factor-β1, and sIL-RII (soluble interleukin one receptor II), wherein the concentration of each protein in the composition is greater than the concentration of the protein in normal blood. For the sake of clarity, the Protein Solution may contain three or more of the proteins from the recited group. While the concentration of every such protein in the composition may be greater than its respective concentrations in in normal blood, it is not necessary that the concentration of more than two of the proteins be greater than their respective concentrations in normal blood.

In various embodiments, the platelet-rich protein solution comprises the following components.

TABLE 1

Protein Solution Exemplary Protein Components

| Component | Composition Concentration | Normal Whole Blood Concentration |
|---|---|---|
| plasma proteins (total) | about 80 mg/ml or greater<br>about 100 mg/ml or greater<br>about 200 mg/ml or greater<br>about 250 mg/ml or greater | about 67 mg/ml |
| albumin | about 60 mg/ml or greater<br>about 100 mg/ml of greater | about 56 mg/ml |
| fibrinogen | about 3.2 mg/ml or greater<br>about 4 mg/ml or greater | about 2.9 mg/ml |
| IL-1ra | about 10,000 pg/ml or greater<br>about 25,000 pg/ml or greater<br>about 30,000 pg/ml or greater<br>from about 25,000 to about 110,000 pg/ml<br>from about 25,000 to about 40,000 pg/ml | about 4200 pg/ml |
| sTNF-RI | about 1,200 pg/ml or greater<br>about 1,800 pg/ml or greater<br>about 3,000 pg/ml or greater | about 630 pg/ml |
| sTNF-RII | about 3,000 pg/ml or greater<br>about 5,000 pg/ml or greater<br>about 7,000 pg/ml or greater<br>about 9,000 pg/ml or greater | about 1200 pg/ml |
| sIL-1RII | about 15,000 pg/ml or greater<br>about 20,000 pg/ml or greater<br>about 25,000 pg/ml or greater | about 11,800 pg/ml |

TABLE 1-continued

Protein Solution Exemplary Protein Components

| Component | Composition Concentration | Normal Whole Blood Concentration |
|---|---|---|
| Growth factors | | |
| EGF | about 800 pg/ml or greater<br>about 1,000 pg/ml or greater<br>about 1,200 pg/ml or greater | about 250 pg/ml |
| HGF | about 1,000 pg/ml or greater<br>about 2,500 pg/ml or greater<br>about 2,800 pg/ml or greater<br>about 3,000 pg/ml or greater | about 500 pg/ml |
| PDGF-AB | about 35,000 pg/ml or greater<br>about 50,000 pg/ml or greater<br>about 70,000 pg/ml or greater | about 6,000 pg/ml |
| PDGF-BB | about 10,000 pg/ml or greater<br>about 15,000 pg/ml or greater<br>about 20,000 pg/ml or greater | about 1,500 pg/ml |
| TGF-β1 | about 100,000 pg/ml or greater<br>about 150,000 pg/ml or greater<br>about 190,000 pg/ml or greater | about 10,000 pg/ml |
| IGF-1 | about 130,000 pg/ml or greater<br>about 150,000 pg/ml or greater<br>about 160,000 pg/ml or greater | about 70,000 pg/ml |
| VEGF | about 500 pg/ml or greater<br>about 600 pg/ml or greater<br>about 800 pg/ml or greater | about 150 pg/ml |

Protein concentrations can be measured using the methods set forth in Example 4.

The composition further preferably comprises viable white blood cells, lysed white blood cells, or both. In a preferred composition, the Protein Solution comprises monocytes, granulocytes, and platelets. In various embodiments, a Protein Solution comprises the following components.

TABLE 2

Protein Solution Exemplary Cellular Components

| Component | Composition Concentration | Normal Whole Blood Concentration |
|---|---|---|
| white blood cells | at least about 15 k/μl<br>at least about 30 k/μl<br>from about 30 to about 60 k/μl<br>from about 40 to about 50 k/μl | 6.5 k/μl |
| red blood cells | less than about 3 M/μl<br>less than about 2 M/μl<br>less than about 2.5 M/μl | 4.5 M/μl |
| platelets | at least about 400 k/μl<br>at least about 800 k/μl<br>at least about 1,000 k/μl | 240 k/μl |
| neutrophils | at least about 5 k/μl<br>at least about 10 k/μl<br>at least about 12 k/μl | 3.7 k/μl |
| monocytes | at least about 1 k/μl<br>at least about 2 k/μl<br>at least about 3 k/μl | 0.5 k/μl |
| lymphocytes | at least about 5 k/μl<br>at least about 10 k/μl<br>at least about 20 k/μl | 2 k/μl |
| eosinophiles | at least about 0.15 k/μl<br>at least about 0.18 k/μl | 0.1 k/μl |
| basophils | at least about 0.2 k/μl<br>at least about 0.4 k/μl<br>at least about 0.6 k/μl | 0.1 k/μl |

It will be understood that this concentration is species specific. Further, it is understood that concentrations may vary among individual subjects. Thus, in methods comprising production of a Protein Solution from the blood or other tissue containing cytokine-producing cells, the concentration of proteins and cells in the Protein Solution may vary from those recited above; the values recited above are mean values for concentrations as may be seen in a population of subjects.

In various embodiments, the concentration of one or more of the proteins or other components in the Protein Solution is greater than the concentration of the component in normal blood. (Compositions with such higher concentrations of components are said to be "rich" in such components.) As referred to herein, the concentration of a component in "normal" blood or other tissue is the concentration found in the general population of mammalian subjects from which the tissue is obtained. e.g., in normal whole blood. In methods wherein the anti-inflammatory cytokine composition is derived from tissue from a specific subject, the "normal" concentration of a protein or cell may be the concentration in the blood of that individual before processing is performed to derive the protein or cell.

Thus, in various embodiments, the concentration of one or more components of the Protein Solution is greater than about 1.5 times, about 2 times, or about 3 times, greater than the concentration of the component in normal blood. For example, components may have greater concentrations in the compositions, relative to normal (whole) blood, as follows:

IL-1ra, at a concentration that is at least about 2.5, or at least about 3 or at least about 5, times greater;
sTNF-RI, at a concentration that is at least about 2, or at least about 2.5 or at least about 3, times greater;
sTNF-RII, at a concentration that is at least about 2, or at least about 2.5 or at least about 3, times greater;
sIL-1RII, at a concentration that is at least about 1.5, or at least about 1.8 or at least about 2, times greater;
EGF, at a concentration that is at least about 2, or at least about 3 or at least about 5, times greater,
HGF, at a concentration that is at least about 2, or at least about 3 or at least about 4, times greater,
PDGF-AB, at a concentration that is at least about 2, or at least about 3 or at least about 5, times greater;
PDGF-BB, at a concentration that is at least about 2, or at least about 3 or at least about 5, times greater;
TGF-β1, at a concentration that is at least about 3, or at least about 4 or at least about 6, times greater;
IGF-1, at a concentration that is at least about 1.2, or at least about 1.4 or at least about 1.5, times greater;
VEGF, at a concentration that is at least about 2, or at least about 2.5 or at least about 3, times greater;
white blood cells, at a concentration that is at least about 2, or at least about 3 or at least about 4, times greater;
platelets, at a concentration that is at least about 2, or at least about 3 or at least 4, times greater,
neutrophils, at a concentration that is at least 1.5, or at least 2 or at least 3, times greater;
monocytes, at a concentration that is at least 3, or at least 4 or at least 6, times greater,
lymphocytes, at a concentration that is at least 5, or at least 8 or at least 10, times greater; and
basophils, at a concentration that is at least 2, or at least 4 or at least 6, times greater.

Also, the concentration of erythrocytes in the Protein Solution is preferably at least half, or at least a third, of the concentration of erythrocytes in normal blood.

For example, a Protein Solution may comprise:
(a) at least about 10,000 pg/ml IL1-ra;
(b) at least about 1,200 pg/ml sTNF-RI; and
(c) a protein selected from the group consisting of sTNF-RII, IGF-I, EGF, HGF, PDGF-AB, PDGF-BB, VEGF, TGF-β1, and sIL-1RII, and mixtures thereof, wherein the protein has a concentration higher than the protein's baseline concentration in normal blood. In another example, a Protein Solution comprises:
(a) interleukin-1 receptor antagonist (IL-1ra), at a concentration at least 3 times greater than the concentration of IL-1ra in normal blood;
(b) soluble tissue necrosis factor-r1 (sTNF-r1), at a concentration at least 2 times greater than the concentration of IL-1ra in normal blood;
(c) white blood cells at a concentration at least 2 times greater than the concentration of white blood cells in normal blood; and
(d) platelets, at a concentration at least 2 times greater than the concentration of platelets in normal blood.

In some embodiments, the concentration of IL-1ra in the Protein Solution is preferably at least 5.000, or at least 10,000, times greater than the concentration of interleukin-1α in the Protein Solution. The ratio of IL-1ra:interleukin-1β (IL-1 β) concentrations is preferably at least 100. In some embodiments, the concentration of IL-1ra in the Protein Solution is preferably at least 1500, or at least 8000, times greater than the concentration of IL-1 β in the Protein Solution. The ratio of sIL-1RII:interleukin-1β (IL-1 β) concentrations is preferably greater than 1. In some embodiments, the sIL-1RII in the Protein Solution is preferably at least 2000, or at least 45000, times greater the concentration of interleukin-1 β in the Protein Solution.

In various embodiments, the Protein Solution comprises one or more components (e.g., platelets) derived from the subject to whom the solution is to be administered in a treatment methods according to this technology. Such components are, accordingly, "autologous." In some embodiments, the Protein Solutions (e.g., Autologous Protein Solutions) consisting essentially of such autologous components. In other embodiments, one or more components of the solution may be obtained from non-autologous sources, such as through recombinant or synthetic methods, or by isolation from allogeneic sources (i.e., from subjects of the same species as the subject to whom the solution is to be administered) or xenogeneic sources (i.e., from animal sources other than the species to whom the solution is to be administered).

Methods of Making Protein Solutions

Protein Solutions may be made by any of a variety of methods, including admixture of individual components and processes wherein one or more components are derived from a source material. In various embodiments, the Protein Solution is made by fractionating a cytokine cell suspension, to produce a protein solution comprising IL1-ra.

Obtaining Protein Solutions by Contacting Cytokine-Producing Cells with an Extraction Material In various embodiments. Protein Solutions are made by derivation of one or more components from tissue comprising cytokine-producing cells. As referred to herein, a "cytokine producing tissue" is a tissue obtained from a mammalian subject, comprising cells that are capable of producing cytokines. Such cells include white blood cells, adipose stromal cells, bone marrow stromal cells, and combinations thereof. It is understood that white blood cells include monocytes, lymphocytes, and granulocytes such as neutrophils, eosinophils, and basophils. White blood cell useful in the methods of this technology preferably include monocytes and neutrophils. Cytokine producing tissues among those useful herein include blood, adipose tissue, bone marrow, and fractions thereof, as further discussed below.

Blood useful herein includes whole blood, plasma, platelet-rich plasma, platelet-poor plasma, and blot clots. In a preferred embodiment, methods of the present technology use platelet-rich plasma (PRP), containing white blood cells and platelets, comprising the buffy coat layer created by sedimentation of whole blood. Adipose tissue useful herein includes any fat tissue, including white and brown adipose tissue, which may be derived from subcutaneous, omental/visceral, mammary, gonadal, or other adipose tissue sites. Bone marrow useful herein includes red marrow and yellow marrow. In a preferred embodiment, bone marrow is bone marrow concentrate, obtained from the red marrow of long bones, comprising hematopoietic and mesenchymal stems cells. As discussed above, blood, adipose, and bone marrow tissue useful herein may be from either autologous or allogeneic sources, relative to the subject to be treated according to methods of this technology. Compositions may also be made from combinations of allogeneic and autologous tissues.

In some embodiments, methods comprise fractionating a liquid (a "cytokine cell suspension.") comprising cells capable of producing cytokines, such as IL1-ra and sTNF-R1. As discussed above, such cells include white blood cells, adipose stromal cells, bone marrow stromal cells, and combinations thereof. In some embodiments, the cytokine cell suspension is a liquid comprising white blood cells. It should be understood that the cytokine cell suspension comprises cells and an extra-cellular liquid, regardless of the relative proportions of the cells and liquid. In some embodiments, the suspension may comprise primarily cells, with liquid being present as only a minor component, essentially wetting the cells. In some embodiments, the liquid may comprise two phases, consisting of a phase primarily consisting of liquid and a phase primarily consisting of cells, forming a suspension of cells in the liquid only upon agitation or other mixing.

In some embodiments, fractionating a cytokine cell suspension comprises contacting the liquid with a solid extraction material. As exemplified in FIG. 1, such processes comprise:
 (a) obtaining a cytokine cell suspension, such as a liquid comprising white blood cells (steps 105, 115 or 135, or combinations thereof);
 (b) contacting the tissue with a solid extraction material (step 140); and
 (c) isolating a protein-containing liquid from the solid extraction material (step 150).

Obtaining the suspension 105, 115, 135 can comprise any of a variety of methods for creating a liquid containing cells among those known in the art. Such methods include isolation from tissue and culturing. Obtaining may be performed directly in the method, whereby a health care practitioner or other individual performs isolation, processing, culturing or other processes for creating the suspension, in a procedure that includes the contacting and isolating steps. In some embodiments, the processes for creating the suspension are performed contemporaneously with the contacting and isolating steps, as part of a point-of-care procedure, as discussed further herein. Alternatively, obtaining the suspension may be indirect, involving only the acquisition of the suspension for use in the contacting and isolating steps, wherein the processing to create the suspension has previously been performed by another party.

In various embodiments, obtaining comprises isolating a cytokine cell suspension, comprising white blood cells or other cytokine-producing cells, from blood, adipose tissue, bone marrow aspirate or other tissue comprising cytokine-producing cells, as exemplified in Steps 110, 120 and 125 of FIG. 1. Methods may comprise obtaining a cytokine cell suspension from two, three or more tissue sources.

Obtaining a Cytokine Cell Suspension from Blood

In embodiments comprising the use of blood, the blood may be used directly in contacting the solid extraction material, as exemplified in step 140 of FIG. 1, or may be processed to provide a blood fraction, such as PRP, in a preferred embodiment. Many devices and methods for creating blood fractions are known in the art, using such means as centrifugation and filtering.

In various embodiments, methods of the present technology comprise creating PRP as the cytokine cell suspension, using centrifugation. Such methods generally comprise placing blood in a container a separator operable to separate the blood into two or more fractions, and centrifuging the separator to create a platelet-rich plasma fraction. Such devices may include a tube and a buoy disposed in the tube, wherein the buoy has a density such that the buoy reaches an equilibrium position upon centrifugation of the tissue in the tube, the equilibrium position being between a first fraction and a second fraction comprising cytokine-producing cells, the second fraction having a concentration of cytokine-producing cells greater than the concentration of cytokine-producing cells in the first fraction. Such methods further comprise centrifuging the tube so that the buoy defines an interface between the first fraction and the second fraction comprising cytokine-producing cells. The second fraction is then collected for further use in the methods of this technology.

One such device useful herein is described in U.S. Pat. No. 7,992,725, Leach et al., issued Aug. 9, 2011. Such a device is commercially available as GPS III Platelet Concentrate and Separation System, from Biomet Biologics, LLC (Warsaw. Ind., USA). The device can be used in a clinical or laboratory environment to isolate fractions from a suspension or multi-component tissue material obtained from a subject, such as blood, bone marrow aspirate, cerebrospinal fluid, adipose tissue, Isolated fractions can include platelets, platelet poor plasma, platelet rich plasma and stromal cells. The isolated fractions can each have equilibrium point or positions within the separation container that are achieved when separation has occurred. For example, a buffy coat (PRP) of whole blood may have an equilibrium position above that of the red blood cells when a sample of whole blood is separated.

Figure 2:
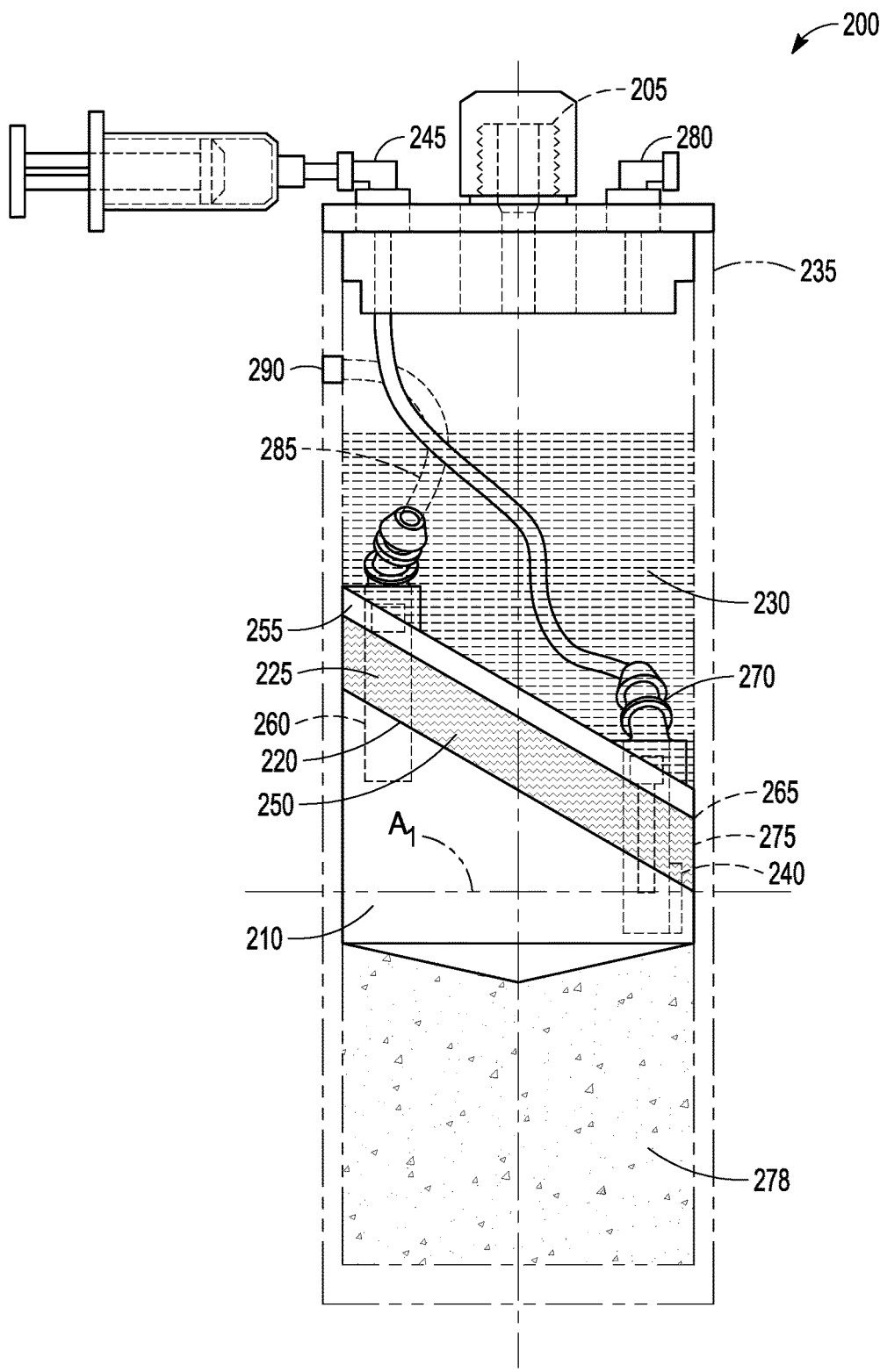
FIG. 2 is a diagram of a fractionation device.

The fractionation device 200 is exemplified in FIG. 2. The fractionation device 200 comprises a buoy 210 and a container wall 215. When the separation container 205 is centrifuged, the buoy perimeter 210a and the container wall 215 have clearance allowing the buoy 210 to move within the separation container 205 and a material to pass between the buoy perimeter 210a and the container wall 215. Alternatively, the buoy 210 could have an opening, such as a centrally or internally located opening or a peripheral channel running the height of the buoy, which would allow a material to move through the buoy.

The buoy 210 is carried in the separation container 205 and has a tuned density that is configured to reach a selected equilibrium position in a suspension. The buoy can have its density tuned in the range from about 1.0 g/cc to about 1.10 g/cc, such as about 1.06 g/cc. The buoy 210, according to various embodiments, can be formed to include the tuned density and can be formed of one or more materials to achieve the tuned density.

Referring to FIG. 2, a collection area 220 is positioned within the device 200 after a separation procedure has occurred. The collection area 220, defined relative to the buoy 210, is positioned at an equilibrium position of a separated or isolated middle fraction 225 in the container. The equilibrium position of a selected fraction can be defined as its position within the container relative to other fractions in the container of a separated sample or material. The equilibrium position can also be defined relative to the axis X of the buoy 210 or the container 12. The equilibrium position, however, may depend upon the amount of the sample of the amount of a selected fraction within a sample. According to the illustration in FIG. 2, the equilibrium position of the fraction 230 is above or nearer a top 235 of the device 200 than the equilibrium position of the fraction 225. Thus, the buoy 210 can be tuned, such as including a selected density or specific gravity, to position the collection area 220 relative to an equilibrium position of any selected fraction.

In some embodiments, the buoy 210 can comprise a collection port 240. The collection port 240 communicates with access port 245 and communicates with a collection space 220 above buoy upper surface 250 and can be located near the buoy perimeter 210a. In some embodiments, the collection port 240 is not carried on the buoy, but rather the collection port is a withdraw device such as a syringe that is inserted through an access port or top of the device 200.

According to various embodiments, an isolator 255, is coupled to the buoy 210. The combination of the isolator and buoy, according to various embodiments, can also be referred to as a separation assembly member. The isolator 255, for example, provides a means for creating the collection compartment 220 and comprises one or more spacers 260, 265 to position the isolator 255 apart from the buoy 210 to create the collection compartment 220. A withdraw port 270 can be carried on the isolator 255 communicating with the withdraw port 245 and the collection port 240. The spacer 260, 265 can also serve as a conduit 275 between the collection port 50 and a withdraw or withdraw port 245. The withdraw port 245 serves as a structure for withdrawing the isolated or second fraction 310 from the collection compartment 220.

After centrifuging the device 200 containing whole blood, the first fraction or top fraction 230, can be platelet-poor-plasma, the middle fraction 225 can be platelet-rich plasma or platelet concentrate, and a bottom fraction 278 can be red blood cells. Therefore, the fractionation method further comprises withdrawing a desired fraction from the device 200. Various ports 205, 245 and 280 can be provided to allow access to any appropriate compartment of the device 200. The access ports 205, 245, 280 can be any means that allow communication from outside the separation device 200 to the device's interior, such as a Luer lock port, a septum, a valve, or other opening. Additionally, collection vent tube 285 allows removal of a fractionated suspension in the collection area 220 through opening 290 without the need to remove the fraction, such as plasma, above the isolator 255. Although, without a collection vent tube 285, the fraction above the isolator could be removed and the collection area could be vented to the area above the isolator.

A method for using the fractionation device 200 can begin by inputting whole blood via an access port 205. The fractionation device 200 is placed into a centrifuge and spun for a period that is appropriate for fractionating whole blood. An exemplary period can be for about five minutes to about twenty minutes at a rate of about 320 rpm to about 5000 rpm. This speed may produce a selected gravity that may be approximately 7.17×g to about 1750×g (times greater than the normal force of gravity).

Other devices that may be used to isolate platelet-rich plasma described, for example, in U.S. Pat. No. 5,585,007, Antanavich, issued Dec. 17, 1996; U.S. Pat. No. 6,398,972, Blasetti et al., issued Jun. 4, 2002; U.S. Pat. No. 6,649,072, Brandt et al., issued Nov. 18, 2003; U.S. Pat. No. 6,790,371, Dolocek, issued Sep. 14, 2004; U.S. Pat. No. 7,011,852, Sukavaneshvar et al., issued Mar. 14, 2006; U.S. Pat. No. 7,179,391, Leach et al., issued Feb. 20, 2007; U.S. Pat. No. 7,374,678, Leach et al., issued May 20, 2008; U.S. Pat. No. 7,223,346, Dorian et al., issued May 29, 2007; and U.S. Pat. No. 7,708,152, Dorian et al., issued May 4, 2010.

In addition to the GPS® Platelet Concentrate and Separation Systems, a variety of other commercially available devices may be used to isolate platelet-rich plasma, including the Magellan™ Autologous Platelet Separator System, commercially available from Medtronic, Inc. (Minneapolis, Minn., USA); SmartPReP™, commercially available from Harvest Technologies Corporation (Plymouth, Mass., USA); the AutoloGel™ Process, commercially available from Cytomedix, Inc. (Rockville, Md., USA); the GenesisCS System, commercially available from EmCyte Corporation (Fort Myers, Fla., USA); the PCCS System, commercially available from Biomet 3i, Inc. (Palm Beach Gardens, Fla., USA); and the Arthrex ACP™ Double Syringe System, commercially available from Arthrex, Inc. (Naples, Fla., USA).

Referring again to FIG. 1, blood drawn from the patient may be mixed with an anticoagulant in one or more of Steps 115, 120, 125, and 130, so as to facilitate processing. Suitable anticoagulants include heparin, citrate phosphate dextrose (CPD), ethylenediaminetetraacetic acid (EDTA), anticoagulant citrate dextrose solution (ACD), and mixtures thereof. For example, the anticoagulant may be placed in the syringe used for drawing blood from the subject, or may be mixed with the blood after it is drawn.

A cytokine cell suspension may be prepared by admixing cells with a suitable liquid, as shown in step 125, using methods known in the art. For example, white blood cells may be isolated from whole blood by lysing red blood cells or by centrifugation of whole blood utilizing a density gradient where the white blood cells sediment to the bottom of a centrifuge tube. An example of density centrifugation includes the Ficoll-Paque™ Plus (GE Healthcare Bio-Sciences, Piscataway, N.J., USA). In some cases, a density gradient may be used to further separate mononuclear and polymorphonuclear cells. Cytokine-producing cells may also be prepared from whole blood using filtration; an example includes the Acelere™ MNC Harvest System (Pall Life Sciences. Ann Arbor, Mich., USA). Cytokine-producing cells can also be obtained from bone marrow. The cytokine-producing cells may be then suspended in a suitable medium, such as plasma, so as to maintain their viability.

Other methods may be used to create platelet-rich plasma or other cytokine cell suspension. For example, whole blood can be centrifuged without using a buoy system, whole blood may be centrifuged in multiple stages, continuous-flow centrifugation can be used, and filtration can also be used. In addition, a blood component including platelet-rich plasma can be produced by separating plasma from red blood cells using a slow speed centrifugation step to prevent pelleting of the platelets. In other embodiments, the buffy coat fraction formed from centrifuged blood can be separated from remaining plasma and re-suspended to form platelet-rich plasma.

Obtaining a Cytokine Cell Suspension from Adipose Tissue

In embodiments comprising the use of adipose tissue, the adipose tissue may be used directly in contacting the solid extraction material, as exemplified in step 140 of FIG. 1, or the adipose tissue may be processed to provide isolated adipocytes in step 110. Cell fractions comprising adipose-derived stem cells are also useful in this method. In some embodiments, adipose tissue is derived from human subcutaneous fat isolated by suction assisted lipectomy or liposuction. Stromal cells may be isolated from the adipose tissue and/or tissue portions using any suitable method, including methods known in the art such as mechanical and breakdown centrifugation. Stromal cells can also be isolated using enzymatic digestion. For example, stromal cells can be isolated from lipoaspirate, treated by sonication and/or enzymatic digestion, and enriched by centrifugation. Stromal cells isolated from adipose tissue may be washed and pelleted.

For example, adipose tissue can be collected by suction-assisted tumescent liposuction inside a specialized collection container attached to suction hoses and to a liposuction cannula. The collection container can have a gauze-type grid filter that allows the tumescent fluid to pass through and retains the solid adipose tissue. After collecting the adipose tissue, the collection container is removed from the suction device and reattached to a centrifugation device. The filter unit may further contain a filter having approximately a 100 micrometer pore size. Once the collection container containing the adipose tissue is attached to the centrifugation device, the tissue is sonicated. After sonication, the entire apparatus is inserted into a centrifuge bucket and centrifuged at, for example, 300×g for 5 minutes. After centrifugation, the collection container together with the filter unit is detached and can be discarded. The pellet containing the stromal cells can then be re-suspended in biocompatible solutions, such as plasma, plasma concentrate and platelet-rich plasma.

Various methods and devices for isolating and/or fractionating adipose tissue and adipocytes include those as described by U.S. Pat. No. 7,374,678, Leach, issued May 20, 2008; U.S. Pat. No. 7,179,391 to Leach et al., issued Feb. 20, 2007; U.S. Pat. No. 7,992,725, Leach et al., issued Aug. 9, 2011; U.S. Pat. No. 7,806,276, Leach et al., issued Oct. 5, 2010; and U.S. Pat. No. 8,048,297, Leach et al., issued Nov. 1, 2011. A device, such as the GPS™ Platelet Concentrate System, commercially available from Biomet Biologics, LLC (Warsaw, Ind., USA), may be used to isolate adipocytes.

Obtaining a Cytokine Cell Suspension from Bone Marrow

In embodiments comprising the use of bone marrow, the marrow may be used directly in contacting the solid extraction material, as exemplified in step 140 of FIG. 1, or may be processed to provide a bone marrow concentrate, as in step 135. Many devices and methods for obtaining and concentrating bone marrow are known in the art.

An exemplary process for isolating and creating a bone marrow concentrate (cBMA) is diagrammed in FIG. 6. Generally, the method 600 may start in step 605 with obtaining a bone marrow aspirate volume. The bone marrow aspirate (BMA) may be obtained in any selected or generally known manner. For example, a selected region of bone, such as a portion near an operative procedure, may be used to obtain the bone marrow aspirate. Generally, an accessing device, such as a syringe and needle, may be used to access an intramedullary area of a selected bone. A small volume of the selected portion may be drawn from a plurality of locations to obtain an appropriate volume of BMA or selected fraction of the BMA.

Once a selected volume of the BMA is obtained in step 605, it may be separated and concentrated using a gravimetric separator. Separators among those useful herein are operable to separate a multi-component fluid that generally includes various components or constituents of varying densities that are commingled or mixed together, including those described above for separation of fractions from blood and adipose tissue. The separator may include a buoy that is of a selected density relative to BMA. Such separators include those described above for use in concentrating and isolating fractions from blood and adipose tissue, including those described in U.S. Pat. No. 7,374,678, Leach, issued May 20, 2008; U.S. Pat. No. 7,179,391 to Leach et al., issued Feb. 20, 2007; U.S. Pat. No. 7,992,725, Leach et al., issued Aug. 9, 2011; U.S. Pat. No. 7,806,276. Leach et al., issued Oct. 5, 2010; and U.S. Pat. No. 8,048,297, Leach et al., issued Nov. 1, 2011. A device, such as the GPS™ Platelet Concentrate System, commercially available from Biomet Biologics, LLC (Warsaw, Ind., USA), may be used to isolate adipocytes. Separators and methods that may be used to fractionate BMA at steps 610 and 615 are also described, for example, in U.S. Application Publication No. 2006/0278588, Woodell-May, published Dec. 14, 2006. The BMA may be positioned in a separator according to various embodiments in step 610. Once the BMA is positioned in the separator, a selected fraction of the BMA may be separated from the BMA in step 615.

Once the BMA is placed in the separator, separator is spun in a centrifuge in a range between about 1.000 and about 8,000 RPM. This produces a force between about 65 and about 4500 times greater than the force of normal gravity, as generally calculated in the art, on the separator and the BMA. At this force, the more dense material in a BMA sample is forced toward the bottom end of the tube. The separator can thus be used to remove nucleated cells from the bone marrow sample. In various embodiments, concentrated BMA has a concentration of nucleated cells that is at least 2, at least 3, at least 4, or at least 5 times the concentration of nucleated cells in BMA.

Obtaining a Cytokine Cell Suspension from Blood Clots

In other embodiments comprising the use of blood, a liquid comprising cytokine-producing cells may be trapped in a blood clot. Cell releasate can be generated from the blood clot by either compression ("squeezing"), clot disruption, or centrifugation. The blood clot can be made with or without anticoagulant and with or without exogenous thrombin by combining blood or a blood fraction with a clotting agent. Suitable clotting agents include thrombin (e.g., bovine, recombinant human, pooled human, or autologous), autologous clotting protein, and polyethylene glycol. Calcium may be in the form of a calcium salt, such as calcium chloride.

In some embodiments, the clotting agent comprises a clotting protein, which may be a clotting fraction derived from a blood obtained from the patient to be treated. A suitable clotting fraction can be obtained by a process of: loading whole blood or plasma with a calcium solution (e.g., calcium chloride in ethanol) into a blood isolation device; optionally heating the whole blood or plasma for at least about 20 minutes, at a temperature of at least about 20° C.; and isolating the clotting fraction. The isolating may be performed by centrifuging the heated whole blood or plasma. A suitable isolation device is commercially available as the Clotalyst® Autologous Thrombin Collection System (hereinafter "Clotalyst System"), sold by Biomet Biologics LLC. Warsaw, Ind., USA.

Figure 4:
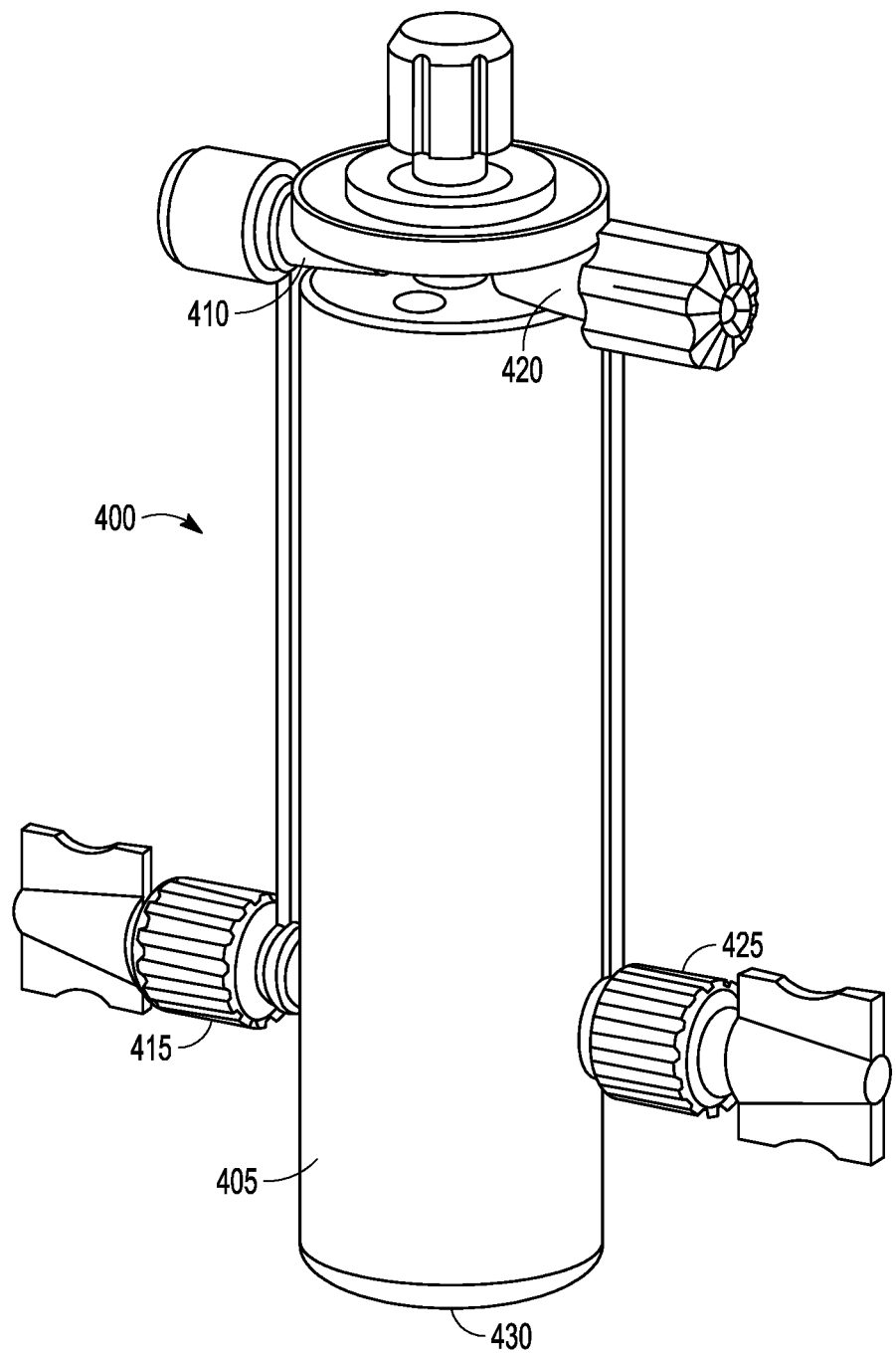
FIG. 4 is a diagram of a device for generating a blood clot.

An exemplary procedure for producing a clotting agent using a device 400 of FIG. 4 begins with injecting a reagent comprising calcium chloride and ethanol into the main chamber 405 through the first port 410. Glass beads are also placed in the main chamber 405. After the reagent has been injected, the first port 410 is closed using the first replacement cap 415. Blood with anticoagulant is injected into the main chamber 405 through the second port 420. After the blood has been injected, the second port 420 is closed using the second replacement cap 425. Optionally, the syringes and blood separation device 400 are pre-heated to a temperature of about 25° C.

The contents of the blood component separation device 400 are mixed by repeatedly inverting the device 400, e.g. about twelve times, so as to contact the blood with the glass beads. After mixing, the device is incubated The incubation process can be at a temperature and for a duration that will permit the contents of the device 400 to be heated at about 25° C. for about 15 minutes. Upon completion of the incubation period, a clotted mass of red blood cells, blood plasma, and glass beads forms at a second end 406 of the main chamber 405. After incubation is complete, the device 400 is shaken enough to dislodge and break-up any gel that may be present.

Obtaining a Cytokine Suspension Suspension Using Non-Centrifugal Methods

As noted above, the liquid containing white blood cells can be obtained by non-centrifugal means, such as by culturing. As referred to herein, a "non-centrifugal method" comprises a process for obtaining tissue fractions comprising cytokine-producing cells from tissue without use of a centrifuge. In some embodiments, methods are "non-gravimetric," wherein, based on physical, chemical or physicochemical properties of the cells other than density, wherein the concentration of white blood cells in the fraction are higher than the concentration of white blood cells in the tissue. Such non-gravimetric methods are, in particular, distinguished from methods wherein a white blood cell fraction is created by centrifugation of whole blood or other tissue. In some embodiments, the non-centrifugal method comprises a process solely based on such properties of white blood cells other than density. Non-centrifugal methods include filtration, antibody binding, and electrophoretic methods.

For example, as discussed above, white blood cells may be prepared from whole blood, bone marrow aspirate or other tissue, using filtration. White blood cells and other cytokine-producing cells obtained from blood, bone marrow, adipose tissue or other sources may also be cultured, using methods among those known in the art. The cells may be then suspended in a suitable medium, such as plasma, so as to maintain their viability and facilitate mixing or other contact with a solid extraction material. A liquid containing the cells may also be produced by compression or disruption of blood clots, as described above.

Contacting a Cytokine Cell Suspension with an Extraction Material and Isolating a Protein Solution In further reference to the exemplified process of FIG. 1, the cytokine cell suspension is incubated or otherwise contacted with a solid extraction material (step 140) to produce a protein-containing liquid. This liquid is then isolated (step 150) from the solid extraction material, as a Protein Solution of the present technology. Without limiting the scope, mechanism or function of the present technology, solid extraction materials useful herein concentrate cytokines or other proteins in the liquid volume of cytokine-producing cells and may, in some embodiments, activate, stimulate or otherwise increase production of cytokines, including IL-1ra. Thus, in some embodiments, methods comprising activating a cytokine cell suspension with a solid extraction material.

The solid extraction material can include various materials that provide a particular surface area to contact the cells. The solid extraction material may be a continuous material or may be discontinuous and comprise a plurality of separate particles. For example, the solid extraction material may be in the form of a plurality of beads, fibers, powder, a porous material, or a surface of a container comprising the liquid containing the cells. The solid extraction material may comprise geometric forms having various cross-sectional shapes, such as spherical, oval, or polygonal, among others. The solid extraction material can also comprise a continuous porous network, similar to a sponge, or can include a plurality of individual porous particles. The solid extraction material may also provide a larger surface area by being porous in comparison to a non-porous material.

In some embodiments, the solid extraction material includes particles having a large aspect ratio, for example, where the particles are needle-like in shape. The solid extraction material may also be formed as long fibers and may be or take a form similar to glass wool.

In some cases, the solid extraction material can comprise the internal walls of a container holding the cytokine cell suspension. For example, the solid extraction material may comprise the lumen of a syringe that contains the cytokine cell suspension. Other containers include tubes, such as centrifuge tubes, or a blood fractionation device or concentrator assembly as described elsewhere herein.

Where the solid extraction material is a continuous material, such as a porous sponge-like material, the solid extraction material can be used in an amount sufficient to absorb or adsorb or include substantially the entire liquid volume of cytokine-producing cells within the pores or interstices of the solid extraction material. Where the solid extraction material is a discontinuous material, such as a plurality of particles, the solid extraction material can be combined with the liquid containing the cells to form a slurry-like composition. The slurry can vary in consistency from paste-like, having a high-solids fraction, to a readily flowable slurry having a low-solids fraction.

The solid extraction material can provide a large surface area with which to contact the cells. However, in some cases, the solid extraction material can be further treated to increase its surface area, for example, by physically or chemically etching or eroding the surface of the solid extraction material. With respect to chemical etching, a corrosive agent can be used to modify the surface of the solid extraction material depending on the nature of the material. The modified surface may be produced by employing an alkali or an acid, for example chromosulphonic acid, in particular about 20% to about 80% in strength, preferably about 50% chromosulphonic acid. The solid extraction material can be incubated with the corrosive agent for about 5 min to about 30 min in order to chemically etch the surface and increase the surface area. The solid extraction material can then be washed to remove the corrosive agent. For example, the solid extraction material can include the internal walls of a container for holding the cytokine cell suspension where the internal walls are etched to subsequently increase the surface area in contact with the liquid.

Various polymers, metals, ceramics, and glasses can be used as the solid extraction material. In some embodiments, the solid extraction material comprises a hygroscopic material. Examples of suitable solid extraction material materials include glasses, minerals, polymers, metals, and polysaccharides. Minerals include corundum and quartz. Polymers include polystyrene, polyethylene, polyvinyl chloride, polypropylene, and polyacrylamide. Metals include titanium. Polysaccharides include dextran and agarose. A preferred solid extraction material comprises, or consists essentially of, polyacrylamide, as further described below.

The solid extraction material may comprise, for example, continuous solid extraction material of glass or a plurality of glass particles, glass wool, a continuous solid extraction material of metal such as titanium, a plurality of metal beads, metal powder, and combinations thereof. A continuous solid extraction material of metal can include a block or other three-dimensional shape formed of porous metal or metal alloys with an open cell structure. The solid extraction material may include various beads or particles of various sizes including substantially spherical beads. Beads include polystyrene beads, polyacrylamide beads, glass beads, metal (e.g., titanium) beads, or any other appropriate beads. Beads may be any size appropriate for the container and the amount of cytokine cell suspension being used. In some instances, bead sizes can range from about 0.001 millimeters to about 3 millimeters in diameter. Where the bead size is sufficiently small, the beads can appear more like a powder.

Polyacrylamide beads used as the solid extraction material can be formed by polymerizing acrylamide monomer using controlled and standardized protocols as known in the art to produce relatively uniform beads formed of polyacrylamide gel. In general, polyacrylamide is formed by polymerizing acrylamide with a suitable bifunctional crosslinking agent, most commonly N,N'-methylenebisacrylamide (bisacrylamide). Gel polymerization is usually initiated with ammonium persulfate and the reaction rate is accelerated by the addition of a catalyst, such as N,N,N',N'-tetramethylethylenediamine (TEMED). In various embodiments, polyacrylamide beads comprise 0.5 micromole of carboxyl groups per milliliter of beads, imparting a slight anionic character (negative charge). The beads are also typically resistant to changes in pH, and are stable in many aqueous and organic solutions. By adjusting the total acrylamide concentration, the polyacrylamide gel can be formed in a wide range of pore sizes. Moreover, the polyacrylamide beads can be formed in many sizes and can have relatively uniform size distributions. Bead size may range from several micrometers in diameter to several millimeters in diameter. For example, various types of Bio-Gel™ P polyacrylamide gel beads (Bio-Rad Laboratories, Hercules, Calif., USA) have particle sizes ranging from less than about 45 μm up to about 180 μm. Polyacrylamide beads are also available from SNF Floerger (Riceboro, Ga., USA). Pierce Biotechnology, Inc. (Rockford, Ill., USA), and Polymers. Inc. (Fayetteville, Ark., USA).

Once polymerized, polyacrylamide beads can be dried and stored in a powder-like form. The dry beads are insoluble in water but can swell considerably upon being rehydrated. Rehydration returns the polyacrylamide beads to a gel consistency that can be from about two to about three times the dry state size. Thus, dry polyacrylamide beads (i.e., desiccating polyacrylamide beads) may be used to absorb a portion of a liquid volume, including solutes smaller than the bead pore size, and can serve to concentrate IL-1ra and other proteins produced by the cytokine-producing cells. For example, combining dry polyacrylamide beads with the blood and/or platelet-rich plasma in step 230 activates production of IL-1ra by the cytokine-producing cells and also reduces the total liquid volume as the dry beads rehydrate and swell.

Without limiting the scope, mechanism or function of the present technology, it has been discovered that surface contact with the solid extraction material can activate the cells and the solid extraction material can, in some cases, assist in the separation and concentration of the resulting Protein Solution rich in cytokines, including IL-1ra. For example, in the case of a porous solid extraction material, a portion of the liquid comprising the cells can enter the pores and remain therein. Cells in the liquid may contact this additional surface area. In some embodiments, the pores are too small for the cells to enter, but a portion of the liquid can enter the pores. Liquid can be removed from the solid extraction material and pores by centrifuging, for example.

The solid extraction material is preferably sterilized, using techniques among known in the art, in order to prevent contamination of the cytokine cell suspension. For example, heat and pressure sterilization methods, such as autoclaving, may be used depending on the particular composition of the solid extraction material. Alternative methods, such as chemical sterilization or irradiation, can be used where the solid extraction material may be adversely affected by the autoclaving process.

In some embodiments, the cytokine cell suspension is incubated with solid extraction material for a time effective to remove a portion of the liquid. The incubation may be carried out over a period from about 30 seconds to about 72 hours and may be carried out at a temperature from about 20° C. to about 41° C. For example, the incubation may be 24 hours or less, 10 hours or less, 5 hours or less, 2 hours or less, 1 hour or less, 30 minutes or less, 15 minutes or less 10 minutes or less, 5 minutes or less, 4 minutes or less, 3, minutes or less, or 2 minutes or less. Incubation may be at least about 15 seconds, at least about 30 seconds, at least about 1 minutes, at least about 90 seconds, at least about 2 minutes, at least about 10 minutes, or at least about 30 minutes. In some embodiments, incubation s from about 1 minute to about 3 minutes. In some embodiments the liquid is not incubated, but is contacted with the solid extraction material for only so long as necessary to perform subsequent processing. The contacting may occur at ambient conditions, e.g., at a temperature of about 20-25° C.

In some embodiments, the cytokine cell suspension and the solid extraction material are agitated to more thoroughly mix these components during contact. The agitation may be accomplished by inverting, shaking, rocking, stirring, or vortexing the liquid and solid extraction material. Agitation may increase contact of the cells within the liquid with the solid extraction material. Agitation may be performed once, repeated multiple times, repeated periodically, or may be continuous. The liquid comprising the cells and the solid extraction material may also be agitated while the liquid is stimulated with the electromagnetic field. Additional aspects and features relating to producing protein-rich solutions using polyacrylamide beads and other solid extraction materials are described in: U.S. Patent Application Publication No. 2009/0220482, Higgins et al., published Sep. 3, 2009; U.S. Patent Application Publication No. 2010/0055087, Higgins et al., published Mar. 4, 2010; U.S. Patent Application Publication 2011/0052561, Hoeppner, published Mar. 3, 2011; International Application Publication 2012/030593, Higgins et al., published Mar. 8, 2012; and U.S. Patent Application Publication 2012/0172836, Higgins et al., published Jul. 5, 2012. Compositions and methods useful in aspects of the present technology are also described in the following applications filed concurrently with this disclosure: U.S. patent application Ser. No. 13/840,562, Binder et al., filed on Mar. 15, 2013, Methods and Non-Immunugenic Compositions for Treating Inflammatory Diseases; U.S. patent application Ser. No. 13/841,083, Landrigan, et al., filed on Mar. 15, 2013, Treatment of Inflammatory Respiratory Disease Using Protein Solutions; U.S. patent application Ser. No. 13/837,005, Woodell-May et al., filed on Mar. 15, 2013, Methods and Acellular Compositions for Treating Inflammatory Disorders; U.S. patent application Ser. No. 13/837,480, O'Shaughnessey, et al., filed on Mar. 15, 2013, Treatment of Pain Using Protein Solutions; U.S. patent application Ser. No. 13/839,280, Leach et al., filed on Mar. 15, 2013, Methods for Making Cytokine Compositions from Tissue Using Non-Centrifugal Methods; and U.S. patent application Ser. No. 13/840,129, Matusuka, et al., filed on Mar. 15, 2015, Treatment of Collagen Defects Using Protein Solutions, all of which are incorporated by reference herein.

Contacting of the cytokine cell suspension with the solid extraction material may be performed using a suitable container or other apparatus to effect the contact. Contacting may be performed in a continuous process wherein a flow of the liquid is passed over or through the solid extraction material, or the liquid and solid extraction material may be contained in a vessel. As discussed above, the vessel may comprise the solid extraction material, or may merely serve as a container holding the beads or other forms of the material. Containers useful in the present technology include those known in the art, such as the Plasmax™ Plus Plasma Concentrator, commercially available from Biomet Biologics, LLC (Warsaw, Ind., USA) and may include those devices and methods of use as described in U.S. Pat. No. 7,553,413, Dorian et al., issued Jun. 30, 2009; and U.S. Pat. No. 7,694,828, Swift et al., issued Apr. 13, 2010.

Figure 3A:
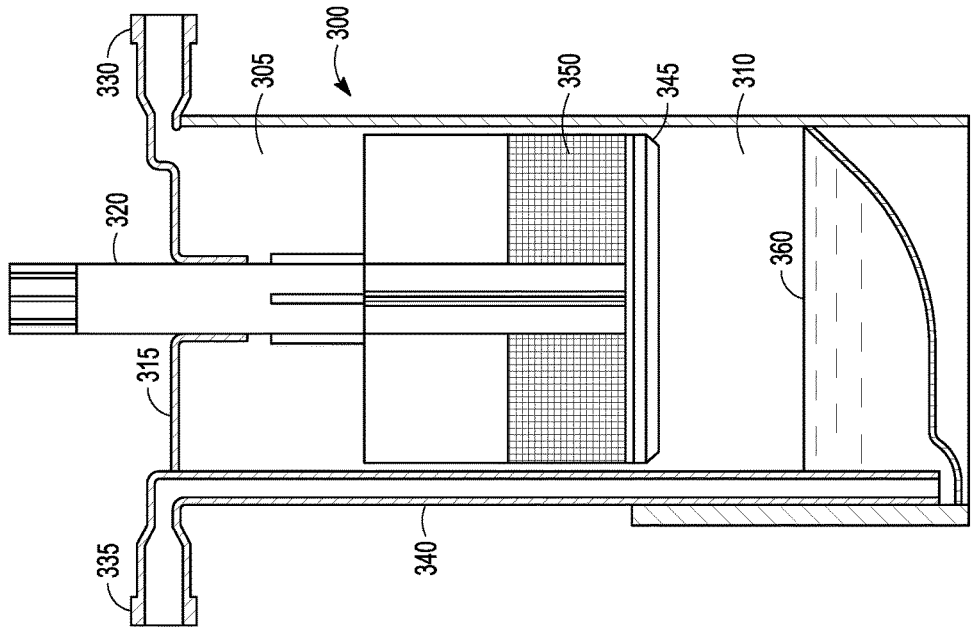
FIG. 3 shows a device for activating a sample to generate anti-inflammatory cytokines, before (FIG. 3A) and after (FIG. 3B) centrifugation.
Figure 3B:
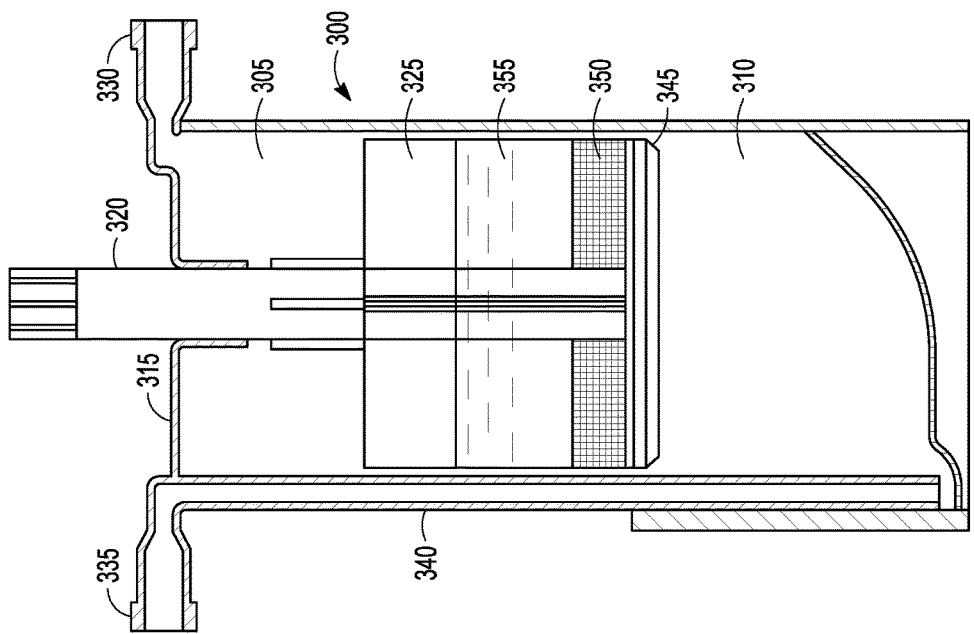

Such a device is shown in FIGS. 3A and 3B, for exemplary use with a polyacrylamide gel bead solid extraction material. The device 300 has an upper chamber 305 and a lower chamber 310. The upper chamber 305 has an end wall 315 through which the agitator stem 320 of a gel bead agitator 325 extends. The device 300 also has an inlet port 330 that extends through the end wall 315 and into the upper chamber 305. The device 300 also includes an outlet port 335 that communicates with a plasma concentrate conduit 340. The floor of upper chamber 305 includes a filter 345, the upper surface of which supports desiccated concentrating polyacrylamide beads 350.

During use, a fluid 355 containing cytokine-producing cells and, optionally, platelets is injected to the upper chamber 305 via the inlet port 330 and mixed with the polyacrylamide beads 350. The fluid 355 and polyacrylamide beads 350 may be mixed by rotating the agitator stem 320 and the gel bead agitator 325, to help mix the fluid 355 and beads 350. The mixed fluid 355 and polyacrylamide beads 350 are then incubated for the desired time at the desired temperature. The device 300 is then centrifuged so that liquid passes to the lower chamber 310 while the polyacrylamide beads 350 are retained by a filter 345, thereby separating the polyacrylamide beads 350 from the resulting solution 360 of IL-ra and other proteins that collects in the lower chamber 310. The solution 360 may be removed from the device via outlet port 335.

In some embodiments, a Protein Solution can be made in a process wherein a cytokine cell suspension is isolated from a tissue and then contacted with a solid extraction material in a continuous process. Referring again to FIG. 1, in some embodiments the isolating 110, 120, 135 and contacting 140 are performed using a single apparatus, referred to herein as a single separation and concentration device ("S/C device"). One such device is described in U.S. patent application Ser. No. 13/434,245, O'Connell, filed Mar. 29, 2012.

Figure 5:
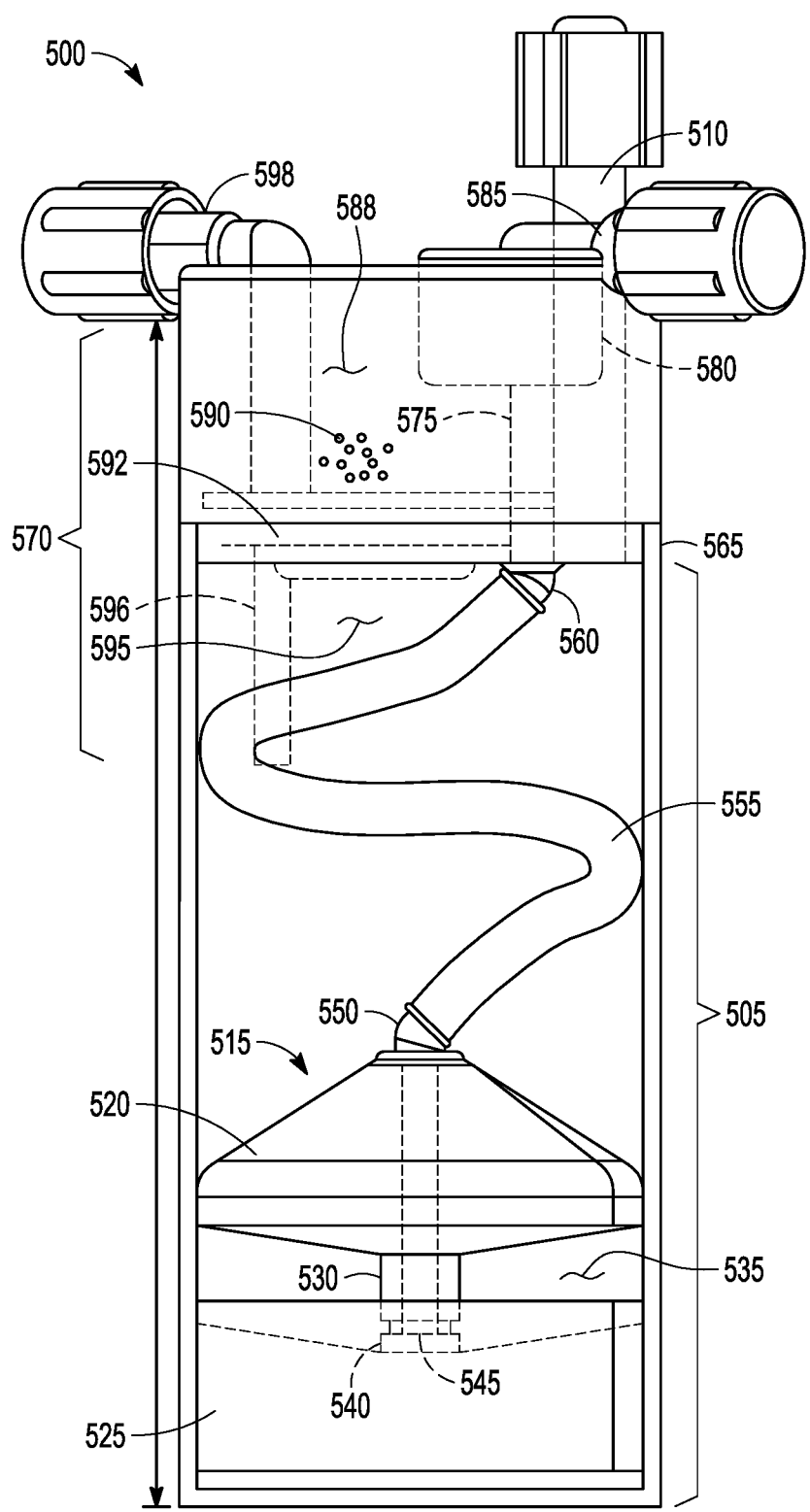
FIG. 5 is a diagram of a single device capable of generating an anti-inflammatory cytokine composition;
Corresponding reference numerals indicate corresponding parts throughout the several views of the drawings. It should be noted that the figures set forth herein are intended to exemplify the general characteristics of materials, compositions, devices, and methods among those of the present technology, for the purpose of the description of certain embodiments. These figures may not precisely reflect the characteristics of any given embodiment, and are not necessarily intended to fully define or limit specific embodiments within the scope of this technology.

The S/C device comprises a separation region, a first concentration region, a second concentration region, a buoy system, an inlet port, a check valve, a first withdrawal port and a second withdrawal port. FIG. 5 shows an S/C device 500 capable of generating an anti-inflammatory cytokine composition from whole blood. For example, the method may start with obtaining a volume of whole blood, which is filled into a separation region 505 of the S/C device 500 by injecting through the inlet port 510. A buoy system 515 is located within the separation region 505. The buoy system comprises a first buoy member 520, a second buoy member 525, and a third buoy member 530 that couples the first buoy member 520 to the second buoy member 525. A space between the first and second buoy members 520, 525 defines a buoy separation region 535. A density of each buoy member can be selected depending on what blood fraction is desired as a result of a separation. The buoy system 515 can include a selected buoy system, such as the buoy system generally used in the GPS® II or GPS®III gravity platelet separation system sold by Biomet Biologics, LLC. (Warsaw, Ind., USA). Buoy systems are disclosed in U.S. Pat. Nos. 7,845,499 and 7,806,276, and 7,992,725.

A method for obtaining a Protein Solution comprises spinning the S/C device 500 by centrifugation. Centrifugal forces allow the buoy system 515 to move through the whole blood, resulting in a fraction of the whole blood to be located in the buoy separation region 535. For example, this fraction may comprise platelet-rich plasma. With a use of a withdrawal syringe, the selected fraction can be removed from the collection volume 535 through the third buoy member 530 that defines a removal passage 540 that is connected with collection face passages 545. A connection elbow 550 can interconnect with the removal passage 540 to allow a vacuum to be formed through the connection elbow 550, the collection passage 540, and the buoy collection passages 545. A collection tube 555 can interconnect the connection elbow 550 with a withdrawal elbow 560 that extends from a wall 565 that can be a bottom wall of concentration region 570. A second withdrawal tube 575 can be first connected with a check valve assembly 580 and a first withdrawal port 585. The first withdrawal port 585 can be connected with the withdrawal syringe with a Luer lock type connection or other appropriate connection.

The check valve assembly 580 ensures the fraction being removed flows in one direction and prevents the fraction being removed from reentering the second withdrawal tube 575. Furthermore, when material is pushed back into the check valve assembly 580 from the first withdrawal port 585, such that material will enter the concentration region 570, a disc within the check valve 580 can flex down towards the second withdrawal tube 575 and close an opening and thereby open a second opening within the check valve assembly 580. The second opening allows the fraction to be pushed into the concentration region 570.

Therefore, the blood fraction is then re-injected through the first withdrawal port 285, through the check valve assembly 580, and into an upper volume 588 of the concentration region 570. Polyacrylamide beads 590 are added to the blood fraction in the upper volume 588 and the blood fraction and the polyacrylamide beads 590 can be mixed by shaking. Optionally, the blood fraction and the beads 590 can be incubated for a selected period of time before proceeding with the method.

The method comprises a second step of spinning by centrifugation. During the second centrifugation, the anti-inflammatory cytokine composition is separated from the beads 590 by being forced through a filter 592 and into a lower concentration region 595 of the concentration region 570. The Protein Solution can be withdrawn through a third withdrawal tube 596 and out a second withdrawal port 598 by use of a second withdrawal syringe. Again, the syringe can be connected to the second withdrawal port by a Luer® lock type connection.

Referring again to FIG. 1, following contacting the liquid with the solid extraction materials, a Protein Solution is isolated, as indicated at step 150. Isolation may be accomplished by drawing off at least a portion of the liquid volume and leaving the beads. In some cases, the extraction material may be sedimented by centrifugation prior to drawing off the Protein Solution. Isolation may also be performed by filtration, where the material is retained by a filter and the Protein Solution passes through the filter using centrifugal force or by using vacuum, for example. If the incubation with extraction material utilizes dry polyacrylamide beads, the liquid volume may be reduced as the beads swell upon rehydration, thereby concentrating the resulting Protein Solution. To maintain the increased concentration, care should be taken in the isolation step so as to avoid compressing the beads or drawing liquid out from the swollen beads. For example, high centrifugal force or high vacuum may collapse the beads and/or draw liquid out of the internal volume of the beads.

Optional Electromagnetic Stimulation

The cytokine cell suspension can be stimulated with an electromagnetic field, before or during the contacting of the liquid with a solid extraction material. Thus, in some embodiments, stimulation of the liquid comprising the cells can be performed prior to contacting the liquid and the solid extraction material. However, it is preferred that at least a portion of the contacting step and at least a portion of the stimulating step overlap in time such that the liquid comprising the cells is concurrently in contact with the solid extraction material and stimulated with the electromagnetic field.

Stimulating the cytokine cell suspension with an electromagnetic field may involve various forms of electromagnetic stimulation, such as a pulsed electromagnetic field or a capacitively coupled electromagnetic field. In some embodiments, the liquid is stimulated using a power source coupled to a stimulation coil. The current passing through the coil produces a pulsing magnetic field which induces in the liquid a pulsing electric field. The coil may partially surround the liquid as it is held within a container, such as a tube or syringe. The coil may be integrated into to the container holding the cytokine cell suspension or may be removable. For example, a plastic tube can be formed with an integrated coil or the coil can be temporarily coupled to the container or placed within the container, for example, the tube can be configured so that the coil can be snapped onto the container. The power source can be coupled to the coil as needed to perform the stimulating step.

Stimulation of the liquid with an electromagnetic field may also include placing at least two electrodes across the liquid. Electrical energy may then be applied to the electrodes so as to capacitively couple the electrodes and generate the electromagnetic field there between. The electromagnetic field is therefore able to pass through the liquid so as to increase the rate and/or amount of cytokine production. In other embodiments, electrodes can be used to produce a direct current or one or more coils can be used to produce a pulsed electromagnetic field.

The strength of the electromagnetic field during stimulation can be at least about 0.5 microvolts per centimeter, whether produced by direct current, capacitively coupled current, or pulsed electromagnetic field. In the case of a direct current electrode, the amplitude of the current can be from about 1 to about 200 microamperes, and in some embodiments, the amplitude may be from about 20 to about 100 microamperes. In still further embodiments, the current may be about 20, about 60, or about 100 microamperes. It should be understood, however, that the amplitude of the current may be of other suitable magnitudes.

The electromagnetic field applied during the stimulating step may be constant or vary over time. For example, a sinusoidal time varying electromagnetic field can be applied using the electrodes placed across the liquid. Such a sinusoidal time varying electromagnetic field can have a peak voltage across the electrodes from about 1 volt to about 10 volts, and in some embodiments, the peak voltage can be about 5 volts. The corresponding electric field produced can have an amplitude of from about 0.1 millivolt per centimeter (mV/cm) to about 100 mV/cm, and in some embodiments can be about 20 mV/cm. The sinusoidal time varying electric field may have a frequency of from about 1,000 Hz to about 200,000 Hz. and in some embodiments the frequency may be about 60,000 Hz.

The electromagnetic field applied to the liquid may also be a pulsed electromagnetic field. The pulsed electromagnetic field can be induced using an external coil and a pulse generator. In this regard, a pulsed electromagnetic field may have a pulse duration of from about 10 microseconds per pulse to about 2000 microseconds per pulse. The pulse duration in one embodiment can be about 225 microseconds. The pulses may include electromagnetic bursts, in which a burst can comprise from 1 pulse to about 200 pulses. Alternatively, the electromagnetic field may have bursts that comprise from about 10 pulses to about 30 pulses. In this regard, in one embodiment each burst may comprise about 20 pulses.

The frequency at which bursts in the pulsed electromagnetic are applied may vary. In this regard, bursts can be repeated at a frequency of from about 1 Hz to about 100 Hz in some embodiments, and can be repeated at a frequency of about 10 Hz to about 20 Hz in other embodiments. Furthermore, bursts can repeat at a frequency of about 1.5 Hz, about 15 Hz or about 76 Hz. A burst can have a duration from about 10 microseconds up to about 40,000 microseconds. In this regard, a burst can have a duration of about 4.5 milliseconds.

Suitable devices for generating a capacitively coupled electromagnetic field include SpinalPak® spinal stimulator (EBI, L.P., Parsippany, N.J.) or a DC stimulation device such as an SpF® XL IIb spinal fusion stimulator (EBI, L.P., Parsippany, N.J.). Pulsed electromagnetic fields can be produced using various known methods and apparatuses, such as using a single coil or a pair of Helmholtz coils. For example, a suitable apparatus includes the EBI Bone Healing System® Model 2001 (EBI, L.P., Parsippany, N.J.) and the BTBS stimulation coil. With respect to direct current, an electric field may be generated using any known device for generating a direct current electric field, such as for example, the Osteogen™ implantable bone growth stimulator (EBI, L.P., Parsippany. N.J.). Other suitable devices for generating electromagnetic fields may be used.

Electromagnetic stimulation of the cytokine cell suspension can be continued and/or repeated as desired with respect to contacting the liquid and the solid extraction material. It should be understood, however, that the step of stimulating the liquid with an electromagnetic field includes fields other than, or in addition to, electric or electromagnetic fields associated with ambient conditions (such the electromagnetic fields generated by casual exposure to radios, telephones, desktop computers or similar devices).

In some embodiments, both the contacting and stimulating steps as shown in FIG. 1 are performed in less than about 1 hour. The contacting and stimulating steps can also be performed at temperatures ranging from about 20° C. to about 37° C. In a preferred embodiment, the temperature of the cytokine cell suspension is kept at about 37° C. during the contacting and stimulating steps. One or both of the contacting and stimulating steps are typically performed ex vivo.

Other Methods for Forming Protein Solutions

The present technology provides other methods for forming Protein Solutions, such as the admixture of proteins and other components and the isolation and concentration of proteins and components without using solid extraction materials. Protein Solutions of the present technology can be made entirely comprising proteins made by such methods, or by addition of proteins made by such methods with components or solutions made by tissue isolation and processing with solid extraction materials, as described above.

For example, various methods provide acellular or substantially acellular Protein Solutions, comprising one or more proteins as described above. Without limiting the scope, mechanism or function of the present technology, such acellular anti-inflammatory cytokine compositions may offer advantages in certain applications, insofar as they may not create an immunogenic response in subjects to whom they are administered.

In particular, by way of example, a Protein Solution may comprise interleukin-1 receptor antagonist (IL-1ra) that is synthetic or recombinant, or isolated from autologous, allogeneic or xenogeneic blood or other biologic sources, aside from the methods described above. For example, Kineret™ (anakinra) is a recombinant, non-glycosylated form of IL-1ra, sold by Amgen Manufacturing, Ltd. (Thousand Oaks, Calif.). Various recombinant interleukin-1 inhibitors and methods of treatment are described in U.S. Pat. No. 6,599,873, Sommer et al., issued Jul. 29, 2003; U.S. Pat. No. 5,075,222. Hannum et al., issued Dec. 24, 1991; and U.S. Application Publication No. 2005/0197293, Mellis et al., published Sep. 8, 2005. In addition, methods for producing IL-1ra from body fluids, including the use of autologous fluids, are described in U.S. Pat. No. 6,623,472, Reinecke et al., issued Sep. 23, 2003; U.S. Pat. No. 6,713,246, Reinecke et al., issued Mar. 30, 2004; and U.S. Pat. No. 6,759,188, Reinecke et al., issued Jul. 6, 2004. When an allogeneic anti-inflammatory cytokine composition is to be generated, multiple sources of IL-1ra from multiple subjects may be pooled together.

More generally, methods for making acellular Protein Solutions can comprise culturing cells in a cell culture that either naturally produce anti-inflammatory cytokines, such as IL-1ra, or cells that are engineered to produce such cytokines. Non-limiting examples of cells that naturally produce anti-inflammatory cytokines include adipose tissue cells, adipocytes, adipose-derived stem cells, stromal cells, bone marrow cells, mesenchymal stem cells, and blood cells.

In various embodiments, cell lines can be engineered to overproduce an anti-inflammatory cytokine. Non-limiting examples of anti-inflammatory cytokines include VEGF, TNF-α, IL-1ra, sTNF-RI, sTNF-RII, PGDF-AB, PDGF-BB, IGF-I, EGF, TGF-β1, sIL-1RII, and HGF. Stable eukaryotic cell lines can be generated that overexpress an anti-inflammatory cytokine by transfecting eukaryotic cells, such as mammalian cells, with recombinant DNA comprising a gene encoding an anti-inflammatory cytokine and a selectable marker. Alternatively, prokaryotes and yeast can be engineered to overexpress an anti-inflammatory cytokine by transformation with recombinant DNA comprising a gene encoding an anti-inflammatory cytokine and a selectable marker. Transformations and transfections can be performed with recombinant DNA molecules comprising a DNA sequencing encoding an anti-inflammatory cytokine, such as IL-1ra, and a selectable marker. Eukaryotic and prokaryotic cells can be engineered to overexpress the anti-inflammatory cytokine constitutively or by induction. Methods for expressing anti-inflammatory cytokines, such as IL-ra, sTNF-RI, and sTNF-RII, and sIL1-RII in eukaryotic and prokaryotic cells are described in U.S. Pat. No. 6,337,072, Ford et al., issued Jan. 8, 2002; and U.S. Application Publication No. 2001/0053764, Sims et al., published Dec. 20, 2001.

When a IL-1ra gene is transcribed in humans, the mRNA can be spliced into four variants, resulting in four isoforms of translated IL-1ra. SEQ ID NOs: 1, 3, 5, and 7 are the cDNAs for IL-1ra isoforms 1-4 respectively, and SEQ ID NOs: 2, 4, 6, and 8 are the amino acid sequences of IL-1ra isoforms 1-4 respectively. Collectively, the IL-1ra isoforms are referred to as "IL-1ra." SEQ ID NO: 9 is the cDNA sequence for sTNF-RI and SEQ ID NO: 10 is the amino acid sequence for sTNF-RI. SEQ ID NO: 11 is the cDNA sequence for sTNF-RII and SEQ ID NO:12 is the amino acid sequence for sTNF-RII. SEQ ID NO:13 is the cDNA sequence for sIL-1RI and SEQ ID NO:14 is the amino acid sequence for sIL-1RI. SEQ ID NOs 15 and 17 are the cDNAs for sIL-1RIIv1 and sIL-1RIIv3 respectively, and SEQ ID NOs:16 and 18 are the amino acid sequences for sIL-1RIIv1 and sIL-1RIIv3 respectively. The cDNA sequence for IL-1RIIv2 is a non-coding sequence; therefore, it is not included.

To express either IL-1ra, sTNF-RI, or sTNF-RII (generically referred to as a "protein of interest") in a prokaryotic culture, for example in a particular bacteria, a cDNA sequence (SEQ ID NOs: 1, 3, 5, 7, 9, 11, 13, 15, or 17) is cloned into an expression vector suitable for the bacteria. The expression vector should comprise a strong promoter, and a selectable marker, such as antibiotic resistance. Non-limiting examples of antibiotics capable of killing bacteria cells include ampicillin, tetracycline, kanamycin, and chloramphenicol. The expression vector should further comprise elements that result in constitutive or inducible expression of the protein of interest. Optionally, a DNA sequence corresponding to a tag functionally coupled to the protein of interest that allows for identification and purification of the protein can be present in the vector adjacent to the gene for the protein of interest. For example, an N or C-terminal His tag can be used to detect proteins with anti-His antibodies, and they allow for purification on nickel columns. When the expression vector comprising a gene expressing a protein of interest is prepared, a bacteria cell, for example E. coli, can be transformed with the expression vector. The selectable marker ensures that only cells transformed with the vector will survive in LB broth supplemented with an antibiotic corresponding to the selectable marker. The bacteria can then be grown in LB broth supplemented with the antibiotic for expression and purification. Expression vectors, methods for cloning a protein of interest into an expression vector, methods for transforming prokaryotic cells, methods for expressing protein from transformed prokaryotic cells, and protein purification methods are commonly known by those with ordinary skill in the art.

To express a protein of interest in a eukaryotic culture, for example in mammalian cells, a cDNA sequence (SEQ ID NOs: 1, 3, 5, 7, 9, 11, 13, 15, or 17) is cloned into an expression vector suitable for a particular mammalian cell. The expression vector should comprise a strong promoter, and a selectable marker, such as antibiotic resistance. Non-limiting examples of antibiotics capable of killing mammalian cells include geneticin and gentamicin. The expression vector should further comprise elements that result in constitutive or inducible expression of the protein of interest. Optionally, a DNA sequence corresponding to a tag functionally coupled to the protein of interest that allows for identification and purification of the protein can be present in the vector adjacent to the gene for the protein of interest. When the expression vector comprising a gene expressing a protein of interest is prepared, a mammalian cell, such as a human cell, can be transfected with the expression vector. Transfected cells can be grown in a cell culture medium supplemented with an antibiotic corresponding to the selectable marker. The presence of the antibiotic allows for the isolation of stable cell lines. Stable cell lines can then be grown in cell culture medium supplemented with antibiotic for expression and purification. Expression vectors, methods for cloning a protein of interest into an expression vector, methods for transfecting eukaryotic cells and developing stable cell lines, methods for expressing protein from transfected eukaryotic cells, and protein purification methods are commonly known by those with ordinary skill in the art.

Alternatively, eukaryotic cells that have not been genetically altered by DNA transfection can be cultured. The eukaryotic cells can be primary cultures, i.e. cells grown directly from a eukaryotic donor, such as a human, or the eukaryotic cells can be established cell lines. Many established cell lines are available commercially from American Type Culture Collection, Inc. (Manassas, Va., USA). The cells can be grown with or an exogenous signal, such as a recombinant protein. Eukaryotic cells are often cultured in culture flasks with cell culture medium. The cell culture medium can be recovered from the flasks, and centrifuged to remove any non-adherent cells.

A cell culture can be a monolayer culture, a non-adherent culture, or a bioreactor. A monolayer culture comprises anchorage-dependent cells that are cultured on a suitable substrate that allows cell adhesion and spreading, such as cell culture flasks and cell culture dishes. A non-adherent culture comprises cells that are maintained in a suspension. Suitable cells are either not anchorage-dependent, or they are anchorage-dependent cells that have been adapted for culture in a suspension. Many cell lines, for example many insect cells, can be grown in either a monolayer or a suspension. A bioreactor is a device that can support a biologically active environment in which chemical processes are carried out and/or biochemically active substances are derived. Bioreactors can include suspended or immobilized cells. Monolayer cultures, non-adherent cultures, and bioreactors can be maintained by methods commonly used in the art.

In some embodiments, the cell culture is subjected to an electromagnetic field, so as to stimulate the production of one or more proteins. Stimulating the culture with an electromagnetic field may involve various forms of electromagnetic stimulation, such as a pulsed electromagnetic field or a capacitively coupled electromagnetic field. Methods and conditions for stimulation include those discussed above.

Cell cultures can either release anti-inflammatory cytokines into culture medium naturally, or the cultures can be induced to release the anti-inflammatory cytokines into the culture medium. The culture medium can be isolated by aspiration, centrifugation or filtration to form the acellular anti-inflammatory cytokine composition.

In some embodiments, an anti-inflammatory cytokine is isolated from urine, for use in producing a Protein Solution of the present technology. Proteins can be isolated from urine by methods among those known in the art. One such method is employed in the ProteoSpin™ Urine Protein Concentration Maxi Kit sold by Norgen Biotek Corp. (Thorold, Ontario, Canada). This kit utilizes an ion exchange resin integrated into a spin column. Briefly, a urine sample is obtained and its pH adjusted to 3.5. The urine is then transferred to a spin column containing the ion exchange resin, which is placed in a collection tube. The column is then centrifuged, wherein the proteins attach to the resin, and the remaining fluids and salts flow into the collection tube and are discarded. The proteins are then washed by applying supplied column activation and wash buffer followed by centrifugation. The flow through is discarded and the wash procedure is repeated. An elution buffer (10 mM sodium phosphate, pH 12.5) is added to the column and neutralizer is added to an elution tube. The spin column containing the elution buffer is placed in the elution tube and centrifuged, whereby the proteins are eluted and captured in the elution tube containing neutralizer.

Therapeutic Compositions

The present technology also provides compositions comprising a Protein Solution and a second component comprising active materials, physiological carriers, and combinations thereof. In some embodiments, compositions comprise a safe and effective amount of the Protein Solution and a safe and effective amount of a second active. A "safe and effective" amount of a component is an amount that is sufficient to have the desired therapeutic effect in the human or other mammalian subject, without undue adverse side effects (such as toxicity, irritation, or allergic response), commensurate with a reasonable benefit/risk ratio when used in the manner of this technology. The specific safe and effective amount of the component will, obviously, vary with such factors as the particular condition being treated, the physical condition of the patient, the nature of concurrent therapy (if any), the specific components used, the specific route of administration and dosage form, the carrier (if any) employed, and the desired dosage regimen.

Active materials among those useful herein include biologics and pharmaceutical actives. Biologics include blood fractions, such as PRP, blood products, and concentrated bone marrow aspirate (cBMA).

Accordingly, in some embodiments, the present technology provides compositions comprising a safe and effective amount of a Protein Solution and a safe and effective amount of cBMA. cBMA can include hematopoietic, stem cells, stromal stem cells, mesenchymal stem cells, endothelial progenitor cells, red blood cells, white blood cells, fibroblasts, reticulocytes, adipose cells, or endothelial cells. As described above, the Protein Solution may be made using bone marrow aspirate as a cytokine containing tissue. However, a therapeutic composition may additionally comprise cBMA with Proteint Solution. In one embodiment, a therapeutic composition comprises a Protein Solution and cBMA in an Protein Solution:cBMA ratio of about 1:1, about 1:2, about 1:3, about 1:4, about 1:5, about 1:6, about 1:7, about 1:8, about 1:9 or about 1:10. Alternatively, the Protein Solution:cBMA ratio can be about 2:1, about 3:1, about 4:1, about 5:1, about 6:1, about 7:1, about 8:1, about 9:1 or about 10:1. The cBMA and Protein Solution may also be produced simultaneously. Thus, in reference to FIG. 1 and the processes described above, bone marrow aspirate may be added to the whole blood obtained in step 115, prior to or during the contacting with a solid extraction material in step 140; such a process involves operation of both steps 115 and 130. For example, bone marrow aspirate may be added to whole blood prior or during isolation of platelet-rich plasma in step 120. Such methods include those described in U.S. Application Publication No. 2006/0278588, Woodell-May, published Dec. 14, 2006.

In some embodiments, the cBMA and Protein Solution may be may produced simultaneously. Thus, in reference to FIG. 1 and the processes described above, bone marrow aspirate may be added to the whole blood obtained in step 115, prior to or during the contacting with a solid extraction material in step 140; such a process involves operation of both steps 115 and 130. For example, bone marrow aspirate may be added to whole blood prior or during isolation of platelet-rich plasma in step 120. Such methods include those described in U.S. Application Publication No. 2006/0278588, Woodell-May, published Dec. 14, 2006.

Pharmaceutical actives among those useful herein include herein include organic molecules, proteins, peptides, peptidomimetics, nucleic acids, nucleoproteins, antisense molecules, polysaccharides, glycoproteins, lipoproteins, carbohydrates and polysaccharides, botanical extracts, and synthetic and biologically engineered analogs thereof, living cells (other than cytokine-producing cells) such as chondrocytes, bone marrow cells, viruses and virus particles, natural extracts, and combinations thereof. Specific non-limiting examples of bioactive materials include hormones, antibiotics and other anti-infective agents, hematopoietics, thrombopoietics, antiviral agents, antitumor agents (chemotherapeutic agents), antipyretics, analgesics, anti-inflammatory agents, antiallergy agents, vasodilators, cytokines, growth factors, gene regulators, vitamins, minerals and other nutritionals, nutraceuticals and combinations thereof. In some embodiments, compositions may comprise growth factors in addition to those present in the Protein Solution, such Platelet-Derived Growth Factor (PDGF), Transforming Growth Factor Beta (TGF-β), Insulin-Like Growth Factor (IGF), Fibroblast Growth Factor (FGF), Epidermal Growth Factor (EGF), Vascular Endothelial Growth Factor (VEGF), and Bone Morphogenetic Proteins (BMPs).

The compositions may comprise a carrier material, in addition to any liquid comprising the Protein Solution. It should be understood that in various embodiments of the present technology, methods of treatment employ the Protein Solution as comprised and made above, without further carrier, by direct injection or other application to the site of treatment. However, in other embodiments, an additional carrier material may be used for such reasons as for ease of administration, to facilitate administration using a particular delivery device, enhancing activity, an increasing the length of time the Protein Solution remains at the site of administration. Carriers among those useful herein include saline, hyaluronic acid, collagen, buffers (such as Hank's Buffer), cell culture media, blood products (such as PRP and platelet poor plasma), and mixtures thereof.

Protein Solutions, and compositions comprising Protein Solutions may be sterilized prior to administration, by any suitable method. For example, a Protein Solution may be sterilized by including a sterile filter to process the product made by the processes described above. In some embodiments, an antibiotic may be included in the solid extraction material during the contacting step described above, or may be added at one or more of the various steps in the methods and treatments described herein. Alternatively, or in addition, the Protein Solution may be produced aseptically.

Protein Solutions and compositions comprising Protein Solutions may also be lyophilized (freeze drying, or cryodesiccation) after production, using methods among those known in the art. Thus, as depicted in FIG. 1, the Protein Solution can be lyophilized after it is isolated from the solid extraction material. When freeze dried, the anti-inflammatory cytokine composition can be hydrated with a suitable media 170, at a time before administration or at a time of administration. Hydration may be accomplished by mixing the composition with a solution including saline, buffers, blood, blood fractions, bone marrow aspirate, concentrated bone marrow aspirate, and combinations thereof.

The present technology also provides compositions comprising components derived from blood or other tissue that are suitable for allogeneic administration. In particular, such compositions may comprise proteins and other components isolated from a mammalian subject, or a plurality of mammalian subjects, other than the subject to whom the composition is to be administered in a method of this technology. In further reference to FIG. 1, compositions made by contacting a cytokine cell suspension with a solid extraction material may be made suitable for allogeneic administration by freeze drying, as depicted in step 160, after isolation of the Protein Solution from the solid extraction material. In some embodiments, the composition can be processed to remove cytokine-producing cells present in the Protein Solution composition after contacting step 140. Methods for removing cytokine-producing cells include those known in the art, including filtering, clotting, and gravimetric methods. In some embodiments, isolating the blood fraction comprising plasma and removing cytokine-producing cells are performed essentially simultaneously. Thus, the present technology provides methods for making a non-immunogenic anti-inflammatory cytokine composition, comprising:
  (a) obtaining a cytokine cell suspension from a mammalian donor;
  (b) contacting the liquid with solid extraction material to generate a composition rich in interleukin-1 receptor antagonist;
  (c) removing cytokine-producing cells from the composition; and
  (d) freeze drying the composition to produce the non-immunogenic anti-inflammatory cytokine composition.

In some embodiments, a crypreservative storage solution is be added to the Protein Solution, to provide stability for subsequent storage at reduced temperatures. Suitable storage solutions include those in the art, such as glycerol and dimethylsulfoxide (DMSO). The composition may be stored at reduced temperatures, such as from about 1° C. to about 6° C. In some embodiments, the composition is stored under liquid nitrogen, at about −80° C. Preferably, the cryopreservative storage solution is removed from the Protein Solution prior to administration to a mammalian subject. Removal of the storage solution may be performed by methods including those known in the art for processing stored blood comprising cryopreservatives. Washing may be performed using a wash solution, such as saline. In such embodiments, the blood type of the subject to be treated may be matched to the blood type of the donor from whom the cytokine cell suspension was obtained.

Methods of Treatment

The present technology provides methods for the treatment of peripheral vascular disease (also known as peripheral artery disease and peripheral artery occlusive disease) in a human or other mammalian subject, comprising administration of a Protein Solution of the present technology to site of the PVD in the subject. As referred to herein, "treatment" includes one or more of preventing enlargement or progression of a lesion associated with PVD, reducing the size of a lesion associated with PVD, healing of the PVD lesion, improving arterial blood flow in an occluded artery (which may be totally or partially occluded), and reducing or eliminating pain associated with PVD. In various embodiments, the site of the PVD is in extremity, such as an arm or leg. In various embodiments, PVD is associated with an inflammatory disorder, including inflammation mediated by IL1-ra.

In various embodiments, methods are for the treatment of PVD in a human. In other embodiments, treatment is for PVD in non-human mammals, such as companion, working, and sports animals. For example, such methods of this technology may be used for the treatment of PVD in horses.

In various embodiments, methods of the present technology comprise a point-of-care method for making a Protein Solution. As referred to herein, a "point-of-care method" wherein the processes of the present technology are performed at a time proximate to the administration of the Protein Solution to the subject being treated. Such methods may be performed at a location proximate, such as in the same room (for example, bed side) or otherwise immediately adjacent, to the mammalian subject to be treated with the Protein Solution. In various embodiments, a "proximate time" may be, for example, within 12 hours, within 8 hours, within 2 hours, within 1 hour or within 30 minutes of administration of the Protein Solution to the subject.

In some embodiments, the Protein Solution is administered with a concomitant therapy. Such therapies include, for example, the administration of pharmaceutical actives or biologics, as described above. In some embodiments, concomitant therapies are administered concurrently with a Protein Solution. For example, methods may comprise administration of a Protein Solution with a safe and effective amount of an active selected from the group consisting of analgesics and glucocorticosteroids.

In some embodiments, methods comprise administration of a Protein Solution with concentrated bone marrow aspirate, as described above. For example, cBMA and a Protein Solution may be administered concomitantly.

Methods of the present technology generally comprise administration of a Protein Solution to the site of PVD in a mammalian subject. Administration of the Protein Solution can be performed with any suitable device, including such devices known in the art for topical delivery of compositions to the muscle and vascular tissue. For example, topical delivery for treatment of PVD may comprise injection of a Protein Solution in or near an occluded artery, or at or near tissue adjacent to the artery Embodiments of the present technology are further illustrated through the following non-limiting examples.

Example 1

Preparing and Characterizing a Protein Solution

A Protein Solution rich in interleukin-I receptor antagonist is prepared from seven consented human providers. Blood (55 mL) is drawn into a 60 cc syringe with 5 mL of anticoagulant citrate dextrose solution A (ACD-A, Citra Labs, Braintree, Mass.). Platelet-rich plasma (PRP) is created using the GPS® III platelet concentration system (800-1 003A, Biomet Biologics, Warsaw, Ind.) according to the instructions for use. The solution is generated by adding 6 mL of PRP to a modified Plasmax device containing 1 gram of polyacrylamide beads (Biomet Biologics, Warsaw, Ind.). The IL-1ra solution is removed from the Plasmax devices and frozen at minus 50° C. for the assay. Cytokine content is assayed on a 16-plex ELISA (Searchlight Protein Array, Aushon Biosystems, Billerica, Mass.). The analytes included IL-4, IL-10, IL-11, IL-13, IL-1ra, IFN-γ, sTNF-RI, sTNF-RII, IL-1α, IL-1β, TNF-α, IL-17, IL-18, bFGF, TBF-β1, and TBF-β2.

The solution contains both anabolic (bFGF, TGF-β1, TGF-β2 (see Table 3)) and anti-inflammatory (IL-1ra, sTNF-RI, sTNF-RII, IL-4, IL-10, IL-11, IL-13, IFN-γ, (see Table 4)) cytokines without expressing large doses of catabolic cytokines (IL-1α, IL-13, TNF-α, IL-17, IL-18 (see Table 5)). The anti-inflammatory cytokines IL-1ra and sTNF-R are all detected in ng/mL quantities, while all of the catabolic analytes were in pg/mL quantities. However, donor-to-donor variability is detected. Correlations between the catabolic cytokines IL-1 and TNF-α and anti-inflammatory analytes IL-1ra and sTNF-R are compared, but no large correlations detected (Table 6). On average, there is about 13.260 times more IL-1ra than IL-1α and about 7,561 times more than IL-1β.

TABLE 3

Anabolic cytokines in the solution.

| Donor | bFGF | TGF-β1 | TGF-β2 |
|---|---|---|---|
| 1 | 18.5 | 1,458,008 | 153,833 |
| 2 | 10.7 | 1,137,404 | 119,545 |
| 3 | 11.9 | 585,298 | 70,544 |
| 4 | 4.9 | 1,342,442 | 162,707 |
| 5 | 20.0 | 1,579,361 | 204,670 |
| 6 | 7.7 | 1,393,746 | 170,345 |
| 7 | 13.9 | 1,474,155 | 174,502 |
| Average ± SD | 12.5 ± 5.5 | 1,281,488 ± 336,345 | 150,878 ± 43,617 |

TABLE 4

Anti-inflammatory cytokines in the solution.

| Donor | IFN-γ | IL-4 | IL-10 | IL-13 | IL-1ra | TNF-RI | TNF-RII | IL-11 |
|---|---|---|---|---|---|---|---|---|
| 1 | <0.4 | 2.1 | 0.5 | 3.5 | 9,660 | 2,728 | 2,249 | <2.0 |
| 2 | <0.4 | 1.3 | 0.3 | 2.8 | 17,477 | 5,120 | 2,900 | <2.0 |
| 3 | <0.4 | <0.8 | 0.3 | 0.1 | 23,126 | 6,247 | 2,446 | <2.0 |
| 4 | 40.4 | 59.9 | 8.9 | 19.9 | 10,458 | 4,374 | 2,612 | <2.0 |
| 5 | 30.2 | 33.9 | 23.3 | 15.8 | 13,462 | 2,763 | 1,394 | <2.0 |
| 6 | 2.6 | 23.3 | 1.4 | 25.6 | 8,813 | 2,992 | 2,716 | <2.0 |

TABLE 4-continued

Anti-inflammatory cytokines in the solution.

| Donor | IFN-γ | IL-4 | IL-10 | IL-13 | IL-1ra | TNF-RI | TNF-RII | IL-11 |
|---|---|---|---|---|---|---|---|---|
| 7 | 0.7 | 1.2 | 0.6 | 1.8 | 11,277 | 3,330 | 1,915 | <2.0 |
| Average ± SD | 10.7 ± 17.0 | 17.5 ± 22.9 | 5.0 ± 8.7 | 9.9 ± 10.3 | 13,468 ± 5,154 | 3,936 ± 1,356 | 2,319 ± 520 | <2.0 ± 0 |

TABLE 5

Catabolic cytokines in the solution.

| Donor | IL-17 | TNF-α | IL-1α | IL-1β | IL-18 |
|---|---|---|---|---|---|
| 1 | 3.1 | 16.0 | <0.8 | 1.5 | 239 |
| 2 | 1.2 | <2.3 | 2.5 | 3.3 | 559 |
| 3 | 0.7 | <2.3 | 1.8 | 2.3 | 511 |
| 4 | 28.9 | 195 | 0.8 | 1.3 | 329 |
| 5 | 33.8 | 661 | 0.8 | 2.0 | 450 |
| 6 | 22.0 | 105 | 0.3 | 1.7 | 333 |
| 7 | 6.7 | <2.3 | 1.9 | 1.0 | 787 |
| Average ± SD | 13.8 ± 14.1 | 141 ± 241 | 1.3 ± 0.8 | 1.9 ± 0.8 | 458 ± 183 |

TABLE 6

Correlation analysis.

| Analytes compared | $R^2$ | Ratio |
|---|---|---|
| IL-1ra and IL-1α | 0.46 | 13,260X |
| IL-1ra and IL-1β | 0.45 | 7,561X |
| TNF-RI and TNF-α | 0.17 | 945X |
| TNF-RII and TNF-α | 0.47 | 477X |

Example 2

Generation of IL-1ra from Platelet-Rich Plasma

An IL-1 ra-rich solution is created as follows. Whole blood (70 mL) anticoagulated (10%) with ACD-A (Braintree, Mass., USA) is drawn from 5 healthy volunteers. A portion (10 mL) is reserved for a whole blood measurement. Platelet-rich plasma (PRP) (6 mL) is produced using the GPS® II System (Biomet Biologics, LLC, Warsaw. Ind., USA). Complete blood counts are collected for the whole blood and PRP samples following a validated procedure, as described in Woodell-May J E, Ridderman D N, Swift M J, Higgins J. "Producing Accurate Platelet Counts for Platelet Rich Plasma: Validation of a Hematology Analyzer and Preparation Techniques for Counting" J. Craniofac. Surg. (2005) Sep. 16(5):749-56.

Following the PRP production, 5 mL of the PRP is added to a modified plasma concentration device (Plasmax™, Biomet Biologics LLC, Warsaw, Ind., USA) and incubated with polyacrylamide desiccating beads in the device for 24 hours at room temperature. Following the contact with polyacrylamide beads the electromagnetic field, the plasma concentration device is centrifuged to separate the serum fraction.

To analyze baseline IL-1ra levels at time zero, the whole blood and PRP samples are activated with 50 μL of thrombin and 10% CaCl2 (1,000 units/mL). A blood clot is formed and incubated for 30 minutes at room temperature. Following incubation, the clot is centrifuged for 5 minutes at 3,000 rpm. Serum is collected from the clots and retained for ELISA analysis. The serum fraction from the plasma concentrator does not require activation by thrombin, and is tested directly. All samples are analyzed for IL-1ra using an ELISA kit (IL-1ra Quantikine™ Kit, R&D Systems, Minneapolis, Minn., USA).

The PRP samples result in about an eight-fold increase in platelets, about five-fold increase in total white blood cells (WBCs), about nine-fold increase in the monocyte fraction of the WBCs, and about a three-fold increase in the PMN fraction of the WBCs. The IL-1ra production in the whole blood and PRP samples is correlated most closely to the WBC concentration. The five-fold increase in the PRP is likely due to the increase in WBCs, and both the whole blood and PRP IL-1ra values can be considered baseline IL-1ra content. This is in contrast to the 195-fold increase in IL-1ra following incubation in the plasma concentrator. This plasma concentration device typically results in a 3-fold increase in plasma protein concentration due to a volume reduction caused by the desiccation process. This 3-fold decrease in volume does not account for the levels of increase seen in the amount of IL-1ra. Therefore, this level of increase indicates stimulation of WBCs to produce IL-1ra during the contact with the solid extraction material (e.g., polyacrylamide beads) and electromagnetic field stimulation.

Correlation analysis demonstrates that IL-1ra production is more closely correlated with the increase in WBCs than the platelet content. The IL-1ra levels do not correlate as closely with the WBC population in the PRP. This is not surprising since the WBC are not activated, and the serum is collected by thrombin activation of the plasma. However, it is possible that the WBC, once activated in the plasma concentration device, participate in the significant production of IL-1ra seen in this example.

Example 3

Production of Protein Solution from PRP

Anticoagulated blood (120 cc) is collected from 5 human donors. Platelet-rich plasma (PRP) is prepared using GPS® III disposables (Biomet Biologics LLC, Warsaw, Ind., USA). PRP is loaded into modified plasma concentration devices (Plasmax™, Biomet Biologics LLC, Warsaw, Ind., USA) and processed. The output is divided into 4 groups: IL-1ra in concentrated plasma with and without thrombin activation (1000 U/mL in 1M CaCl2), or cell-free IL-1ra with and without thrombin activation. IL-1ra is measured using ELISA (R&D Systems) over time.

The PRP contacts polyacrylamide beads in the Plasmax™ device while electromagnetic field stimulation is provided using a capacitively coupled electromagnetic field.

Unclotted PRP produces an average of about 50 ng over 24 hrs. The cell-free samples produce about 34 ng without changing over 24 hrs. Once clotted, the elution of IL-1ra is slowed, with only about 30% being eluted after 10 hours.

Release in the cell-free samples is also delayed, but eluted 100% of available IL-1ra after 10 hours.

Example 4

Generation of Protein Solution and Characterization of Cytokine Levels in Healthy Subjects and Osteoarthritis Subjects An Autologous Protein Solution (APS) from healthy patients are prepared as follows for the measurement of growth factors. 72 ml of anticoagulated whole blood are drawn by venipuncture from each of six donors. 3 ml of each donor's anticoagulated whole blood are aliquoted into microcentrifuge tubes and frozen at −50° C. 60 ml of the anticoagulated whole blood is loaded into GPS® III disposable devices (Biomet Biologics LLC, Warsaw, Ind., USA), which is processed according to the manufacturer's instructions to produce PRP. The PRP is removed from the GPS® III devices and added to Plasmax™ devices (Biomet Biologics LLC, Warsaw, Ind., USA), which is processed according to the manufacturer's instructions to produce APS. APS is extracted from each device, aliquoted into microcentrifuge tubes, and frozen at −50° C. Each sample, whole blood and PRP, is subjected to three freeze-thaw cycles. Quantikine Human Immunoassays (R&D Systems, Inc., Minneapolis, Minn.) for VEGF, PDGF-BB, PDGF-AB, EGF, TGF-β1, TGF-β2, and IGF-1 are run in duplicate according to the manufacturer's instructions for each APS and whole blood sample.

APS from healthy patients is prepared as above for the measurement of anti-inflammatory cytokines. Quantikine Human Immunoassays (R&D Systems, Inc., Minneapolis, Minn.) for IL-1ra, IL-1β, IL-8, sTNF-RI, TNF-α, IL-6, sTNF-RII, IL-10, IL-13, and IL-4 are run in duplicate according to the manufacturer's instructions for each APS and whole blood sample. Immunoassays are also performed to detect hepatocyte growth factor (HGF) and soluble IL-1RII.

APS from 105 osteoarthritis patients is prepared as above for the measurement of growth factors anti-inflammatory cytokines. The APS is stored at −50° C. or in dry ice.

Cytokine concentrations are compared between healthy donors and OA patients in baseline blood and APS. IL-1β is concentrated at a higher level in OA patients, but the fold increase is still much lower than that of IL-1ra. Other cytokines and growth factors that are concentrated at least to the level of that observed in healthy donors include sTNF-RI, IGF-I, IL-8, VEGF, and IL-6. The soluble cytokines sTNF-RII and sIL-1RII are concentrated to a level not quite as high but very similar to the healthy concentration level. The results are displayed in Table 7.

TABLE 7

Concentration of growth factors and anti-inflammatory cytokines from APS derived from healthy patients and patients with osteoarthritis (in pg/ml).

| Cytokine | | Baseline | | APS | | Fold Increase |
|---|---|---|---|---|---|---|
| | | Average | StDev | Average | StDev | Average |
| VEGF | Healthy | 276 | 109 | 742 | 494 | 2.7 |
| | OA | 484 | 201 | 1710 | 1025 | 3.8 |
| IL-1β | Healthy | 3.4 | 2 | 3.8 | 0.8 | 1.1 |
| | OA | 3.3 | 1.1 | 8.9 | 7.3 | 2.8 |

TABLE 7-continued

Concentration of growth factors and anti-inflammatory cytokines from APS derived from healthy patients and patients with osteoarthritis (in pg/ml).

| Cytokine | | Baseline | | APS | | Fold Increase |
|---|---|---|---|---|---|---|
| | | Average | StDev | Average | StDev | Average |
| IL-8 | Healthy | 74 | 16 | 315 | 198 | 4.3 |
| | OA | 73.5 | 29.6 | 287.9 | 192.7 | 4.2 |
| IL-6 | Healthy | 3.1 | 0.4 | 3.4 | 0.7 | 1.1 |
| | OA | 1.8 | 1.3 | 3 | 3.5 | 1.6 |
| TNF-α | Healthy | ND | ND | 3.4 | 0.7 | ND |
| | OA | 2.4 | 2 | 4.3 | 3 | 5.3 |
| IL-1ra | Healthy | 8092 | 2536 | 30853 | 16737 | 3.8 |
| | OA | 7576 | 2469 | 41896 | 19669 | 5.9 |
| sTNF-RII | Healthy | 2485 | 338 | 9491 | 1387 | 3.8 |
| | OA | 1491 | 492 | 5060 | 1946 | 3.5 |
| PDGF-AB | Healthy | 13400 | 3400 | 91700 | 24100 | 6.8 |
| | OA | 16799 | 5731 | 37889 | 24922 | 2.5 |
| PDGF-BB | Healthy | 4702 | 1027 | 23810 | 6126 | 5.1 |
| | OA | 5306 | 2422 | 11936 | 8655 | 2.5 |
| IGF-I | Healthy | 114000 | 30000 | 155000 | 34000 | 1.4 |
| | OA | 79072 | 22137 | 118060 | 42827 | 1.5 |
| EGF | Healthy | 240 | 71 | 1227 | 300 | 5.1 |
| | OA | 374 | 199 | 707 | 489 | 2.2 |
| sTNF-RI | Healthy | 629 | 76 | 2408 | 338 | 3.8 |
| | OA | 808 | 275 | 3011 | 964 | 3.9 |
| TGF-β1 | Healthy | 25717 | 11131 | 181245 | 56420 | 7.1 |
| | OA | 56594 | 56940 | 153567 | 145973 | 4.2 |
| sIL-1RII | Healthy | 11,786 | ND | 26,000 | ND | 2.2 |
| | OA | ND | ND | ND | ND | ND |
| HGF | Healthy | 782 | ND | 3244 | ND | 4.1 |
| | OA | ND | ND | ND | ND | ND |

Example 5

Generation of a Protein Solution from Adipose Tissue

Adipose stromal cells are prepared as follows. Adipose tissue is minced into small pieces (about 1 cm3) and digested in 2 mg/mL type I collagenase (Worthington Biochemical Corp., Lakewood, N.J.) under intermittent mechanical agitation in a water bath at 37° C. for 180 minutes. Digestion can be neutralized by the addition of medium or a blood-derived solution. The cell suspension is centrifuged (300×g for 7 minutes at 25° C.) followed by removal of the supernatant from the cell pellet. The pellet is then re-suspended in a compatible solution to provide a liquid volume comprising adipose stromal cells.

Alternatively, the pellet is suspended with whole blood obtained from the subject, and added to a GPS™ Platelet Concentrate System, from Biomet Biologics, Inc. (Warsaw, Ind.). Following centrifugation, the platelet-rich plasma layer, which also contains the adipose stromal cells, is extracted from the system.

The adipose stromal cells, optionally including platelet-rich plasma, are then combined with polyacrylamide beads and subjected to a pulsed electromagnetic field by using a pair of Helmholtz coils to stimulate production of IL-1ra. The adipose stromal cells and polyacrylamide beads are separated from the liquid solution to obtain a solution rich in IL-1ra.

Example 6

Generation of Protein Solution from Lipoaspirate

A therapeutic composition of IL-1ra is generated from stromal cells isolated from adipose tissue. Isolation of human stromal cells is performed by obtaining human subcutaneous adipose tissue from lipoaspiration/liposuction procedures and digesting the tissue in collagenase type I solution (Worthington Biochemical Corp., Lakewood, N.J.) under gentle agitation for 1 hour at 37° C. The dissociated cells are filtered with 500 µm and 250 µm Nitex filters. The fraction is centrifuged at 300×g for 5 minutes. The supernatant is discarded and the cell pellet is re-suspended in a compatible liquid solution, such as a blood-derived solution.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The disclosure of all patents and patent applications cited in this disclosure are incorporated by reference herein.

The description and specific examples, while indicating embodiments of the technology, are intended for purposes of illustration only and are not intended to limit the scope of the technology. Equivalent changes, modifications and variations of specific embodiments, materials, compositions and methods may be made within the scope of the present technology, with substantially similar results. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "prefer" or "preferable" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein. Further, as used herein the term "consisting essentially of" recited materials or components envisions embodiments "consisting of" the recited materials or components.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

What is claimed is:

1. A method for improving arterial blood flow in an occluded artery, comprising: concentrating whole blood, a fraction of whole blood, white blood cells, bone marrow, a fraction of bone marrow, adipose tissue, a fraction of adipose tissue, or a combination of any of the foregoing, obtained from the subject to form an autologous therapeutic composition; and administering the therapeutic composition at or near the ischemic tissue, the therapeutic composition comprising at least about 10,000 pg/ml interleukin-1 receptor antagonist (IL-ira), at least about 15,000 pg/ml soluble interkeukin-1 receptor II (sIL-iRII), and at least two proteins selected from at least about 1,200 pg/ml soluble tumor necrosis factor receptor I (sTNF-RI), at least about 3,000 pg/ml soluble tumor necrosis factor receptor II (sTNF-RII), at least about 130,000 pg/ml insulin-like growth factor-I (IGF-I), at least about 800 pg/ml epidermal growth factor (EGF), at least about 1000 pg/ml hepatocyte growth factor (HGF), at least about 35,000 pg/ml platelet-derived growth factor-AB (PDGF-AB), at least about 10,000 pg/ml PDGF-BB platelet-derived growth factor-BB (PDGF-BB), at least about 500 pg/ml vascular endothelial growth factor (VEGF), and at least about 100,000 pg/ml transforming growth factor-β1 (TGF-β1), wherein the concentration of each selected protein in the therapeutic composition is greater than the concentration of the selected protein in the biological material.

2. The method according to claim 1, wherein the therapeutic composition further comprises the subject's white blood cells at a concentration of at least 15,000/μl.

3. The method according to claim 1, wherein the therapeutic composition further comprises
the subject's platelets at a concentration of at least 400,000/μl.

4. A method for improving arterial blood flow in an occluded artery, comprising topically injecting at or near the site of the ischemic tissue an autologous composition comprising: at least 10,000 pg/ml interleukin-1 receptor antagonist (IL-1ra); at least 15,000 pg/ml soluble interleukin-1 receptor II (sIL-IRII); and at least 1,000 pg/ml hepatocyte growth factor (HGF), wherein the IL-ira, the sTNF-R1 and the sIL-1RII are prepared from whole blood, a fraction of whole blood, bone marrow, a fraction of bone marrow, adipose tissue, a fraction of adipose tissue, or a combination of any of the foregoing.

5. The method according to claim 4, wherein the composition further comprises at least about 1,200 pg/ml soluble tumor necrosis factor receptor I (sTNF-RI).

6. The method according to claim 4, wherein the composition further comprises a protein selected from the group consisting of soluble tumor necrosis factor-receptor II (sTNF-RII), insulin-like growth factor-I (IGF-1), epidermal growth factor (EGF), hepatocyte growth factor (HGF), platelet-derived growth factor-AB (PDGF-AB), platelet-derived growth factor-BB (PDGF-BB), vascular endothelial growth factor (VEGF), transforming growth factor-β1 (TGF-β1), and sIL-1RII, and mixtures of any of the foregoing, wherein the concentration of the selected protein in the composition is greater than the concentration of the protein in the subject's blood.

7. The method according to claim 4, wherein the composition further comprises concentrated bone marrow aspirate.

8. A method for improving arterial blood flow in an occluded artery, comprising: obtaining a cytokine cell suspension from the subject; processing the cytokine-cell suspension to produce an autologous protein solution comprising at least 10,000 pg/ml interleukin-1 receptor antagonist (IL-1ra) and at least 15,000 pg/ml soluble interleukin-1 receptor II (sIL-IRII), and hepatocyte growth factor at a concentration of at least about 1,000 pg/ml wherein the ratio of IL-Ira to interleukin-β1 in the composition is greater than 1000, and the ratio of sIL-1RII to IL-βI in the composition is greater than 1; and
administering the autologous protein solution by topical injection at or near the site of the tissue ischemia.

9. The method according to claim 8 wherein the cytokine cell suspension comprises whole blood, bone marrow aspirate, adipose tissue, urine, a fraction of any one of the foregoing, and a mixture of any of the foregoing.

10. The method according to claim 8, wherein processing comprises separating blood to create a platelet-rich plasma fraction comprising white blood cells at a concentration of at least 15,000/μl.

11. The method according to claim 8, wherein processing includes contacting the cytokine-cell suspension with polyacrylamide beads to form the autologous protein solution.

12. The method according to claim 8, wherein processing includes contacting the cytokine-cell suspension with a solid extraction material.

13. The method according to claim 12, wherein the solid extraction material is selected from the group consisting of corundum, quartz, titanium, dextran, agarose, polyacrylamide, polystyrene, polyethylene, polyvinyl chloride, polypropylene, and combinations thereof.

14. The method according to claim 13, wherein the solid extraction material comprises a form selected from the group consisting of a bead, fiber, powder, porous material, and combinations thereof.

15. The method according to claim 12, wherein the solid extraction material comprises a desiccating material.

16. The method according to claim 8, further comprising:
obtaining bone marrow aspirate from the subject;
concentrating the bone marrow aspirate to produce a concentrated bone marrow aspirate (cBMA);
administering the cBMA to the subject.

17. The method according to claim 16, wherein the autologous protein solution further comprises soluble tumor necrosis factor receptor II at a concentration of at least about 3,000 pg/ml.

18. The method according to claim 8, wherein the autologous protein solution comprises white blood cells at a concentration of at least about 30,000/μl.

19. The method according to claim 8, wherein treating tissue ischemia includes healing a lesion at or near the site of the tissue ischemia.

* * * * *